US009717783B2

(12) United States Patent
Chackerian et al.

(10) Patent No.: US 9,717,783 B2
(45) Date of Patent: Aug. 1, 2017

(54) IMMUNOGENIC HPV L2-CONTAINING VLPS AND RELATED COMPOSITIONS, CONSTRUCTS, AND THERAPEUTIC METHODS

(71) Applicant: STC.UNM, Albuquerque, NM (US)

(72) Inventors: Bryce Chackerian, Albuquerque, NM (US); David S. Peabody, Albuquerque, NM (US); Ebenezer Tumban, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 183 days.

(21) Appl. No.: 13/946,562

(22) Filed: Jul. 19, 2013

(65) Prior Publication Data
US 2014/0105924 A1 Apr. 17, 2014

Related U.S. Application Data

(63) Continuation-in-part of application No. 13/577,484, filed as application No. PCT/US2011/024030 on Feb. 8, 2011, now Pat. No. 9,533,057, application No. 13/946,562, which is a continuation-in-part of application No. PCT/US2013/020960, filed on Jan. 10, 2013.

(60) Provisional application No. 61/302,836, filed on Feb. 9, 2010, provisional application No. 61/334,826, filed on May 14, 2010, provisional application No. 61/585,839, filed on Jan. 12, 2012.

(51) Int. Cl.
A61K 39/12 (2006.01)
A61K 39/00 (2006.01)

(52) U.S. Cl.
CPC ...... A61K 39/12 (2013.01); A61K 2039/5258 (2013.01); A61K 2039/58 (2013.01); C12N 2710/20034 (2013.01); C12N 2795/18023 (2013.01); C12N 2795/18071 (2013.01)

(58) Field of Classification Search
None
See application file for complete search history.

(56) References Cited

U.S. PATENT DOCUMENTS

| 6,174,532 | B1 | 1/2001 | Campo et al. |
| 7,008,651 | B2 | 3/2006 | Ambuel et al. |
| 8,404,244 | B2* | 3/2013 | Schiller et al. ............ 424/186.1 |
| 2002/0136736 | A1 | 9/2002 | Jarrett et al. |
| 2006/0046291 | A1 | 3/2006 | Hunt |
| 2008/0213293 | A1 | 9/2008 | Palmer et al. |
| 2009/0028886 | A1 | 1/2009 | Bachmann et al. |
| 2009/0054246 | A1* | 2/2009 | Peabody et al. .................. 506/7 |
| 2009/0155302 | A1 | 6/2009 | Bachmann et al. |

FOREIGN PATENT DOCUMENTS

| WO | 9300436 | 1/1993 |
| WO | 2004052395 A1 | 6/2004 |
| WO | 2006083984 A1 | 8/2006 |
| WO | 2008082719 A2 | 7/2008 |
| WO | 2008115631 A2 | 9/2008 |

OTHER PUBLICATIONS

Peabody. Subunit fusion confers tolerance to peptide insertions in a virus coat protein. Arch Biochem Biophys. Nov. 1, 1997;347(1):85-92.*
Alphs, H. H., R. Gambhira, B. Karanam, J. N. Roberts, S. Jagu, J. T. Schiller, W. Zeng, D. C. Jackson, and R. B. Roden. 2008. Protection against heterologous human papillomavirus challenge by a synthetic lipopeptide vaccine containing a broadly cross-neutralizing epitope of L2. Proc Natl Acad Sci U S A 105:5850-5.
Bachmann, M. F., U. H. Rohrer, T. M. Kundig, K Burki, H. Hengartner, and R. M. Zinkemagel. 1993. The influence of antigen organization on B cell responsiveness. Science 262:1448-1451.
Bachmann, M. F., and R. M. Zinkemagel. 1997. Neutralizing antiviral B cell responses. Annu Rev Immunol 15:235-70.
Brunswick M., F. D. Finkelman, P. F. Highet, J. K Inman, H. M. Dintzis, and J. J. Mond. 1988. Picogram quantities of anti-Ig antibodies coupled to dextran induce B cell proliferation. J Immunol 140:3364-72.
Buck, C. B., N. Cheng, C. D. Thompson, D. R. Lowy, A. C. Steven, J. T. Schiller, and B. L Trus. 2008. Arrangement of L2 within the papillomavirus capsid. J Virol 82:5190-7.
Caldeira, J. C., and D. S. Peabody. 2007. Stability and assembly in vitro of bacteriophage PP7 virus-like particles. J Nanobiotechnology 5:10.
Campo, M. S., G. J. Grindley, B. W. O'Neil, L. M. Chandrachud, G. M. McGarvie, and W. F. Jarrett. 1993. Prophylactic and therapeutic vaccination against a mucosal papillomavirus. J Gen Virol. 74, 945-953.
Chackerian, B., L. Briglio, P. S. Albert, D. R. Lowy, and J. T. Schiller. 2004. Induction of autoantibodies to CCR5 in macaques and subsequent effects upon challenge with an R5-tropic simian/human immunodeficiency virus. J Virol 78:4037-47.
Chackerian, B., M. R. Durfee, and J. T. Schiller. 2008. Virus-like display of a neo-self antigen reverses B cell anergy in a B cell receptor transgenic mouse model. J Immunol 180:5816-25.

(Continued)

Primary Examiner — Michelle S Horning
(74) Attorney, Agent, or Firm — Henry D. Coleman; R. Neil Sudol

(57) ABSTRACT

The invention provides immunotherapeutic and prophylactic bacteriophage viral-like particle (VLPs) which are useful in the treatment and prevention of human papillomavirus (HPV) infections and related disorders, including cervical cancer and persistent infections associated with HPV. Related compositions (e.g. vaccines), nucleic acid constructs, and therapeutic methods are also provided. VLPs and related compositions of the invention induce high titer antibody responses against HPV L2 and protect against HPV challenge in vivo. VLPs, VLP-containing compositions, and therapeutic methods of the invention induce an immunogenic response against HPV infection, confer immunity against HPV infection, protect against HPV infection, and reduce the likelihood of infection by HPV infection.

14 Claims, 24 Drawing Sheets

(56) References Cited

OTHER PUBLICATIONS

Chackerian, B., D. R. Lowy, and J. T. Schiller. 2001. Conjugation of a self-antigen to papillomavirus-like particles allows for efficient induction of protective autoantibodies. J Clin Invest 108:415-23.

Chackerian, B., D. R. Lowy, and J. T. Schiller. 1999. Induction of autoantibodies to mouse CCR5 with recombinant papillomavirus particles. Proc. Natl. Acad. Sci. USA 96:2373-2378.

Chackerian, B., M. Rangel, Z. Hunter, and D. S. Peabody. 2006. Virus and virus-like particle-based immunogens for Alzheimer's disease induce antibody responses against amyloid-beta without concomitant T cell responses. Vaccine 24:6321-31.

Christensen, N. D., J. W. Kreider, N. C. Kan, and S. L. DiAngelo. 1991. The open reading frame L2 of cottontail rabbit papillomavirus contains antibody-inducing neutralizing epitopes. Virology 181:572-9.

Cornuz, J., S. Zwahlen, W. F. Jungi, J. Osterwalder, K. Klingler, G. van Melle, Y. Bangala, I. Guessous, P. Muller, J. Willers, P. Maurer, M. F. Bachmann, and T. Cerny. 2008. A vaccine against nicotine for smoking cessation: a randomized controlled trial. PLoS ONE 3:e2547.

Day, P. M., R. Gambhira, R. B. Roden, D. R. Lowy, and J. T. Schiller. 2008. Mechanisms of human papillomavirus type 16 neutralization by l2 cross-neutralizing and l1 type-specific antibodies. J Virol 82:4638-46.

Dintzis, H. M., R. Z. Dintzis, and B. Vogelstein. 1976. Molecular determinants of immunogenicity: the immunon model of immune response. Proc Natl Acad Sci U S A 73:3671-5.

Dintzis, R. Z., M. H. Middleton, and H. M. Dintzis. 1985. Inhibition of anti-DNP antibody formation by high doses of DNP-polyacrylamide molecules; effects of hapten density and hapten valence. J Immunol 135:423-7.

Fehr, T., D. Skrastina, P. Pumpens, and R. M. Zinkemagel. 1998. T cell-independent type I antibody response against B cell epitopes expressed repetitively on recombinant virus particles. Proc Natl Acad Sci U S A 95:9477-81.

Gambhira, R., S. Jagu, B. Karanam, P. E. Gravitt, T. D. Culp, N. D. Christensen, and R. B. Roden. 2007. Protection of rabbits against challenge with rabbit papillomaviruses by immunization with the N terminus of human papillomavirus type 16 minor capsid antigen L2. J Virol 81:11585-92.

Gambhira, R., B. Karanam, S. Jagu, J. N. Roberts, C. B. Buck, I. Bossis, H. Alphs, T. Culp, N. D. Christensen, and R. B. Roden. 2007. A protective and broadly cross-neutralizing epitope of human papillomavirus L2. J Virol 81:13927-31.

Ghim, S. J., A. B. Jenson, and R. Schlegel. 1992. HPV-1 L1 protein expressed in cos cells displays conformational epitopes found on intact virions. Virology 190:548-52.

Harro, C. D., Y. Y. Pang, R. B. Roden, A. Hildesheim, Z. Wang, M. J. Reynolds, T. C. Mast, R. Robinson, B. R. Murphy, R. A. Karron, J. Dillner, J. T. Schiller, and D. R. Lowy. 2001. Safety and immunogenicity trial in adult volunteers of a human papillomavirus 16 L1 virus-like particle vaccine. J Natl Cancer Inst 93:284-92.

Kawana, K., Y. Kawana, H. Yoshikawa, Y. Taketani, K. Yoshiike, and T. Kande. 2001. Nasal immunization of mice with peptide having a cross-neutralization epitope on minor capsid protein L2 of human papillomavirus type 16 elicit systemic and mucosal antibodies. Vaccine 19:1496-502.

Kimbauer, R., F. Booy, N. Cheng, D. R. Lowy, and J. T. Schiller. 1992. Papillomavirus L1 major capsid protein self-assembles into virus-like particles that are highly immunogenic. Proc Natl Acad Sci U S A 89:12180-12184.

Kimbauer, R., J. Taub, H. Greenstone, R. B. S. Roden, M. Durst, L. Gissmann, D. R. Lowy, and J. T. Schiller. 1993. Efficient self-assembly of human papillomavirus type 16 L1 and L1-L2 into virus-like particles. J Virol 67:6929-6936.

Koutsky, L. A., K. A. Ault, C. M. Wheeler, D. R. Brown, E. Barr, F. B. Alvarez, L. M. Chiacchierini, and K. U. Jansen. 2002. A controlled trial of a human papillomavirus type 16 vaccine. N Engl J Med 347:1645-51.

Li, Q., C. Cao, B. Chackerian, J. Schiller, M. Gordon, K. E. Ugen, and D. Morgan. 2004. Overcoming antigen masking of anti-amyloidbeta antibodies reveals breaking of B cell tolerance by virus-like particles in amyloidbeta immunized amyloid precursor protein transgenic mice. BMC Neurosci 5:21.

Lim, F., T. P. Downey, and D. S. Peabody. 2001. Translational repression and specific RNA binding by the coat protein of the Pseudomonas phage PP7. J Biol Chem 276:22507-13.

Lim, F., and D. S. Peabody. 2002. RNA recognition site of PP7 coat protein. Nucleic Acids Res 30:4138-44.

Lin, Y.-L., L. A. Borenstein, R. Selvakumar, R. Ahmed, and F. O. Wettstein. 1992. Effective vaccination against papilloma development by immunization with L1 or L2 structural protein of cottontail rabbit papillomavirus. Virology 187:612-619.

Mao, C., L. A. Koutsky, K. A. Ault, C. M. Wheeler, D. R. Brown, D. J. Wiley, F. B. Alvarez, O. M. Bautista, K. U. Jansen, and E. Barr. 2006. Efficacy of human papillomavirus-16 vaccine to prevent cervical intraepithelial neoplasia: a randomized controlled trial. Obstet Gynecol 107:18-27.

Milich, D. R., M. Chen, F. Schodel, D. L. Peterson, J. E. Jones, and J. L. Hughes. 1997. Role of B cells in antigen presentation of the hepatitis B core. Proc Natl Acad Sci U S A 94:14648-53.

Munoz, N., F. X. Bosch, S. de Sanjose, R. Herrero, X. Castellsague, K. V. Shah, P. J. Snijders, and C. J. Meijer. 2003. Epidemiologic classification of human papillomavirus types associated with cervical cancer. N Engl J Med 348:518-27.

Parkin, D. M., and F. Bray. 2006. Chapter 2: The burden of HPV-related cancers. Vaccine 24 Suppl 3:S3/11-25.

Pastrana, D. V., C. B. Buck, Y. Y. Pang, C. D. Thompson, P. E. Castle, P. C. FitzGerald, S. Kruger Neer, D. R. Lowy, and J. T. Schiller. 2004. Reactivity of human sera in a sensitive, high-throughput pseudovirus-based papillomavirus neutralization assay for HPV16 and HPV18. Virology 321:205-16.

Pastrana, D. V., R. Gambhira, C. B. Buck, Y. Y. Pang, C. D. Thompson, T. D. Culp, N. D. Christensen, D. R. Lowy, J. T. Schiller, and R. B. Roden. 2005. Cross-neutralization of cutaneous and mucosal Papillomavirus types with anti-sera to the amino terminus of L2. Virology 337:365-72.

Peabody, D. S. 1990. Translational repression by bacteriophage MS2 coat protein expressed from a plasmid. A system for genetic analysis of a protein-RNA interaction. J Biol Chem 265:5684-9.

Peabody, D. S., B. Manifold-Wheeler, A. Medford, S. K. Jordan, J. do Carmo Caldeira, and B. Chackerian. 2008. Immunogenic display of diverse peptides on virus-like particles of RNA phage MS2. J Mol Biol 380:252-63.

Richards, R. M., D. R. Lowy, J. T. Schiller, and P. M. Day. 2006. Cleavage of the papillomavirus minor capsid protein, L2, at a furin consensus site is necessary for infection. Proc Natl Acad Sci U S A 103:1522-7.

Roberts, J. N., C. B. Buck, C. D. Thompson, R. Kines, M. Bernardo, P. L. Choyke, D. R. Lowy, and J. T. Schiller. 2007. Genital transmission of HPV in a mouse model is potentiated by nonoxynol-9 and inhibited by carrageenan. Nat Med 13:857-61.

Roden, R. B., W. I. Yulzy, R. Fallon, S. Inglis, D. R. Lowy, and J. T. Schiller. 2000. Minor capsid protein of human genital papillomaviruses contains subdominant, cross-neutralizing epitopes. Virology 270:254-7.

Roden, R. B. S., N. L. Hubbert, R. Kimbauer, N. D. Christensen, D. R. Lowy, and J. T. Schiller. 1996. Assessment of the serological relatedness of genital human papillomaviruses by hemagglutination inhibition. J. Virol 70:3298-3301.

Rose, R. C., W. Bonnez, R. C. Reichman, and R. L. Garcea. 1993. Expression of human papillomavirus type 11 L1 protein in insect cells: in vivo and in vitro assembly of viruslike particles. J Virol 67:1936-44.

Schiller, J. T., and D. R. Lowy. 2001. Papillomavirus-like particle based vaccines: cervical cancer and beyond. Expert Opin Biol Ther 1:571-81.

Selinka, H. C., T. Giroglou, T. Nowak, N. D. Christensen, and M. Sapp. 2003. Further evidence that papillomavirus capsids exist in two distinct conformations. J Virol 77:12961-7.

(56) References Cited

OTHER PUBLICATIONS

Stanley, M., D. R. Lowy, and I. Frazer. 2006. Chapter 12: Prophylactic HPV vaccines: underlying mechanisms. Vaccine 24 Suppl 3:S3/106-13.

Tars, K., K. Fridborg, M. Bundule, and L. Liljas. 2000. The three-dimensional structure of bacteriophage PP7 from Pseudomonas aeruginosa at 3.7—A resolution. Virology 272:331-7.

Thyagarajan, R., N. Arunkumar, and W. Song. 2003. Polyvalent antigens stabilize B cell antigen receptor surface signaling microdomains. J Immunol 170:6099-106.

Tissot, A. C., P. Maurer, J. Nussberger, R. Sabat, T. Pfister, S. Ignatenko, H. D. Volk, H. Stocker, P. Muller, G. T. Jennings, F. Wagner, and M. F. Bachmann. 2008. Effect of immunisation against angiotensin II with CYT006-AngQb on ambulatory blood pressure: a double-blind, randomised, placebo-controlled phase IIa study. Lancet 371:821-7.

Zhang, L. F., J. Zhou, S. Chen, L. L. Cai, Q. Y. Bao, F. Y. Zheng, J. Q. Lu, J. Padmanabha, K. Hengst, K. Malcolm, and I. H. Frazer. 2000. HPV6b virus like particles are potent immunogens without adjuvant in man. Vaccine 18:1051-8.

Zhou, J., X. Y. Sun, D. J. Stenzel, and I. H. Frazer. 1991. Expression of vaccinia recombinant HPV 16 L1 and L2 ORF proteins in epithelial cells is sufficient for assembly of HPV virion-like particles. Virology 185:251-257.

Tumban E, Peabody J, Tyler M, Peabody DS, Chackerian B (2012) VLPs Displaying a Single L2 Epitope Induce Broadly Cross-Neutralizing Antibodies against Human Papillomavirus. PLOS ONE 7(11): e49751. doi:10.1371/journal.pone.0049751.

Burton, D. R., R. L. Stanfield, and I. A. Wilson. 2005. Antibody vs. HIV in a clash of evolutionary titans. Proc Natl Acad Sci U S A 102:14943-8.

Chackerian, B., C. Caldeira Jdo, J. Peabody, and D. S. Peabody. 2011. Peptide Epitope Identification by Affinity Selection on Bacteriophage MS2 Virus-Like Particles. J Mol Biol 409:225-37.

Ekiert, D. C., G. Bhabha, M. A. Elsliger, R. H. Friesen, M. Jongeneelen, M. Throsby, J. Goudsmit, and I. A. Wilson. 2009. Antibody recognition of a highly conserved influenza virus epitope. Science 324:246-51.

Johnson, K. M., R. C. Kines, J. N. Roberts, D. R. Lowy, J. T. Schiller, and P. M. Day. 2009. Role of heparan sulfate in attachment to and infection of the murine female genital tract by human papillomavirus. J Virol 83:2067-74.

Karanam, B., S. Jagu, W. K. Huh, and R. B. Roden. 2009. Developing vaccines against minor capsid antigen L2 to prevent papillomavirus infection. Immunol Cell Biol 87:287-99.

Law, M., T. Maruyama, J. Lewis, E. Giang, A. W. Tarr, Z. Stamataki, P. Gastaminza, F. V. Chisari, I. M. Jones, R. I. Fox, J. K. Ball, J. A. McKeating, N. M. Kneteman, and D. R. Burton. 2008. Broadly neutralizing antibodies protect against hepatitis C virus quasispecies challenge. Nat Med 14:25-7.

Sui, J., W. C. Hwang, S. Perez, G. Wei, D. Aird, L. M. Chen, E. Santelli, B. Stec, G. Cadwell, M. Ali, H. Wan, A. Murakami, A. Yammanuru, T. Han, N. J. Cox, L. A. Bankston, R. O. Donis, R. C. Liddington, and W. A. Marasco. 2009. Structural and functional bases for broad-spectrum neutralization of avian and human influenza A viruses. Nat Struct Mol Biol 16:265-73.

Durst M et al., 1983. A papillomavirus DNA from a cervical carcinoma and its prevalence in cancer biopsy samples from different geographic regions. Proc Natl Acad Sci USA 80:3812-3815.

Gissmann L et al. 1984. Presence of Human Papillomavirus in Genital Tumors. The Journal of Investigative Dermatology 83: 26s-28s.

Beckett D et al. 1988. Roles of Operator and Non-operator RNA Sequences in Bacteriophage R17 Capsid Assembly. J Mol Biol 204:939-947.

Lim F et al. 2002. RNA recognitions site of PP7 coat protein. Nucleic Acids Research 30:4138-4144.

Tatusova T A et al. 1999. BLAST 2 Sequences, a new tool for comparing protein and nucleotide sequences. FEMS Microbiology Letters 174:247-250.

Sambrook J et al. 2001. Molecular Cloning A Laboratory Manual. Third Edition. Cold Spring Harbor Laboratory Press, Cold Spring Harbor, New York.

Celts J E 1994. Cell Biology A Laboratory Handbook. Academic Press, San Diego, California.

Gait M J (Ed.) 1984. Oligonucleotide Synthesis A Practical Approach. IRL Press, Washington, D.C.

Hames B D and Higgins S J (Eds.) 1985. Nucleic Acid Hybridisation A Practical Approach. IRL Press, Washington, D.C.

Hames B D and Higgins S J (Eds.) 1984. Transcription and Translation A Practical Approach. IRL Press, Washington, D.C.

Freshney R I (Ed.) 1986. Animal Cell Culture a Practical Approach. IRL Press, Washington, D.C.

Woodward J (Ed.) 1985. Immobilized Cells and Enzymes A Practical Approach. IRL Press, Washington, D.C.

Perbal B V 1984. A Practical Guide to Molecular Cloning. John Wiley & Sons, Inc., United States of America.

Caldeira JC, et al. Immunogenic Display of Diverse Peptides, Including a Broadly Cross-Type Neutralizing Human Papillomavirus L2 epitope, on Virus-like Particles of the RNA Bacteriophage PP7. Vaccine, 2010;28(27):4384-4393.

Tumban E, et al. VLPs Displaying a Single L2 Epitope Induce Broadly Cross-Neutralizing Antibodies against Human Papillomarivus. PLOS ONE, 2012;7(11):e49751.

* cited by examiner

Plasmids for expression of recombinant PP7 coat protein, including pP7K, p2P7K32, pETP7K, and pET2P7K32.

FIGURE 2

Nucleotide Sequences:

p2P7K32 (SEQ ID NO. 1)

```
GACGAAAGGGCCTCGTGATACGCCTATTTTTATAGGTTAATGTCATGATAATAAT
GGTTTCTTAGACGTCAGGTGGCACTTTTCGGGGAAATGTGCGCGGAACCCCTATT
TGTTTATTTTTCTAAATACATTCAAATATGTATCCGCTCATGAGACAATAACCCTG
ATAAATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCG
TATTGACGCCGGGCAAGAGCAACTCGGTCGCCGCATACACTATTCTCAGAATGA
CTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTT
ACTTCTGACAACGATCGGAGGACCGAAGGAGCTAACCGCTTTTTGCACAACAT
GGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCG
CAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACACGACG
GGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGA
TTGATTTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAA
ATACTGTCCTTCTAGTGTAGCCGTAGTTAGGCCACCACTTCAAGAACTCTGTAGC
ACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACG
ACCTACACCGAACTGAGATACCTACAGCGTGAGCATTGAGAAAGCGCCACGCTT
CCCGAAGGGAGAAAGGCGGACAGGTATCCGGTAAGCGGCAGGGTCGGAACAGG
AGAGCGCACGAGGGAGCTTCCAGGGGGAAACGCCTGGTATCTTTATAGTCCTGT
CGGGTTTCGCCACCTCTGACTTGAGCGTCGATTTTGTGATGCTCGTCAGGGGGG
CGGAGCCTATGGAAAAACGCCAGCAACGCGGCCTTTTACGGTTCCTGGCCTTTT
GCTGGCCTTTTGCTCACATGTTCTTTCCTGCGTTATCCCTGATTCTGTGGATAAC
CGTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGCCT
CTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGG
CACCCCAGGCTTTACACTTTATGCTTCCGGCTCGTATGTTGTGTGGAATTGTGAGC
GGATAACAATTTCACACAGGAAACAGCTATGACCATGATTACGCCAAGCTTGCA
TGCCTGCAGGTCGACTCTAGATAGAGCCCTCAACCGGAGTTTGAAGCATGGCCA
AAACCATCGTTCTTTCGGTCGCGAGGCTACTCGCACTCTGACTGAGATCCAGTCC
ACCGCAGACCGTCAGATCTTCGAAGAGAAGGTCGGGCCTCTGGTGGGTCGGCTG
```

FIGURE 2 (Cont'd)

p2P7K32 (SEQ ID NO. 1) (Cont'd)

CGCCTCACGGCTTCGCTCCGTCAAAACGGAGCCAAGACCGCGTATCGCGTCAAC
CTAAAACTGGATCAGGCGGACGTCGTTGATTGCTCCACCAGCGTCTGCGGCGAG
CTTCCGAAAGTGCGCTACACTCAGGTATGGTCGCACGACGTGACAATCGTTGCGA
ATAGCACCGAGGCCTCGCGCAAATCGTTGTACGATTTGACCAAGTCCCTCGTCGC
GACCTCGCAGGTCGAAGATCTTGTCGTCAACCTTGTGCCGCTGGGCCGTGCTAGC
TCCAAAACCATCGTTCTTTCGGTCGGTACCGAGGCTACTCGCACTCTGACTGAGA
TCCAGTCCACCGCAGACCGTCAGATCTTCGAAGAGAAGGTCGGGCCTCTGGTGG
GTCGGCTGCGCCTCACGGCTTCGCTCCGTCAAAACGGAGCCAAGACCGCGTATC
GCGTCAACCTAAAACTGGATCAGGCGGACGTCGTTGATTGCTCCACCAGCGTCTG
CGGCGAGCTTCCGAAAGTGCGCTACACTCAGGTATGGTCGCACGACGTGACAAT
CGTTGCGAATAGCACCGAGGCCTCGCGCAAATCGTTGTACGATTTGACCAAGTCC
CTCGTCGCGACCTCGCAGGTTGAAGATCTTGTCGTCAACCTTGTGCCGCTGGGCC
GTAATAGACGCCGGCCATTCAAACATGAGGATTACCCATGTCGAAGACAACAAA
GAAGTTCGGATCCAATTCACTGGCCGTCGTTTTACAACGTCGTGACTGGGAAAAC
CCTGGCGTTACCCAACTTAATCGCCTTGCAGCACATCCCCCTTTCGCCATCTGGC
GTAATAGCGAAGAGGCCCGCACCGATCGCCCTTCCCAACAGTTGCGCAGCCTGA
ATGGCGAATGGCGCCTGATGCGGTATTTTCTCCTTACGCATCTGTGCGGTATTTC
ACACCGCATACGTCAAAGCAACCATAGTACGCGCCCTGTAGCGGCGCATTAAGC
GCGGCGGGTGTGGTGGTTACGCGCAGCGTGACCGCTACACTTGCCAGCGCCCTA
GCGCCCGCTCCTTTCGCTTTCTTCCCTTCCTTTCTCGCCACGTTCGCCGGCTTTCCC
CGTCAAGCTCTAAATCGGGGGCTCCCTTTAGGGTTCCGATTTAGTGCTTTACGGC
ACCTCGACCCCAAAAACTTGATTTGGGTGATGGTTCACGTAGTGGGCCATCGCCC
TGATAGACGGTTTTTCGCCCTTTGACGTTGGAGTCCACGTTCTTTAATAGTGGACT
CTTGTTCCAAACTGGAACAACACTCAACCCTATCTCGGGCTATTCTTTTGATTTAT
AAGGGATTTTGCCGATTTCGGCCTATTGGTTAAAAAATGAGCTGATTTAACAAAA
ATTTAACGCGAATTTTAACAAAATATTAACGTTTACAATTTTATGGTGCACTCTC
AGTACAATCTGCTCTGATGCCGCATAGTTAAGCCAGCCCCGACACCCGCCAACAC
CCGCTGACGCGCCCTGACGGGCTTGTCTGCTCCCGGCATCCGCTTACAGACAAGC
TGTGACCGTCTCCGGGAGCTGCATGTGTCAGAGGTTTTCACCGTCATCACCGAAA
CGCGCGA

FIGURE 2 (CONT'D)

pET2P7K32 (SEQ ID NO. 2)

TTCTTAGAAAAACTCATCGAGCATCAAATGAAACTGCAATTTATTCATATCAGGA
TTATCAATACCATATTTTTGAAAAAGCCGTTTCTGTAATGAAGGAGAAAACTCAC
CGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGT
GAGAAATCACCATGAGTGACGACTGAATCCGGTGAGAATGGCAAAAGCTTATGC
ATTTCTTTCCAGACTTGTTCAACAGGCCAGCCATTACGCTCGTCATCAAAATCAC
TCGCATCAACCAAACCGTTATTCATTCGTGATTGCGCCTGAGCGAGACGAAATAC
GCGATCGCTGTTAAAAGGACAATTACAAACAGGAATCGAATGCAACCGGCGCAG
GAACACTGCCAGCGCATCAACAATATTTTCACCTGAATCAGGATATTCTTCTAAT
ACCTGGAATGCTGTTTTCCCGGGGATCGCAGTGGTGAGTAACCATGCATCATCAG
GAGTACGGATAAAATGCTTGATGGTCGGAAGAGGCATAAATTCCGTCAGCCAGT
TTAGTCTGACCATCTCATCTGTAACATCATTGGCAACGCTACCTTTGCCATGTTTC
AGAAACAACTCTGGCGCATCGGGCTTCCCATACAATCGATAGATTGTCGCACCTG
ATTGCCCGACATTATCGCGAGCCCATTTATACCCATATAAATCAGCATCCATGTT
GGAATTTAATCGCGGCCTCGAGCAAGACGTTTCCCGTTGAATATGGCTCATAACA
CCCCTTGTATTACTGTTTATGTAAGCAGACAGTTTTATTGTTCATGACCAAAATCC
CTTAACGTGAGTTTTCGTTCCACTGAGCGTCAGACCCCGTAGAAAAGATCAAAGG
ATCTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTTCC
GAAGGTAACTGGCTTCAGCAGAGCGCAGATACCAAATACTGTCCTTCTAGTGTA
GCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGAACGG
GGGGTTCGTGCACACAGCCCAGCTTGGAGCGAACGACCTACACCGAACTGAGAT
ACCTACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGAC
TTGAGCGTCGATTTTTGTGATGCTCGTCAGGGGGCGGAGCCTATGGAAAAACG
CCAGCAACGCGGCCTTTTTACGGTTCCTGGCCTTTTGCTGGCCTTTTGCTCACATG
TTCTTTCCTGCGTTATCCCCTGATTCTGTGGATAACCGTATTACCGCCTTTGAGTG
AGCTGATACCGCTCGCCGCAGCCGAACGACCGAGCGCAGCGAGTCAGTGAGCGA
GGAAGCGGAAGAGCGCCTGATGCGGTATTTTCTCCTTACGCATCTGTGCGGTATT
TCACACCGCATATATGGTGCACTCTCAGTACAATCTGCTCTGATGCCGCATAGTT
AAGCCAGTATACACTCCGCTATCGCTACGTGACTGGGTCATGGCTGCGCCCCGAC
ACCCGCCAACACCCGCTGACGCGCCCTGACGGGCTTGTCTGCTCCCGGCATCCGC
TTACAGACAAGCTGTGACCGTCTCCGGGAGCTGCATGTGTCAGAGGTTTTCACCG
TCATCACCGAAACGCGCGAGGCAGCTGCGGTAAAGCTCATCAGCGTGGTCGTGA
AGCGATTCACAGATGTCTGCCTGTTCATCCGCGTCCAGCTCGTTGAGTTTCTCCA
GAAGCGTTAATGTCTGGCTTCTGATAAAGCGGGCCATGTTAAGGGCGGTTTTTTC
CTGTTTGGTCACTGATGCCTCCGTGTAAGGGGGATTTCTGTTCATGGGGGTAATG
ATACCGATGAAACGAGAGAGGATGCTCACGATACGGGTTACTGATGATGAACAT
GCCCGGTTACTGGAACGTTGTGAGGGTAAACAACTGGCGGTATGGATGCGGCGG
GACCAGAGAAAAATCACTCAGGGTCAATGCCAGCGCTTCGTTAATACAGATGTA
GGTGTTCCACAGGGTAGCCAGCAGCATCCTGCGATGCAGATCCGGAACATAATG
GTGCAGGGCGCTGACTTCCGCGTTTCCAGACTTTACGAAACACGGAAACCGAAG

FIGURE 2 (CONT'D)

pET2P7K32 (SEQ ID NO. 2) (Cont'd)

ACCATTCATGTTGTTGCTCAGGTCGCAGACGTTTTGCAGCAGCAGTCGCTTCACG
TTCGCTCGCGTATCGGTGATTCATTCTGCTAACCAGTAAGGCAACCCCGCCAGCC
TAGCCGGGTCCTCAACGACAGGAGCACGATCATGCGCACCCGTGGCCAGGACCC
AACGCTGCCCGAGATGCGCCGCGTGCGGCTGCTGGAGATGGCGGACGCGATGGA
TATGTTCTGCCAAGGGTTGGTTTGCGCATTCACAGTTCTCCGCAAGAATTGATTG
GCTCCAATTCTTGGAGTGGTGAATCCGTTAGCGAGGTGCCGCCGGCTTCCATTCA
GGTCGAGGTGGCCCGGCTCCATGCACCGCGACGCAACGCGGGGAGGCAGACAA
GGTATAGGGCGGCGCCTACAATCCATGCCAACCCGTTCCATGTGCTCGCCGAGGC
GGCATAAATCGCCGTGACGATCAGCGGTCCAGTGATCGAAGTTAGGCTGGTAAG
AGCCGCGAGCGATCCTTGAAGCTGTCCTGATGGTCGTCATCTACCTGCCTGGAC
AGCATGGCCTGCAACGCGGGCATCCCGATGCCGCCGGAAGCGAGAAGAATCATA
ATGGGGAAGGCCATCCAGCCTCGCGTCGCGAACGCCAGCAAGACGTAGCCCAGC
GCGTCGGCCGCCATGCCGGCGATAATGGCCTGCTTCTCGCCGAAACGTTTGGTGG
CGGGACCAGTGACGAAGGCTTGAGCGAGGGCGTGCAAGATTCCGAATACCGCAA
GCGACAGGCCGATCATCGTCGCGCTCCAGCGAAAGCGGTCCTCGCCGAAAATGA
CCCAGAGCGCTGCCGGCACCTGTCCTACGAGTTGCATGATAAAGAAGACAGTCA
TAAGTGCGGCGACGATAGTCATGCCCCGCGCCCACCGGAAGGAGCTGACTGGGT
TGAAGGCTCTCAAGGGCATCGGCTCTCCCTTATGCGACTCCTGCATTAGGAAGCA
GCCCAGTAGTAGGTTGAGGCCGTTGAGCACCGCCGCCGCAAGGAATGGTGCATG
CAAGGAGATGGCCAAAACCATCGTTCTTTCGGTCGGCGAGGCTACTCGCACTCTG
ACTGAGATCCAGTCCACCGCAGACCGTCAGATCTTCGAAGAGAAGGTCGGGCCT
CTGGTGGGTCGGCTGCGCCTCACGGCTTCGCTCCGTCAAAACGGAGCCAAGACC
GCGTATCGCGTCAACCTAAAACTGGATCAGGCGGACGTCGTTGATTGCTCCACCA
GCGTCTGCGGCGAGCTTCCGAAAGTGCGCTACACTCAGGTATGGTCGCACGACG
TGACAATCGTTGCGAATAGCACCGAGGCCTCGCGCAAATCGTTGTACGATTTGAC
CAAGTCCCTCGTCGCGACCTCGCAGGTCGAAGATCTTGTCGTCAACCTTGTGCCG
CTGGGCCGTGCTAGCTCCAAAACCATCGTTCTTTCGGTCGGTACCGAGGCTACTC
GCACTCTGACTGAGATCCAGTCCACCGCAGACCGTCAGATCTTCGAAGAGAAGG
TCGGGCCTCTGGTGGGTCGGCTGCGCCTCACGGCTTCGCTCCGTCAAAACGGAGC
CAAGACCGCGTATCGCGTCAACCTAAAACTGGATCAGGCGGACGTCGTTGATTG
CTCCACCAGCGTCTGCGGCGAGCTTCCGAAAGTGCGCTACACTCAGGTATGGTCG
CACGACGTGACAATCGTTGCGAATAGCACCGAGGCCTCGCGCAAATCGTTGTAC
GATTTGACCAAGTCCCTCGTCGCGACCTCGCAGGTTGAAGATCTTGTCGTCAACC
TTGTGCCGCTGGGCCGTAATAGACGCCGGGTTAATTAATTAAGGATCCGGCTGCT
AACAAAGCCCGAAAGGAAGCTGAGTTGGCTGCTGCCACCGCTGAGCAATAACTA
GCATAACCCCTTGGGGCCTCTAAACGGGTCTTGAGGGGTTTTTTGCTGAAAGGAG
GAACTATATCCGGATATCCACAGGACGGGTGTGGTCGCCATGATCGCGTAGTCG
ATAGTGGCTCCAAGTAGCGAAGCGAGCAGGACTGGGCGGCGGCCAAAGCGGTC
GGACAGTGCTCCGAGAACGGGTGCGCATAGAAATTGCATCAACGCATATAGCGC
TAGCAGCACGCCATAGTGACTGGCGATGCTGTCGGAATGGACGATATCCCGCAA
GAGGCCCGGCAGTACCGGCATAACCAAGCCTATGCCTACAGCATCCAGGGTGAC
GGTGCCGAGGATGACGATGAGCGCATTGTTAGATTTCATACACGGTGCCTGACTG
CGTTAGCAATTTAACTGTGATAAACTACCGCATTAAAGCTTATCGATGATAAGCT
GTCAAACATGAA

FIGURE 3

Nucleotide and amino acid sequences of the AB-loop of wild-type PP7 coat protein and the L2-PP7 recombinants p2P7K32 downstream coat protein sequence (*KpnI site in italics*) (SEQ ID No. 3):

```
 1   2   3   4   5   6   7   8   9  10  11  12  13  14  15  16  17  18
ATGGCCAAAACCATCGTTCTTTCGGTCGGTACCGCTACTCGCACTCTGACTGAG
 M   A   K   T   I   V   L   S   V   G   T   A   T   R   T   L   T   E
```

Specific peptide insertions were constructed using the following primers
(*KpnI site in italics*, insertion in bold):

HPV16 L2 peptide (SEQ ID No. 4)
```
GCC GGTACC CAGCTGTATAAAACCTGCAAACAGGCGGGCACCTGCCCGCCGGAT GAGGCTACTCGCACTCTGACTGAG
 G   T    Q  L  Y  K  T  C  K  Q  A  G  T  C  P  P  D    E  A  T  R  T  L  T  E
```

HPV45 (and HPV 39) L2 peptide (SEQ ID No. 5)
```
GCC GGTACC GATCTGTATCGCACCTGCAAACAGAGCGGCACCTGCCCGCCGGAT GAGGCTACTCGCACTCTGACTGAG
 G   T    D  L  Y  R  T  C  K  Q  S  G  T  C  P  P  D    E  A  T  R  T  L  T  E
```

HPV58 (and HPV 52) L2 peptide (SEQ ID No. 6)
```
GCC GGTACC CAGCTGTATCAGACCTGCAAAGCGAGCGGCACCTGCCCGCCGGAT GAGGCTACTCGCACTCTGACTGAG
 G   T    Q  L  Y  Q  T  C  K  A  S  G  T  C  P  P  D    E  A  T  R  T  L  T  E
```

HPV1 L2 peptide (SEQ ID No. 7)

```
GGCTC GGTACC gatatttatccgagctgcaaaattagcaatacctgcccgccggat GAGGCT
   G    T    D  I  Y  P  S  C  K  I  S  N  T  C  P  P  D   E  A
```

HPV5 (and HPV 8) L2 peptide (SEQ ID No. 8)

```
GGCTC GGTACC catatttatcagacctgcaaacaggcgggcacctgcccgccggat GAGGCT
   G    T    H  I  Y  Q  T  C  K  Q  A  G  T  C  P  P  D   E  A
```

HPV6 L2 peptide (SEQ ID No. 9)

```
GGCTC GGTACC cagctgtatcagacctgcaaactgaccggcacctgcccgccggat GAGGCT
   G    T    Q  L  Y  Q  T  C  K  L  T  G  T  C  P  P  D   E  A
```

FIGURE 3 (Cont'd)

HPV11 (and HPV 33) L2 peptide (SEQ ID No. 10)

GGCTC*GGTACC*cagctgtatcagacctgcaaagcgaccggcacctgcccgccggatGAGGCT
     *G*  *T*  Q  L  Y  Q  T  C  K  A  T  G  T  C  P  P  D  E  A HPV18 L2 peptide (SEQ ID No. 11)

GGCTC*GGTACC*gatctgtataaaacctgcaaacagagcggcacctgcccgccggatGAGGCT
           G  T  D  L  Y  K  T  C  K  Q  S  G  T  C  P  P  D  E  A

FIGURE 4

Amino acid Sequence of L2 (17-31, or equivalent) from selected HPV types cloned into the PP7 coat protein of Agarose gel electrophoresis of VLPs Lane 1 Purified wild-type single-chain dimer VLP Lane 2  16L2 VLP Lane 3  45L2 VLP Lane 4  58L2 VLP Variations in electrophoretic mobility reflect charge differences conferred by the inserted peptides FIGURE 6
A.
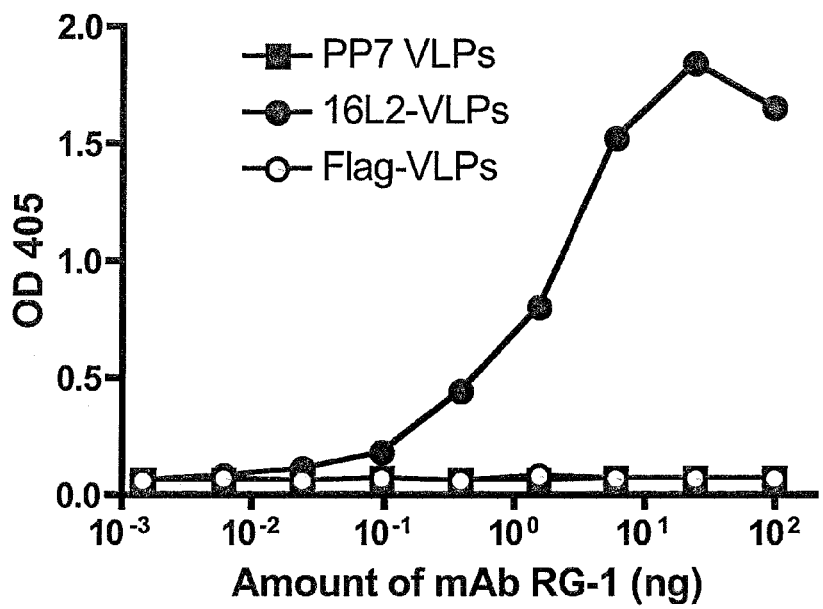
B.
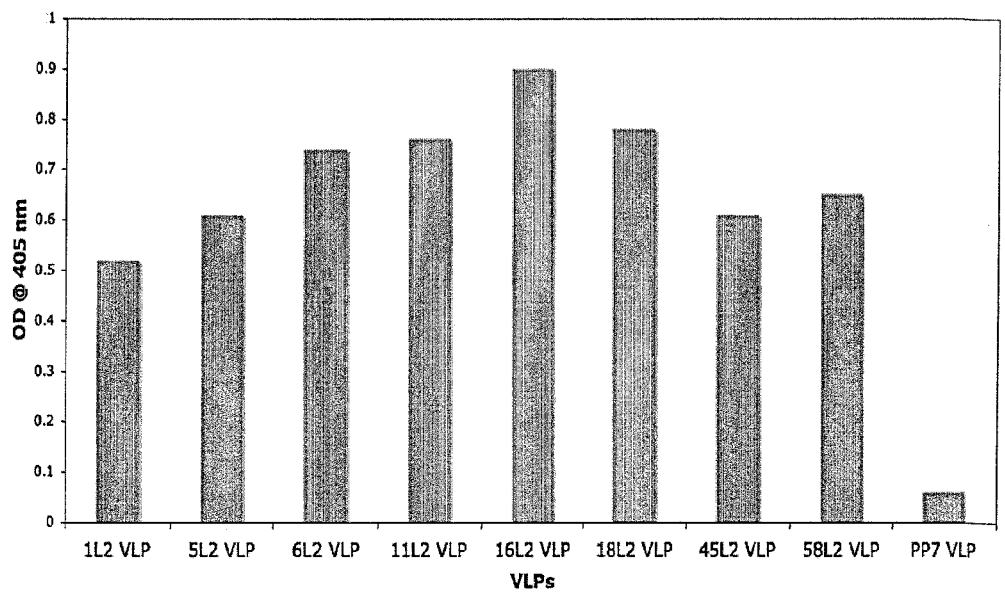

Reactivity of sera from L2-VLP immunized mice with HPV L2 peptides

FIGURE 12
A. Homologous Neutralization (PsV16)
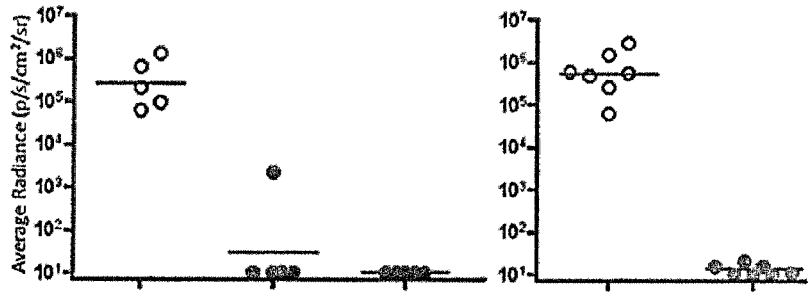
B. Heterologous Neutralization
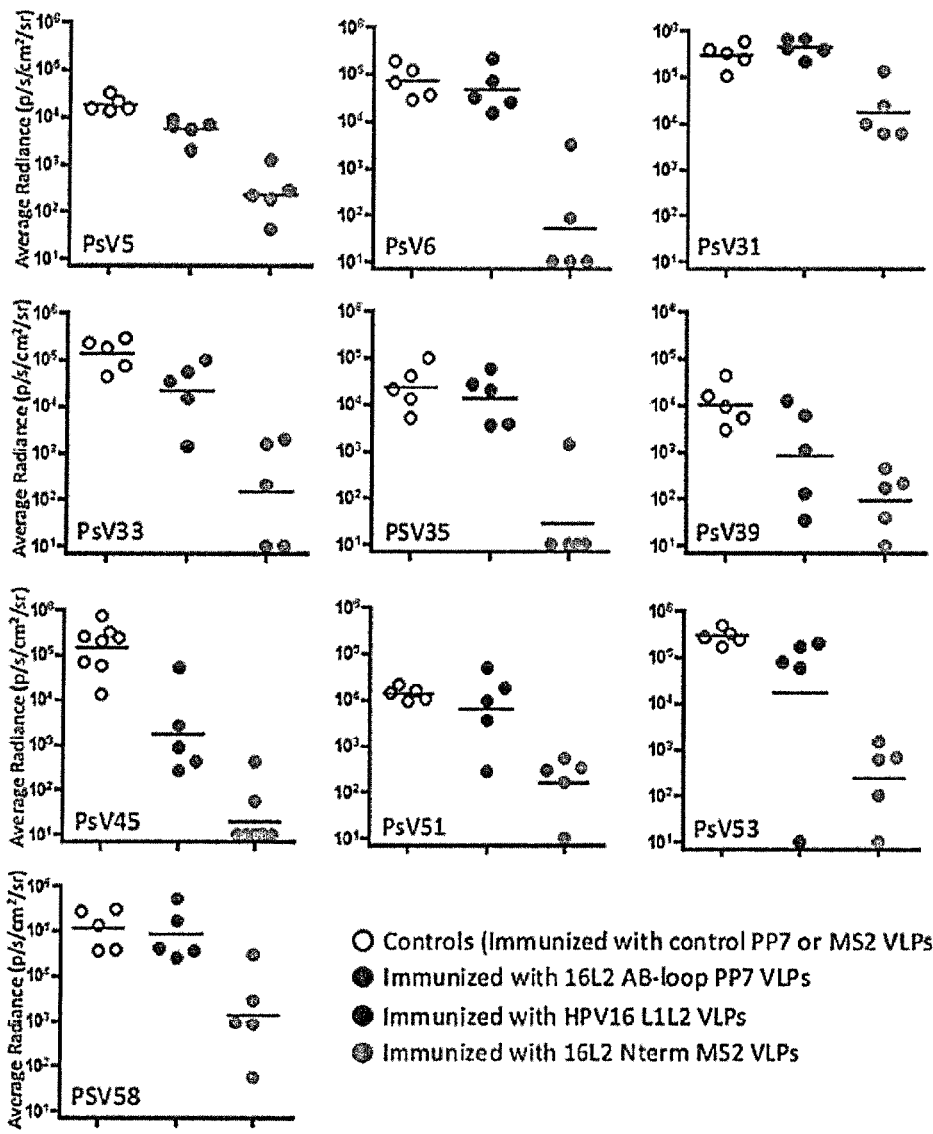
○ Controls (Immunized with control PP7 or MS2 VLPs)
● Immunized with 16L2 AB-loop PP7 VLPs
● Immunized with HPV16 L1L2 VLPs
● Immunized with 16L2 Nterm MS2 VLPs

FIGURE 13

Primer Sequences:

HPV16 L2 (14-40): (SEQ ID NO:35)
GC G*CC* A*TG* GCA AGC GCG ACC CAG CTG TAT AAA ACC TGC AAA CAG GCG
GGC ACC TGC CCG CCG GAT ATT ATT CCG AAA GTG GAA GGC AAA ACC
TCA *GGA GGA AGC* GCA AGC AAT TTC ACG CAA TTT

HPV16 L2 (17-31) (SEQ ID NO:36)
GC G*CC* A*TG* GCA CAG CTG TAT AAA ACC TGC AAA CAG GCG GGC ACC TGC
CCG CCG GAT *TCA ACC GGA GTT GGA AGC* GCA AGC AAT TTC ACG CAA TTT G

HPV16L2 (20-29) (SEQ ID NO:37)
GC G*CC* A*TG* GCA AAA ACC TGC AAA CAG GCG GGC ACC TGC CCG *TCA ACC
GGA GTT GGA AGC* GCA AGC AAT TTC ACG CAA TTT G

Amino acid Sequences of the N-terminal domain of the recombinant MS2 constructs:

HPV16 L2 (14-40): (SEQ ID NO:38)
Met A S A T Q L Y K T C K Q A G T C P P D I I P K V E G K T *S G G S* A S N F T Q F

HPV16 L2 (17-31) (SEQ ID NO:39)
Met A Q L Y K T C K Q A G T C P P D *S T G V G S* A S N F T Q F

HPV16L2 (20-29) (SEQ ID NO:40)
Met A K T C K Q A G T C P *S T G V G S* A S N F T Q F

Bacteriophage VLPs displaying an HPV16 L2 peptide induce high-titer antibody responses Mice were immunized i.m. with 5 μg of VLPs without exogenous adjuvant. Shown are end-point dilution ELISA titers against an HPV16 L2 (14-40) peptide after *one* or *two* immunizations.

FIGURE 19
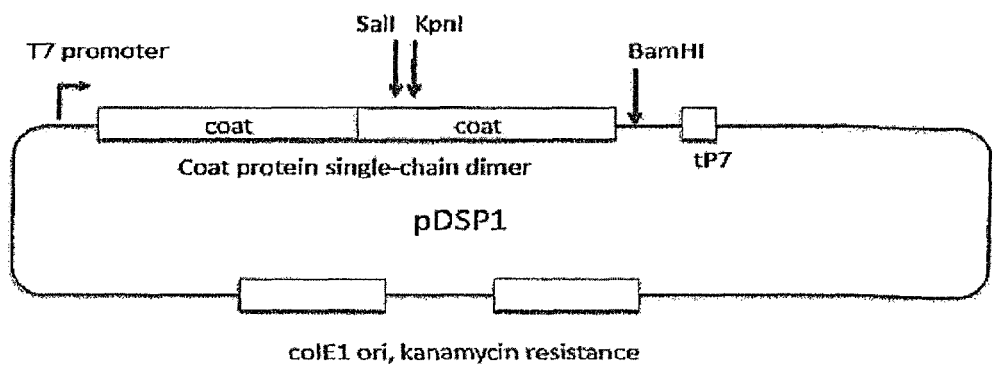
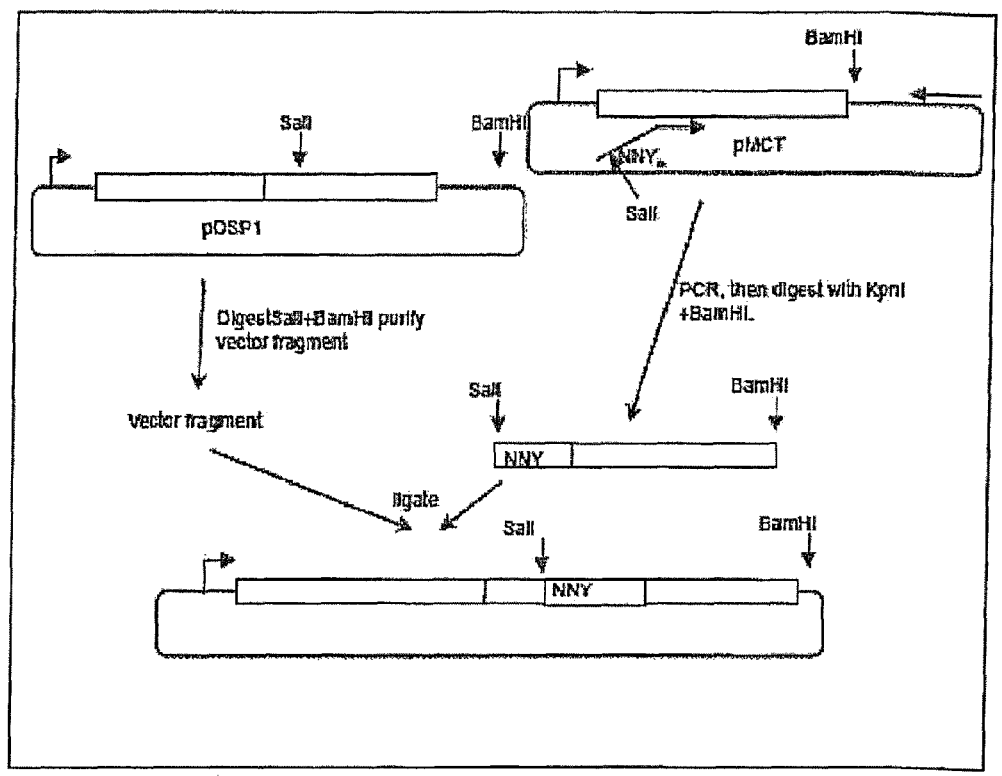

FIGURE 20
Summary of *in vivo* HPV PsV challenge experiments

| | 16L2(17-31) AB-loop PP7 VLPs | | 16L2(17-31) Nterm MS2 VLPs | |
|---|---|---|---|---|
| HPV PsV | *Fold reduction | P-value | *Fold reduction | P-value |
| 16 | 6263 | <0.0001 | 68228 | <0.0001 |
| 5 | 3.4 | 0.002 | 80 | <0.0001 |
| 6 | 1.5 | 0.24 | 1430 | 0.0001 |
| 31 | 0.65 | 0.14 | 17 | 0.0011 |
| 33 | 6.4 | 0.028 | 910 | 0.0003 |
| 35 | 1.7 | 0.25 | 840 | 0.0002 |
| 39 | 12 | 0.037 | 110 | 0.0002 |
| 45 | 84 | 0.0003 | 7190 | <0.0001 |
| 51 | 2.2 | 0.19 | 88 | 0.0001 |
| 53 | 16 | 0.088 | 1240 | <0.0001 |
| 58 | 1.35 | 0.35 | 86 | 0.002 |

\* Fold reduction in geometric mean radiance compared to control mice immunized with mixed MS2/PP7 VLPs. Bold values indicate that the reduction in luminescence was statistically significant ($p<0.01$).

SEQUENCE LISTING

```
<160> NUMBER OF SEQ ID NOS: 34

<210> SEQ ID NO 1
<211> LENGTH: 4003
<212> TYPE: DNA
<213> ORGANISM: Artificial Sequence
<220> FEATURE:
<223> OTHER INFORMATION: plasmid p2P7K32

<400> SEQUENCE: 1
gacgaaaggg  cctcgtgata  cgcctatttt  tataggttaa  tgtcatgata  ataatggttt      60
cttagacgtc  aggtggcact  tttcggggaa  atgtgcgcgg  aaccccctatt  tgtttatttt    120 tctaaataca  ttcaaatatg  tatccgctca  tgagacaata  accctgataa  atgcttcaat    180
aatattgaaa  aaggaagagt  atgagtattc  aacatttccg  tgtcgccctt  attccctttt    240
```

```
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattacg ccgggcaaga gcaactcggt cgccgcatac     480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga    1140 tccttttga taatctcatg accaaaatcc cttaacgtga gttttcgttc cactgagcgt    1200
cagaccccgt agaaaagatc aaaggatctt cttgagatcc ttttttctg cgcgtaatct    1260 gctgcttgca acaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag     1800 gggggcggag cctatggaaa aacgccagca acgcggcctt tttacggttc ctggccttt     1860 gctggccttt tgctcacatg ttcttcctg cgttatcccc tgattctgtg gataaccgta     1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg ataacaatt tcacacagga aacagctatg     2220
accatgatta cgccaagctt gcatgcctgc aggtcgactc tagatagagc cctcaaccgg    2280
agtttgaagc atggccaaaa ccatcgttct ttcggtcgcg aggctactcg cactctgact    2340
gagatccagt ccaccgcaga ccgtcagatc ttcgaagaga aggtcgggcc tctggtgggt    2400
cggctgcgcc tcacggcttc gctccgtcaa acggagcca agaccgcgta tcgcgtcaac      2460
ctaaaactgg atcaggcgga cgtcgttgat tgctccacca cgtctgcggc gagcttccg     2520 aaagtgcgct acactcaggt atggtcgcac gacgtgacaa tcgttgcgaa tagcaccgag    2580
```

```
gcctcgcgca aatcgttgta cgatttgacc aagtccctcg tcgcgacctc gcaggtcgaa    2640
gatcttgtcg tcaaccttgt gccgctgggc cgtgctagct ccaaaaccat cgttctttcg    2700
gtcggtaccg aggctactcg cactctgact gagatccagt ccaccgcaga ccgtcagatc    2760
ttcgaagaga aggtcgggcc tctggtgggt cggctgcgcc tcacggcttc gctccgtcaa    2820
aacggagcca agaccgcgta tcgcgtcaac ctaaaactgg atcaggcgga cgtcgttgat    2880
tgctccacca gcgtctgcgg cgagcttccg aaagtgcgct acactcaggt atggtcgcac    2940
gacgtgacaa tcgttgcgaa tagcaccgag gcctcgcgca aatcgttgta cgatttgacc    3000
aagtccctcg tcgcgacctc gcaggttgaa gatcttgtcg tcaaccttgt gccgctgggc    3060
cgtaatagac gccggccatt caaacatgag gattacccat gtcgaagaca caaagaagt    3120
tcggatccaa ttcactggcc gtcgttttac aacgtcgtga ctgggaaaac cctggcgtta    3180
cccaacttaa tcgccttgca gcacatcccc cttttcgccat ctggcgtaat agcgaagagg    3240
cccgcaccga tcgcccttcc caacagttgc gcagcctgaa tggcgaatgg cgcctgatgc    3300
ggtattttct ccttacgcat ctgtgcggta tttcacaccg catacgtcaa gcaaccata    3360
gtacgcgccc tgtagcggcg cattaagcgc ggcgggtgtg gtggttacgc gcagcgtgac    3420
cgctacactt gccagcgccc tagcgcccgc tcctttcgct ttcttccctt cctttctcgc    3480
cacgttcgcc ggctttcccc gtcaagctct aaatcggggg ctccctttag ggttccgatt    3540
tagtgcttta cggcacctcg accccaaaaa cttgatttgg gtgatggttc acgtagtggg    3600
ccatcgccct gatagacggt ttttcgccct ttgacgttgg agtccacgtt ctttaatagt    3660
ggactcttgt tccaaactgg aacaacactc aaccctatct cgggctattc ttttgattta    3720
taagggattt tgccgatttc ggcctattgg ttaaaaaatg agctgattta acaaaaattt    3780
aacgcgaatt ttaacaaaat attaacgttt acaattttat ggtgcactct cagtacaatc    3840
tgctctgatg ccgcatagtt aagccagccc cgacacccgc caacacccgc tgacgcgccc    3900
tgacgggctt gtctgctccc ggcatccgct tacagacaag ctgtgaccgt ctccgggagc    3960
tgcatgtgtc agaggttttc accgtcatca ccgaaacgcg cga                      4003
```

<210> SEQ ID NO 2
<211> LENGTH: 4815
<212> TYPE: DNA
<213> ORGANISM: Artificial Sequence
<220> FEATURE:
<223> OTHER INFORMATION: plasmid pET2P7K32

<400> SEQUENCE: 2

```
ttcttagaaa aactcatcga gcatcaaatg aaactgcaat ttattcatat caggattatc      60
ataccatat ttttgaaaaa gccgtttctg taatgaagga gaaaactcac cgaggcagtt     120
ccataggatg gcaagatcct ggtatcggtc tgcgattccg actcgtccaa catcaataca     180
acctattaat ttcccctcgt caaaaataag gttatcaagt gagaaatcac catgagtgac     240
gactgaatcc ggtgagaatg gcaaaagctt atgcatttct ttccagactt gttcaacagg     300
ccagccatta cgctcgtcat caaaatcact cgcatcaacc aaaccgttat tcattcgtga     360
ttgcgcctga gcgagacgaa atacgcgatc gctgttaaaa ggacaattac aaacaggaat     420
cgaatgcaac cggcgcagga acactgccag cgcatcaaca atattttcac ctgaatcagg     480
atattcttct aatacctgga atgctgtttt cccggggatc gcagtggtga gtaaccatgc     540
atcatcagga gtacggataa aatgcttgat ggtcggaaga ggcataaatt ccgtcagcca     600
gtttagtctg accatctcat ctgtaacatc attggcaacg ctacctttgc catgtttcag     660
```

```
aaacaactct ggcgcatcgg gcttcccata caatcgatag attgtcgcac ctgattgccc    720
gacattatcg cgagcccatt tatacccata taaatcagca tccatgttgg aatttaatcg    780
cggcctcgag caagacgttt cccgttgaat atggctcata acaccccttg tattactgtt    840
tatgtaagca gacagtttta ttgttcatga ccaaaatccc ttaacgtgag ttttcgttcc    900
actgagcgtc agaccccgta gaaaagatca aaggatcttc ttgagatcct ttttttctgc    960
gcgtaatctg ctgcttgcaa acaaaaaaac caccgctacc agcggtggtt tgtttgccgg   1020
atcaagagct accaactctt tttccgaagg taactggctt cagcagagcg cagataccaa   1080
atactgtcct tctagtgtag ccgtagttag gccaccactt caagaactct gtagcaccgc   1140
ctacatacct cgctctgcta atcctgttac cagtggctgc tgccagtggc gataagtcgt   1200
gtcttaccgg gttggactca agacgatagt taccggataa ggcgcagcgg tcgggctgaa   1260
cggggggttc gtgcacacag cccagcttgg agcgaacgac ctacaccgaa ctgagatacc   1320
tacagcgtga gctatgagaa agcgccacgc ttcccgaagg agaaaggcg gacaggtatc    1380 cggtaagcgg cagggtcgga acaggagagc gcacgaggga gcttccaggg ggaaacgcct   1440
ggtatcttta tagtcctgtc gggtttcgcc acctctgact tgagcgtcga ttttgtgat    1500 gctcgtcagg ggggcggagc ctatggaaaa acgccagcaa cgcggccttt ttacggttcc    1560
tggccttttg ctggcctttt gctcacatgt tctttcctgc gttatcccct gattctgtgg   1620
ataaccgtat taccgccttt gagtgagctg ataccgctcg ccgcagccga acgaccgagc   1680
gcagcgagtc agtgagcgag gaagcggaag agcgcctgat gcggtatttt ctccttacgc   1740
atctgtgcgg tatttcacac cgcatatatg gtgcactctc agtacaatct gctctgatgc   1800
cgcatagtta agccagtata cactccgcta tcgctacgtg actgggtcat ggctgcgccc   1860
cgacacccgc caacacccgc tgacgcgccc tgacgggctt gtctgctccc ggcatccgct   1920
tacagacaag ctgtgaccgt ctccgggagc tgcatgtgtc agaggttttc accgtcatca   1980
ccgaaacgcg cgaggcagct gcggtaaagc tcatcagcgt ggtcgtgaag cgattcacag   2040
atgtctgcct gttcatccgc gtccagctcg ttgagtttct ccagaagcgt taatgtctgg   2100
cttctgataa agcgggccat gttaagggcg ttttttcct gtttggtcac tgatgcctcc    2160
gtgtaagggg gatttctgtt catggggta atgataccga tgaaacgaga gaggatgctc    2220
acgatacggg ttactgatga tgaacatgcc cggttactgg aacgttgtga gggtaaacaa   2280
ctggcggtat ggatgcggcg ggaccagaga aaaatcactc agggtcaatg ccagcgcttc   2340
gttaatacag atgtaggtgt tccacagggt agccagcagc atcctgcgat gcagatccgg   2400
aacataatgg tgcagggcgc tgacttccgc gtttccagac tttacgaaac acggaaaccg   2460
aagaccattc atgttgttgc tcaggtcgca gacgttttgc agcagcagtc gcttcacgtt   2520
cgctcgcgta tcggtgattc attctgctaa ccagtaaggc aaccccgcca gcctagccgg   2580
gtcctcaacg acaggagcac gatcatgcgc acccgtggcc aggacccaac gctgcccgag   2640
atgcgccgcg tgcggctgct ggagatggcg gacgcgatgg atatgttctg ccaagggttg   2700
gtttgcgcat tcacagttct ccgcaagaat tgattggctc caattcttgg agtggtgaat   2760
ccgttagcga ggtgccgccg gcttccattc aggtcgaggt ggcccggctc catgcaccgc   2820
gacgcaacgc ggggaggcag acaaggtata gggcggcgcc tacaatccat gccaacccgt   2880
tccatgtgct cgccgaggcg gcataaatcg ccgtgacgat cagcggtcca gtgatcgaag   2940
ttaggctggt aagagccgcg agcgatcctt gaagctgtcc ctgatggtcg tcatctacct   3000
```

```
gcctggacag catggcctgc aacgcgggca tcccgatgcc gccggaagcg agaagaatca    3060
taatggggaa ggccatccag cctcgcgtcg cgaacgccag caagacgtag cccagcgcgt    3120
cggccgccat gccggcgata atggcctgct tctcgccgaa acgtttggtg gcgggaccag    3180
tgacgaaggc ttgagcgagg gcgtgcaaga ttccgaatac cgcaagcgac aggccgatca    3240
tcgtcgcgct ccagcgaaag cggtcctcgc cgaaaatgac ccagagcgct gccggcacct    3300
gtcctacgag ttgcatgata agaagacag tcataagtgc ggcgacgata gtcatgcccc     3360
gcgcccaccg gaaggagctg actgggttga aggctctcaa gggcatcggc tctcccttat    3420
gcgactcctg cattaggaag cagcccagta gtaggttgag gccgttgagc accgccgccg    3480
caaggaatgg tgcatgcaag gagatggcca aaaccatcgt tctttcggtc ggcgaggcta    3540
ctcgcactct gactgagatc cagtccaccg cagaccgtca gatcttcgaa gagaaggtcg    3600
ggcctctggt gggtcggctg cgcctcacgg cttcgctccg tcaaaacgga gccaagaccg    3660
cgtatcgcgt caacctaaaa ctggatcagg cggacgtcgt tgattgctcc accagcgtct    3720
gcggcgagct tccgaaagtg cgctacactc aggtatggtc gcacgacgtg acaatcgttg    3780
cgaatagcac cgaggcctcg cgcaaatcgt tgtacgattt gaccaagtcc ctcgtcgcga    3840
cctcgcaggt cgaagatctt gtcgtcaacc ttgtgccgct gggccgtgct agctccaaaa    3900
ccatcgttct ttcggtcggt accgaggcta ctcgcactct gactgagatc cagtccaccg    3960
cagaccgtca gatcttcgaa gagaaggtcg ggcctctggt gggtcggctg cgcctcacgg    4020
cttcgctccg tcaaaacgga gccaagaccg cgtatcgcgt caacctaaaa ctggatcagg    4080
cggacgtcgt tgattgctcc accagcgtct gcggcgagct tccgaaagtg cgctacactc    4140
aggtatggtc gcacgacgtg acaatcgttg cgaatagcac cgaggcctcg cgcaaatcgt    4200
tgtacgattt gaccaagtcc ctcgtcgcga cctcgcaggt tgaagatctt gtcgtcaacc    4260
ttgtgccgct gggccgtaat agacgccggg ttaattaatt aaggatccgg ctgctaacaa    4320
agcccgaaag gaagctgagt tggctgctgc caccgctgag caataactag cataaccct    4380 tggggcctct aaacgggtct tgaggggttt tttgctgaaa ggaggaacta tatccggata    4440
tccacaggac gggtgtggtc gccatgatcg cgtagtcgat agtggctcca agtagcgaag    4500
cgagcaggac tgggcggcgg ccaaagcggt cggacagtgc tccgagaacg ggtgcgcata    4560
gaaattgcat caacgcatat agcgctagca gcacgccata gtgactggcg atgctgtcgg    4620
aatggacgat atcccgcaag aggcccggca gtaccggcat aaccaagcct atgcctacag    4680
catccagggt gacggtgccg aggatgacga tgagcgcatt gttagatttc atacacggtg    4740
cctgactgcg ttagcaattt aactgtgata aactaccgca ttaaagctta tcgatgataa    4800
gctgtcaaac atgaa                                                    4815

<210> SEQ ID NO 3
<211> LENGTH: 54
<212> TYPE: DNA
<213> ORGANISM: Artificial Sequence
<220> FEATURE:
<223> OTHER INFORMATION: p2P7K32  downstream coat protein sequence.

<400> SEQUENCE: 3
atggccaaaa ccatcgttct ttcggtcggt accgctactc gcactctgac tgag          54

<210> SEQ ID NO 4
<211> LENGTH: 78
<212> TYPE: DNA
<213> ORGANISM: Artificial Sequence
```

```
<220> FEATURE:
<223> OTHER INFORMATION: HPV16 L2 peptide

<400> SEQUENCE: 4
gccggtaccc agctgtataa aacctgcaaa caggcgggca cctgcccgcc ggatgaggct    60
actcgcactc tgactgag                                                  78

<210> SEQ ID NO 5
<211> LENGTH: 78
<212> TYPE: DNA
<213> ORGANISM: Artificial Sequence
<220> FEATURE:
<223> OTHER INFORMATION: HPV45 (and HPV39) L2 peptide

<400> SEQUENCE: 5
gccggtaccg atctgtatcg cacctgcaaa cagagcggca cctgcccgcc ggatgaggct    60
actcgcactc tgactgag                                                  78

<210> SEQ ID NO 6
<211> LENGTH: 78
<212> TYPE: DNA
<213> ORGANISM: Artificial Sequence
<220> FEATURE:
<223> OTHER INFORMATION: HPV58 (and HPV52) L2 peptide

<400> SEQUENCE: 6
gccggtaccc agctgtatca gacctgcaaa gcgagcggca cctgcccgcc ggatgaggct    60
actcgcactc tgactgag                                                  78

<210> SEQ ID NO 7
<211> LENGTH: 62
<212> TYPE: DNA
<213> ORGANISM: Artificial Sequence
<220> FEATURE:
<223> OTHER INFORMATION: HPV1 L2 peptide

<400> SEQUENCE: 7
ggctcggtac cgatatttat ccgagctgca aaattagcaa tacctgcccg ccggatgagg    60
ct                                                                   62

<210> SEQ ID NO 8
<211> LENGTH: 62
<212> TYPE: DNA
<213> ORGANISM: Artificial Sequence
<220> FEATURE:
<223> OTHER INFORMATION: HPV5 (and HPV8) L2 peptide

<400> SEQUENCE: 8
ggctcggtac ccatatttat cagacctgca aacaggcggg cacctgcccg ccggatgagg    60
ct                                                                   62

<210> SEQ ID NO 9
<211> LENGTH: 62
<212> TYPE: DNA
<213> ORGANISM: Artificial Sequence
<220> FEATURE:
<223> OTHER INFORMATION: HPV6 L2 peptide

<400> SEQUENCE: 9
ggctcggtac ccagctgtat cagacctgca aactgaccgg cacctgcccg ccggatgagg    60
ct                                                                   62
```

```
<210> SEQ ID NO 10
<211> LENGTH: 62
<212> TYPE: DNA
<213> ORGANISM: Artificial Sequence
<220> FEATURE:
<223> OTHER INFORMATION: HPV11 (and HPV 33) L2 peptide

<400> SEQUENCE: 10
ggctcggtac ccagctgtat cagacctgca aagcgaccgg cacctgcccg ccggatgagg      60
ct                                                                    62

<210> SEQ ID NO 11
<211> LENGTH: 62
<212> TYPE: DNA
<213> ORGANISM: Artificial Sequence
<220> FEATURE:
<223> OTHER INFORMATION: HPV18 L2 peptide

<400> SEQUENCE: 11
ggctcggtac cgatctgtat aaaacctgca acagagcgg cacctgcccg ccggatgagg       60
ct                                                                    62

<210> SEQ ID NO 12
<211> LENGTH: 15
<212> TYPE: PRT
<213> ORGANISM: Artificial Sequence
<220> FEATURE:
<223> OTHER INFORMATION: HPV1

<400> SEQUENCE: 12

Asp Ile Tyr Pro Ser Cys Lys Ile Ser Asn Thr Cys Pro Pro Asp
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: HPV5

<400> SEQUENCE: 13

His Ile Tyr Gln Thr Cys Lys Gln Ala Gly Thr Cys Pro Pro Asp
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: HPV8

<400> SEQUENCE: 14

Asp Ile Tyr Pro Ser Cys Lys Ile Ser Asn Thr Cys Pro Pro Asp
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: HPV16

<400> SEQUENCE: 15

Gln Leu Tyr Lys Thr Cys Lys Gln Ala Gly Thr Cys Pro Pro Asp
1               5                   10                  15
```

```
<210> SEQ ID NO 16
<211> LENGTH: 15
<212> TYPE: PRT
<213> ORGANISM: Artificial Sequence
<220> FEATURE:
<223> OTHER INFORMATION: HPV35

<400> SEQUENCE: 16

Gln Leu Tyr Arg Thr Cys Lys Ala Ala Gly Thr Cys Pro Pro Asp
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: HPV31

<400> SEQUENCE: 17

Gln Leu Tyr Gln Thr Cys Lys Ala Ala Gly Thr Cys Pro Ser Asp
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: HPV33

<400> SEQUENCE: 18

Gln Leu Tyr Gln Thr Cys Lys Ala Thr Gly Thr Cys Pro Pro Asp
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: HPV58

<400> SEQUENCE: 19

Gln Leu Tyr Gln Thr Cys Lys Ala Ser Gly Thr Cys Pro Pro Asp
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: HPV52

<400> SEQUENCE: 20

Gln Leu Tyr Gln Thr Cys Lys Ala Thr Gly Thr Cys Pro Pro Asp
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: HPV73

<400> SEQUENCE: 21

Gln Leu Tyr Lys Thr Cys Lys Gln Ala Gly Thr Cys Pro Pro Asp
 1               5                  10                  15
```

```
<210> SEQ ID NO 22
<211> LENGTH: 15
<212> TYPE: PRT
<213> ORGANISM: Artificial Sequence
<220> FEATURE:
<223> OTHER INFORMATION: HPV6

<400> SEQUENCE: 22

Gln Leu Tyr Gln Thr Cys Lys Leu Thr Gly Thr Cys Pro Pro Asp
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: HPV11

<400> SEQUENCE: 23

Gln Leu Tyr Gln Thr Cys Lys Ala Thr Gly Thr Cys Pro Pro Asp
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: HPV18

<400> SEQUENCE: 24

Asp Leu Tyr Lys Thr Cys Lys Gln Ser Gly Thr Cys Pro Pro Asp
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: HPV45

<400> SEQUENCE: 25

Asp Leu Tyr Lys Thr Cys Lys Gln Ser Gly Thr Cys Pro Pro Asp
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: HPV39

<400> SEQUENCE: 26

Asp Leu Tyr Arg Thr Cys Lys Gln Ser Gly Thr Cys Pro Pro Asp
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: HPV68

<400> SEQUENCE: 27

Glu Leu Tyr Lys Thr Cys Lys Gln Ser Gly Thr Cys Pro Pro Asp
1               5                   10                  15
```

```
<210> SEQ ID NO 28
<211> LENGTH: 15
<212> TYPE: PRT
<213> ORGANISM: Artificial Sequence
<220> FEATURE:
<223> OTHER INFORMATION: HPV59

<400> SEQUENCE: 28

Asp Leu Tyr Lys Thr Cys Lys Gln Ala Gly Thr Cys Pro Ser Asp
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: HPV51

<400> SEQUENCE: 29

Gln Leu Tyr Ser Thr Cys Lys Ala Ala Gly Thr Cys Pro Pro Asp
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: HPV56

<400> SEQUENCE: 30

Gln Leu Tyr Lys Thr Cys Lys Leu Ser Gly Thr Cys Pro Glu Asp
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: HP66

<400> SEQUENCE: 31

Gln Leu Tyr Lys Thr Cys Lys Gln Ser Gly Thr Cys Pro Pro Asp
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: HPV2

<400> SEQUENCE: 32

Asp Leu Tyr Arg Thr Cys Lys Gln Ala Gly Thr Cys Pro Pro Asp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: CRPV

<400> SEQUENCE: 33

Asp Ile Tyr Pro Thr Cys Lys Ile Ala Gly Asn Cys Pro Ala Asp
1               5                   10                  15

<210> SEQ ID NO 34
```

```
<211> LENGTH: 15
<212> TYPE: PRT
<213> ORGANISM: Artificial Sequence
<220> FEATURE:
<223> OTHER INFORMATION: BPV1

<400> SEQUENCE: 34

Asp Leu Tyr Arg Thr Cys Lys Gln Ala Gly Thr Cys Pro Pro Asp
1               5                   10                  15
```

IMMUNOGENIC HPV L2-CONTAINING VLPS AND RELATED COMPOSITIONS, CONSTRUCTS, AND THERAPEUTIC METHODS

CLAIM OF PRIORITY

This application is a continuation-in-part application of U.S. patent application Ser. No. 13/577,484, filed Aug. 7, 2012, which is a §371 of international patent application PCT/US11/024,030, filed Feb. 8, 2011, which claims the benefit of priority of U.S. provisional applications US61/302,836, filed Feb. 9, 2010, entitled "Immunogenic HPV L2-containing VLPs and Related Compositions, Constructs, and Therapeutic Methods", and US61/334,826, filed May 14, 2010, of same title This application is also a continuation in part application of PCT/US2013/020960, filed Jan. 10, 2013 entitled "Immunogenic HPV L-2-Containing VLPs and Related Compositions and Methods" which claims the benefit of priority of U.S. provisional application No. US61/585,839, filed Jan. 12, 2012. All of the preceding patent applications are incorporated by reference in their entirety herein.

GOVERNMENT INTEREST

This patent application was supported by NIH Grant Nos. U19-A108408 and GM042901. The Government has certain rights in the invention.

FIELD OF THE INVENTION

In one aspect, the invention provides immunogenic HPV L2-containing viral-like particles (VLPs). Related compositions (e.g. vaccines), nucleic acid constructs, and therapeutic methods are also provided.

In one aspect, the invention relates generally to virus-like particles and, more specifically, to a platform for peptide display based on VLPs of the RNA bacteriophage PP7.

In certain aspects, the VLPs are comprised of a coat polypeptide of the bacteriophages PP7 or MS2, wherein the coat protein is modified by insertion of peptide antigens derived from HPV L2, the recombinant coat protein is expressed to produce a VLP wherein the HPV L2 peptide is displayed on the surface of the VLP.

In certain aspects, the VLPs are comprised of a coat polypeptide of the bacteriophages PP7 or MS2, wherein the coat protein is modified by insertion of peptide antigens derived from HPV L2, the recombinant coat protein is expressed to produce a VLP wherein the HPV L2 peptide is displayed on the surface of the VLP in an unconstrained conformation.

Immunogenic VLPs and related compositions of the invention induce high titer antibody responses against HPV L2 and protect against HPV challenge in an in vivo animal infection model.

BACKGROUND OF THE INVENTION

Human Papillomavirus (HPV) is the most common sexually transmitted infectious agent worldwide and also is estimated to cause ~500,000 cases of cancer a year (34). HPV infection is also associated with a variety of other diseases, including cutaneous and genital warts. Over 100 different HPV types have been identified, but the most common HPV-associated cancer, cervical cancer, is associated with infection by one of a subset of about 15-18 HPVs termed "high-risk" types. Two of the high-risk types, HPV16 and HPV18, account for approximately 70% of all cases of cervical cancer, and six other high-risk types (types 45, 31, 33, 52, 58, and 35) account for an additional 25% of all cases (33).

Conventional approaches for developing an HPV vaccine were not possible because of the lack of a tissue culture system for robust HPV propagation. However, in the early 1990s it was discovered that the L1 major capsid protein of HPV could self-assemble into virus-like particles (VLPs) that are structurally and antigenically similar to infectious virus (21, 24, 25, 43, 51). HPV VLPs are highly immunogenic; they induce high titer antibody responses upon vaccination of animals and people (44). These results paved the way for the development of the two commercially available STI HPV vaccines. Gardasil®, developed by Merck, contains L1-VLPs derived from two high-risk HPV types (16 and 18) and two low-risk HPVs associated with genital warts (6 and 11). Cervarix®, developed by GlaxoSmithKline, contains HPV16 and 18 L1-VLPs. These vaccines have excellent safety profiles, are highly effective at preventing infection and disease, and appear to induce long-lasting antibody responses (26).

Although some cross-reactivity has been observed between closely related HPV genotypes (46), the protection provided upon vaccination with L1-VLPs is largely HPV type-specific. For example, women who are vaccinated with HPV16 L1-VLPs are completely protected against HPV16-related disease (cervical intraepithelial neoplasia; CIN), but not against disease caused by other high-risk HPV types (26, 31). The type-specific nature of neutralizing antibodies induced by HPV16 L1-VLPs has also been confirmed using in vitro neutralization assays (35, 42). Taking into account the types covered by the current vaccine, and the possibility of some partial cross-protection, it is estimated that with complete vaccine coverage Gardasil® and Cervarix® could provide protection against ~70-80% of cervical cancers. Yet, this figure may be an overestimate; ~50% of infected women are infected with multiple carcinogenic types. Because infection with HPV16 and 18 can cause cancer more rapidly than other high-risk types, co-infection with HPV16 and HPV18 may mask the true risk of cancer caused by other HPV types. Because vaccinated populations are still at risk for cancer the American Cancer Society has recommended that vaccinated women continue to be subjected to Pap screening on an annual basis, at an annual cost of $4-5 billion in the United States alone.

Inducing Broadly Neutralizing Antibodies Against HPV by Targeting the Minor Capsid Protein, L2.

Papillomaviruses encode two capsid proteins, L1 and L2. Upon expression, the major capsid protein, L1, can spontaneously self-assemble into pentamers that further assemble into VLPs, comprised of 360 copies of L1. The minor capsid protein, L2, is not required for VLP formation, but is required for formation of infectious virions (and pseudovirions). Up to 72 copies of L2 can be incorporated in a VLP, and viral infectivity correlates with L2 content (5).

Although neither natural infection nor immunization with L1/L2 VLPs elicits anti-L2 antibody responses, vaccination with bacterially expressed L2 protein, or peptides derived from L2, results in the production of neutralizing antibodies that are protective in animal models (1, 7, 13, 19, 30). The somewhat contradictory data indicating that L2 is poorly immunogenic, yet is the target of highly neutralizing antibodies, can be explained by recent studies that shed light on the role of L2 during viral infection. Structural studies have shown that L2 is poorly exposed on the surface of virions (5). However, it has been proposed that after the virus binds to its primary cellular receptor the capsid undergoes a conformational change that exposes the amino terminus of L2 (15, 45). Once exposed, 12 amino acids at the N-terminus of L2 are cleaved by a cellular protein, furin, exposing one or more L2 neutralizing epitopes, and, it is theorized, allow virions to interact with a cellular coreceptor (15, 39).

Because L2 neutralizing epitopes are not exposed until after HPV binding, normal infection fails to induce anti-L2 neutralizing antibody responses. Thus, there has been little evolutionary pressure for L2 to undergo antigenic variation. Unlike L1-specific neutralizing antibodies, L2-specific neutralizing antibodies are broadly cross-neutralizing (41), suggesting that neutralizing epitopes on L2 are conserved across HPVs and even papillomaviruses (PVs) that infect different species. For example, antisera raised against a peptide representing amino acids 1-88 from bovine papillomavirus type 1 (BPV-1) L2 can cross-neutralize a diverse panel of mucosal and cutaneous HPVs (36). Similarly, vaccination with HPV16 and BPV-1 L2 peptides protects rabbits against challenge with two different rabbit papillomaviruses (19).

In principle, L2 vaccines may be able to overcome the high production cost and type-specific limitations of L 1-VLP vaccines. Unfortunately, however, the neutralizing titers produced upon L2 vaccination are considerably lower than for L1 VLP vaccines, particularly against heterologous HPV types (41). Therefore, it is likely that an L2 vaccine will only be effective if its immunogenicity is enhanced.

VLPs Induce Strong Antibody Responses.

Virus-like particles (VLPs) make excellent vaccines. They are non-infectious, often easier to produce than actual viruses, and, because the regularity of their capsid structure presents viral epitopes as dense, highly repetitive arrays that strongly stimulate B cells, they are highly immunogenic. VLPs are comprised of one or more proteins arranged geometrically into dense, repetitive arrays. These structures are largely unique to microbial antigens, and the mammalian immune system has apparently evolved to respond vigorously to this arrangement of antigens. B cells specifically recognize and respond strongly to the ordered array of densely spaced repetitive elements characteristic of virus surfaces (2, 18). Highly repetitive antigens provoke oligomerization of the membrane-associated immunoglobulin (Ig) molecules that constitute the B cell receptor (BCR) (3). There is evidence that the Ig crosslinking mediated by multivalent antigens leads to the formation of highly stable BCR-signaling microdomains that are associated with increased signaling to the B cell (48). This signaling stimulates B cell proliferation, migration, and upregulation of both major histocompatibility complex (MHC) class II and the co-stimulatory molecules that permit subsequent interactions with T helper cells that are required to trigger IgG secretion, affinity maturation, and the generation of long-lived memory B cells (9). Consequently, we and others have shown that multivalent antigens such as VLPs can activate B cells at much lower concentrations than monomeric antigens (4, 16, 17, 32). Hence, VLPs are innately immunogenic: they induce high titer and long lasting antibody responses at low doses, often without requiring adjuvants (22, 50).

VLPs as Flexible Platforms for Vaccine Development.

VLPs can be used as the basis for vaccines targeting the virus from which they were derived (the Hepatitis B virus vaccine and aforementioned HPV vaccine are two clinically approved VLP vaccines, other VLP vaccines are in clinical trials). However, they also can be used as platforms to display practically any epitope in a highly immunogenic, multivalent format. Heterologous antigens displayed at high density on the surface of VLPs exhibit the same high immunogenicity as unmodified VLPs. VLPs derived from a variety of different viruses have been exploited in this manner to induce antibody responses against heterologous targets that are poorly immunogenic in their native contexts. Although the VLP platform strategy has typically been applied to target antigens derived from pathogens, VLP-display can effectively induce antibody responses against practically any antigen. One example is the vaccine for nicotine addiction (designed to assist smokers who are trying to quit) developed by a biotechnology company, Cytos Biotechnology. This vaccine consists of nicotine, conjugated at high copy number to the surface of VLPs derived from a bacteriophage. In phase II clinical trials, VLPs displaying nicotine were well-tolerated and induced strong nicotine-specific IgG responses in 100% of immunized subjects (14). Even self-antigens, which are normally subject to the mechanisms of B cell tolerance, are immunogenic when displayed at high density on the surface of VLPs. Vaccines have been developed against self-molecules involved in several different diseases, including amyloid-beta (Alzheimers (12, 27)), TNF-α (arthritis (10)), CCR5 (HIV infection (8, 11)), gastrin (cancer, unpublished data), IgE (allergy, unpublished data), and others. VLP-based vaccines developed by pharmaceutical companies targeting amyloid-beta and angiotensin II (hypertension) are currently being evaluated in clinical trials; positive results from the trial of vaccine targeting angiotensin II (as a vaccine for hypertension) were reported in the spring of 2008 (49).

HPV vaccines that target the L2 protein have been described in a variety of other journal articles, patents, and patent applications.

For example, Kawana et al. describe a peptide representing amino acids 108-120 from HPV16 L2 that induces neutralizing antibodies effective against HPV16 and HPV11 (23). The information obtained from these results was said to be useful for developing a prophylactic peptide vaccine that prevents infection with genital HPVs in humans.

U.S. Pat. No. 6,174,532 and PCT/US2006/003601 described the use of the N-terminal portion of papillomavirus L2 protein or a prophylactically effective peptide fragment thereof (or a prophylactically effective peptide derivative sequence thereof) in the production of a medicament suitable for use as a prophylactic agent against papillomavirus infection in mammals.

U.S. Patent Application Document No. 2008/0213293 describes treating or preventing respiratory papillomatosis by immunizing either a mother or child before, during or after delivery. Immunity may be induced with a vaccine comprising a HPV peptide antigen fused to a viral protein or other antigen. Antibodies and cells may be recovered from an animal previously vaccinated with the same vaccine. Of particular interest is the use of HPV L2 peptides designating a neutralizing epitope of HPV.

PCT/US2008/053498 described the use of papillomavirus L2 polypeptides produced in a plant expression system as a prophylactic HPV vaccine.

PCT WO 93/00436 describes papillomavirus L2 protein for use in the production of a medicament for use in medicine, particularly for use in the prophylaxis or therapy of papillomavirus tumours.

PCT 2004/052395 describes a vaccine composition comprising an HPV L2 peptide in physical association with an HPV virus like particle (VLP).

PCT 2008/082719 describes a composition that includes: a papillomavirus virus-like particle including an L1 protein or polypeptide and a chimeric protein or polypeptide that contains at least a portion of an L2 protein 20 and a protein or polypeptide fragment including a first epitope; and a DNA molecule encoding a protein or polypeptide including a second epitope.

OBJECTS OF THE INVENTION

It is an object of the invention to provide a virus-like particle (VLP) virus-like particle comprising a bacteriophage single chain coat polypeptide dimer, preferably based upon a MS2 or PP7 bacteriophage and a HPV L2 peptide, wherein the HPV L2 peptide is displayed on the virus-like particle, in an unconstrained conformation, and said VLP encapsidates bacteriophage mRNA, such that the composition is immunotherapeutic and prophylactic for HPV-induced disorders.

It is another object of the invention to provide nucleic acid constructs which express a VLP comprising a bacteriophage single chain coat polypeptide dimer, preferably based upon a MS2 or PP7 bacteriophage and a HPV L2 peptide, wherein the HPV L2 peptide is displayed on the viral-like particle in an unconstrained conformation, and wherein said VLP encapsidates bacteriophage mRNA.

It is another object of the invention to provide a method of instilling immunogenicity or prophylaxis to a HPV infection and/or a HPV related disorder in a patient at risk for such an infection or disorder.

SUMMARY OF THE INVENTION

The development and commercialization of the HPV vaccines based on L1-VLPs has been a significant public health breakthrough towards the goal of eradicating HPV-associated cancers. However, the current vaccines largely elicit type-specific immunity, meaning that it may be impossible to use L1-VLPs to provide complete protection against the multiple high risk genotypes associated with cancer. Immunization with HPV L2 induces antibodies that broadly neutralize divergent HPV strains, but L2 is poorly immunogenic. As a consequence of the limitations of prior art vaccines, therefore, new strategies for identifying antigenic epitopes, and conformations thereof, and eliciting high-titer anti-L2 antibody responses are needed.

The invention provides immunotherapeutic and prophylactic bacteriophage viral-like particle (VLPs) which are useful in the treatment and prevention of human papillomavirus (HPV) infections and related disorders, including cervical cancer and persistent infections associated with HPV. Related compositions (e.g. vaccines), nucleic acid constructs, and therapeutic methods are also provided. VLPs and related compositions of the invention induce high titer antibody responses against HPV L2 and protect against HPV pseudovirus challenge in vivo. VLPs, VLP-containing compositions, and therapeutic methods of the invention induce an immunogenic response against HPV infection, confer immunity against HPV infection, protect against HPV infection, and reduce the likelihood of infection by and/or inhibit HPV infection.

Because antibodies that are specific for highly conserved epitopes within L2 are able to neutralize infection by a broad range of HPV types, HPV L2-targeting VLPs and related compositions (e.g. vaccines) of the invention provide a more comprehensive protection against infection by multiple HPV types.

In one aspect, the invention provides a VLP comprising a bacteriophage single chain coat polypeptide dimer and a HPV L2 peptide, wherein the HPV L2 peptide is displayed on the VLP, in an unconstrained conformation, and wherein the VLP is immuno-prophylactic for HPV-induced disorders.

Certain aspects of the invention reflect that the single-chain dimer of PP7 coat protein can tolerate the insertion of a wide variety of peptides, including peptides derived from the L2 protein of different strains of HPV or papillomavirus from a variety of non-human (animal) species as otherwise set forth herein, and is highly immunogenic.

Certain aspects of the invention also reflect that in an animal in vivo challenge model, a PP7 VLP displays a broadly cross-type neutralizing epitope from the HPV minor capsid protein L2 and induces antibodies that protect against homologous and heterologous HPV infection. These sequences preferably represent at least 5 consecutive amino acids, preferably from 5 consecutive amino acids to 30 consecutive amino acids (including 5, 6, 7, 8, 9, 10, 11, 12, 13, 14, 15, 16, 17, 18, 19, 20, 21, 22, 23, 24, 25, 26, 27, 28, 29 and 30 consecutive amino acids within this range) at least 10 consecutive amino acids, 15 consecutive amino acids, 20 consecutive amino acids, 25 consecutive amino acids or 30 amino acids of HPV L2 peptide amino acid sequences 11-125, preferably amino acids 14-40, 11-36, 17-36, 11-31, preferably, amino acids 17-31 of L2 peptide of a variety of HPV strains as otherwise described herein, especially including strains 16, 45 and/or 58 as well as HPV strains 1, 5, 6, 11 and 18. In the case of sequences 17-31 of papilloma virus strains HPV1, HPV2, HPV5, HPV6, HPV8, HPV11, HPV16, HPV18, HPV31, HPV33, HPV35, HPV39, HPV45, HPV51, HPV52, HPV56, HPV58, HPV59, HPV66, HPV68, HPV73, CRPV and BPV1 (see FIG. 3 hereof) especially including HPV strains 16, 45 and/or 58, as well as of HPV strains 1, 5, 6, 11 and 48, it is noted that the sequence of this region of HPV peptide L2 is relatively conserved across diverse HPV isolates and the use of each of these sequences within the VLPs according to the present invention may instill immunogenic protection against a broad array of a variety of strains of HPV. In certain embodiments, amino acids 17-31 of L2 peptide of a variety of HPV strains as otherwise described herein (preferably, HPV1, HPV2, HPV5, HPV6, HPV8, HPV11, HPV16, HPV18, HPV31, HPV33, HPV35, HPV39, HPV45, HPV51, HPV52, HPV56, HPV58, HPV59, HPV66, HPV68, HPV73, CRPV and BPV 1 (see FIG. 3 hereof) especially including HPV strains 16, 45 and/or 58, as well as of HPV strains 1, 5, 6, 11 and 48) displayed in an unconstrained conformation at the amino or carboxy terminus of the VLP (preferably, an MS2 VLP, but also including other VLPs based upon RNA bacteriophages as otherwise described herein, such as Qβ, R17, PP7, SP, GA, M11, MX1, f4, Cb5, Cb12r, Cb23r, 7s and f2 RNA bacteriophage VLPs) provides a particularly potent immunogenic response in a patient, significantly greater than the response elicited by immunogenic peptides which are displayed in a constrained conformation, including amino acids 17-31 described above, compared to immunogenic peptides (including amino acids 17-31 as otherwise described herein) which are displayed in a constrained conformation on the VLP or closely related amino acids such as 17-32 of L2 peptide which are displayed on the VLP in an unconstrained conformation.

L2 peptide sequences as described above from any of HPV strains HPV1, HPV2, HPV3, HPV4, HPV5, HPV6, HPV7, HPV8, HPV9, HPV10, HPV11, HPV12, HPV13, HPV14, HPV15, HPV16, HPV17, HPV18, HPV19, HPV20, HPV21, HPV22, HPV23, HPV24, HPV25, HPV26, HPV27, HPV28, HPV29, HPV30, HPV31, HPV32, HPV33, HPV34, HPV35, HPV36, HPV37, HPV38, HPV39, HPV40, HPV41, HPV42, HPV43, HPV44, HPV45, HPV46, HPV47, HPV48, HPV49, HPV50, HPV51, HPV52, HPV53, HPV54, HPV55, HPV56, HPV57, HPV58, HPV59, HPV60, HPV61, HPV62, HPV63, HPV64, HPV65, HPV66, HPV67, HPV68, HPV69, HPV70, HPV71, HPV72, HPV73, HPV74, HPV75, HPV76, HPV77, HPV78, HPV79, HPV80, HPV81, HPV82, HPV83, HPV84, HPV85, HPV86, HPV87, HPV88, HPV89, HPV90, HPV91, HPV92, HPV93, HPV94, HPV95, HPV96, HPV97, HPV98, HPV99, HPV100; and/or animal papillomaviruses: bovine papillomavirus type 1 (BPV1), bovine papillomavirus type 2 (BPV2), bovine papillomavirus type 4 (BPV4), cottontail rabbit papillomavirus (CRPV), deer papillomavirus (DPV), European elk papillomavirus (EEPV), canine oral papillomavirus (COPV), Rhesus monkey papillomavirus (RnPV) and rabbit oral papillomavirus (ROPV) may be displayed by the VLPs according to the present invention. Preferably, peptides comprising or consisting of amino acids 17-31 of the above-referenced HPV strains are used preferably, HPV1, HPV2, HPV5, HPV6, HPV8, HPV11, HPV16, HPV18, HPV31, HPV33, HPV35, HPV39, HPV45, HPV51, HPV52, HPV56, HPV58, HPV59, HPV66, HPV68, HPV73, CRPV and BPV1 (see FIG. 3 hereof) and especially including HPV strains 16, 45 and/or 58, as well as of HPV strains 1, 5, 6, 11 and 48.

Representative L2 peptides for use in VLPs according to the present invention include the following for each of the above-referenced HPV strains and animal PVs (note that all of the amino acid numbers listed below are referenced based upon the sequence of HPV16 L2 and that for each of the lengths of amino acids, each length within the length range is understood to be disclosed):

Linear peptides of lengths varying from 5-30 amino acids from anywhere in L2 (from the list of HPV and animal PVs set forth above);
Linear peptides of lengths varying from 5-30 amino acids from amino acids 1-121 of L2;
Linear peptides of lengths varying from 5-30 amino acids from amino acids 1-88 of L2;
Linear peptides of lengths varying from 5-27 amino acids from amino acids 14-40 of L2;
Linear peptides of varying lengths from 5-21 amino acids from amino acids 17-36 of L2;
Linear peptides of varying lengths from 5-15 amino acids from amino acids 17-31 of L2;
The following sequences of the above referenced PVs (or portions of at least 5, 10 or 15 amino acids thereof):
aa 28-52;
aa 34-52;
aa 35-50;
aa 49-71;
aa 51-65;
aa 61-75;
aa 64-81;
aa 65-85;
aa 65-80.

Other L2 sequences are readily obtained from the detailed description of the invention.

In another aspect, the invention provides a composition comprising a VLP comprising a bacteriophage single chain coat polypeptide dimer and a HPV L2 peptide as otherwise described above (preferably, a peptide consisting of amino acids 17-31 from a variety of HPV strains), wherein the HPV L2 peptide is displayed on the VLP, in an unconstrained conformation, and encapsidates bacteriophage mRNA, and wherein the composition is immunotherapeutic and prophylactic for HPV-induced disorders.

In another aspect, the invention provides a composition comprising a VLP displaying L2 peptides from two or more strains of HPV, such as amino acids 17-31 from both HPV16 and HPV18 L2, on the same VLP, in an unconstrained conformation, and wherein the composition is immunotherapeutic and prophylactic for HPV-induced disorders.

In certain aspects, the invention provides a VLP, or a composition comprising a VLP, wherein the VLP is made by transforming a prokaryote with a nucleic acid construct comprising:
(a) a bacterial or bacteriophage promoter;
(b) a coding sequence of a bacteriophage single chain coat polypeptide dimer (preferably a PP7 coat polypeptide dimer) which is operably associated with the promoter and which is modified to contain a nucleotide sequence encoding a HPV L2 peptide;
(c) a gene for resistance to an antibiotic which is operably associated with the promoter; and
(d) a replication origin for replication in a prokaryotic cell, wherein the composition is immunotherapeutic and/or prophylactic for HPV-induced disorders.

In certain aspects, VLPs and VLP-containing compositions (e.g. vaccines) of the invention are comprised of VLPs comprising HPV L2 peptides from different HPV types. In other aspects, VLPs and VLP-containing compositions of the invention comprise hybrid VLPs that display HPV L2 sequences in an unconstrained conformation derived from multiple HPV types.

In certain aspects, the invention provides a VLP, or a composition comprising a VLP, wherein the VLP is made by transforming a prokaryote with a nucleic acid construct comprising either:
(1) (a) a bacterial or bacteriophage promoter which is operably associated with a coding sequence of a bacteriophage (preferably PP7 or MS2) single chain coat polypeptide dimer, wherein the coat polypeptide dimer coding sequence is modified to: (i) define a first restriction site which is located in the downstream portion of the coat polypeptide dimer coding sequence and which is either positioned 5' to, or located within, the sequence which defines the coat polypeptide dimer AB loop, and (ii) contain a nucleotide sequence encoding a HPV L2 peptide;
(b) a second restriction site positioned 3' to the coat polypeptide dimer coding sequence;
(c) an antibiotic resistance gene which is operably associated with the promoter; and
(d) a replication origin for replication in a prokaryotic cell; or
(2) (a) a bacterial or bacteriophage promoter which is operably associated with a coding sequence of a bacteriophage (preferably MS2), single chain coat polypeptide dimer, wherein the coat polypeptide dimer coding sequence is modified to: (i) define a first restriction site which is located in the downstream portion of the coat polypeptide dimer coding sequence and which is either positioned 5' to, or located within (preferably within), the sequence which defines the coat polypeptide dimer AB loop, and (ii) contain a nucleotide sequence encoding a HPV L2 peptide;
(b) a second restriction site positioned 3' to the coat polypeptide dimer coding sequence;
(c) a PCR primer positioned 3' to the second restriction site;
(d) an antibiotic resistance gene which is operably associated with the promoter; and
(e) a replication origin for replication in a prokaryotic cell; or (3) (a) a bacterial or bacteriophage promoter which is operably associated with a coding sequence of a bacteriophage (preferably MS2) single chain coat polypeptide dimer, wherein the coat polypeptide dimer coding sequence is modified to (i) define a codon sequence positioned 5' to that portion of the sequence which defines the coat polypeptide dimer AB loop, and (ii) contain a nucleotide sequence encoding a HPV L2 peptide;
(b) a restriction site positioned 3' to the coat polypeptide dimer coding sequence;
(c) a PCR primer positioned 3' to the second restriction site;
(d) an antibiotic resistance gene for resistance to a first antibiotic, wherein the resistance gene is operably associated with the promoter;
(e) a helper phage gene modified to contain a second antibiotic resistance gene conferring resistance to a second antibiotic, and
(f) a replication origin for replication in a prokaryotic cell.

In alternative embodiments, the present invention provides a VLP, or a composition comprising a VLP, wherein the VLP is made by transforming a prokaryote with a nucleic aci construct comprising either:

(1) (a) a bacterial or bacteriophage promoter which is operably associated with a coding sequence of bacteriophage PP7 single chain coat polypeptide dimer, wherein the coat polypeptide dimer coding sequence is modified to: (i) define a first restriction site which is located in the downstream portion of the coat polypeptide dimer coding sequence and which is either positioned 5' to, or located within, the sequence which defines the coat polypeptide dimer N-terminus, and (ii) contain a nucleotide sequence encoding a HPV L2 peptide; (b) a second restriction site positioned 3' to the coat polypeptide dimer coding sequence; (c) an antibiotic resistance gene which is operably associated with the promoter; and (d) a replication origin for replication in a prokaryotic cell; or (2) (a) a bacterial or bacteriophage promoter which is operably associated with a coding sequence of bacteriophage MS2 single chain coat polypeptide dimer, wherein the coat polypeptide dimer coding sequence is modified to (i) define a codon sequence positioned 5' to that portion of the sequence which defines the coat polypeptide dimer N-terminus, and (ii) contain a nucleotide sequence encoding a HPV L2 peptide; (b) a restriction site positioned 3' to the coat polypeptide dimer coding sequence; (c) a PCR primer positioned 3' to the second restriction site; (d) a repressor to resistance to a first antibiotic, wherein the repressor is operably associated with the promoter; (e) a helper phage gene modified to contain a gene conferring resistance to a second antibiotic, and (f) a replication origin for replication in a prokaryotic cell.

In certain aspects, the invention provides VLPs made by transforming a prokaryote with HPV L2 peptide sequence-containing constructs as described herein. In other aspects, VLPs and VLP-containing compositions (e.g. vaccines) of the invention are comprised of VLPs comprising HPV L2 peptides derived from different HPV types. In other aspects, VLPs and VLP-containing compositions of the invention comprise hybrid VLPs that display multiple HPV L2 sequences.

In certain aspects, the coding sequence of the bacteriophage single chain coat polypeptide dimer further comprises a transcription terminator positioned 5' to the second restriction site.

In certain aspects, the invention provides a method of inoculating a subject at risk of developing a HPV-related disorder, the method comprising administering to the subject one or more doses of a composition comprising a HPV L2-containing VLP as described herein. In other aspects, the invention provides a method of treating a subject who is at risk of developing a HPV-related disorder and who has undergone HPV seroconversion, the method comprising administering to the subject one or more doses of a composition comprising a HPV L2-containing VLP as described herein. In still other aspects, the invention provides a method of treating a subject who has developed a HPV-related disorder, the method comprising administering to the subject one or more doses of a composition comprising a HPV L2-containing VLP as described herein.

Previously, we described the use of VLPs of the RNA bacteriophage MS2 for peptide display. By genetically fusing two copies of the MS2 coat protein, we created a single-chain dimer with increased thermodynamic stability and vastly improved tolerance of insertions in its AB-loop (38). The MS2 coat protein dimer was widely tolerant of genetic insertion of defined peptide sequences as well as random peptide insertions. Recombinant MS2 VLPs elicited high titer IgG antibodies against the inserted sequences. Moreover, MS2 coat protein single-chain dimers produced correctly assembled VLPs that specifically encapsidated the mRNA encoding their synthesis, raising the possibility that they could be used in affinity selections protocols analogous to filamentous phage display.

Since MS2 is only one member of a large family of bacteriophages whose individual members share similar molecular biology, we suspected that, following similar design principles, other phage VLPs could be adapted to this same purpose. For example, here in addition to the use of MS2 VLPs, we describe the engineering of other VLPs including PP7, a bacteriophage of *Pseudomonas aeruginosa*, for the purposes of peptide display.

Thus, we describe the use of recombinant VLPs derived RNA bacteriophages to induce high titer antibody responses against L2 that protect against multiple diverse HPV types.

These and other aspects of the invention are described further in the Detailed Description of the Invention.

BRIEF DESCRIPTION OF THE FIGURES

FIG. 2. Nucleotide sequences of the plasmids p2P7K32 and pET2P7K32. SEQ ID No. 1

FIG. 3. The N-terminal sequence of the downstream copy of coat protein encoded by p2P7K32, SEQ ID No. 2. Below this is a list of selected forward primers used to clone the listed sequences into PP7 coat (shown 5' to 3'). A similar strategy was used to clone sequences from HPV1, 5/8, 6, 11/33, 16, 18, 33, 39/45, and 52/58 L2 into the PP7 coat protein. The KpnI restriction site is shown in italics and the peptide insertion is shown in bold text. All of these primers yield an insertion which is flanked by a thr residue on the N-terminal side and a glu (the wild-type position 11 amino acid) on the C-terminal side.

FIG. 4. Amino acid sequence of L2 (17-31, or equivalent) from selected STI/carcinogenic/cutaneous HPV and animal papillomavirus types, adapted from (1). PP7 VLPs displaying a subset of these sequences were constructed. The following sequence ID Nos. apply to the disclosed amino acid sequences: HPV1 (SEQ ID No. 12), HPV5 (SEQ ID No. 13), HPV8 (SEQ ID No. 14), HPV16 (SEQ ID No. 15), HPV35 (SEQ ID No. 16), HPV31 (SEQ ID No. 17), HPV33 (SEQ ID No. 18), HPV58 (SEQ ID No. 19), HPV52 (SEQ ID No. 20), HPV73 (SEQ ID No. 21), HPV6 (SEQ ID No. 22), HPV11 (SEQ ID No. 23), HPV18 (SEQ ID No. 24), HPV45 (SEQ ID No. 25), HPV39 (SEQ ID No. 26), HPV68 (SEQ ID No. 27), HPV59 (SEQ ID No. 28), HPV51 (SEQ ID No. 29), HPV56 (SEQ ID No. 30), HPV66 (SEQ ID No. 31), HPV2 (SEQ ID No. 32), CPRV (SEQ ID No. 33) and BPV1 (SEQ ID No. 34).

FIG. 6. Binding of an anti-16L2 monoclonal antibody against (RG-1) to recombinant VLPs. (A) Dilutions of the mAb was reacted with 500 ng/well of wild-type PP7, 16L2, and Flag-VLPs. Binding was detected using a horseradish peroxidase-labeled goat anti-mouse IgG secondary followed by development with ABTS. Reactivity was determined by measurement of the absorbance at 405 nm (OD 405). (B) Reactivity of a 1:5000 dilution of RG-1 mAb to the eight recombinant L2 VLPs constructed, or to wild-type PP7 VLPs.

FIG. 12 shows that the expression of an antigenic epitope in an unconstrained conformation elicits a more broadly protective antibody response than presentation in a constrained loop.

FIG. 13 lists the forward primers used to clone the listed sequences into MS2 coat (shown 5' to 3'), as well as the amino acids sequences encoded by these primers. The NcoI restriction site is shown in underlined italics, the peptide insertion is shown in bold text, and the linker sequence is shown in italics. MS2 coat protein sequences are underlined.

FIG. 19 depicts the plasmid pDSP1.

FIG. 20 shows that there were dramatic differences in protection from heterologous HPV PsV challenge. Immunization with L2-PP7 VLPs resulted in modest or no protection against heterologous PsV. In contrast, immunization with N-terminal displayed L2-MS2 VLPs according to the present invention resulted in significant protection from vaginal challenge with nine heterologous types and one intradermal challenge with HPV5 PsV. We observed very strong (80- to 7.190-fold reduction in signal) protection from infection with 9 out of the heterologous PsV types tested, an unexpected result. This protection was substantially stronger than what was observed in mice immunized with AB-loop displayed L2. Protection against homologous challenge using VLPs according to the present invention was generally at least about 5-10-fold greater than VLPs where an antigenic L2 peptide was displayed in the AB-loop. Protection against heterologous challenge was 10-25-fold (HPV5, 31 & 39), 40-100-fold (HPV45, 51, 53, & 58), or 140-1000-fold (HPV6, 33, & 35) better using the N-terminal VLP construct.

DETAILED DESCRIPTION OF THE INVENTION

Figure 1:
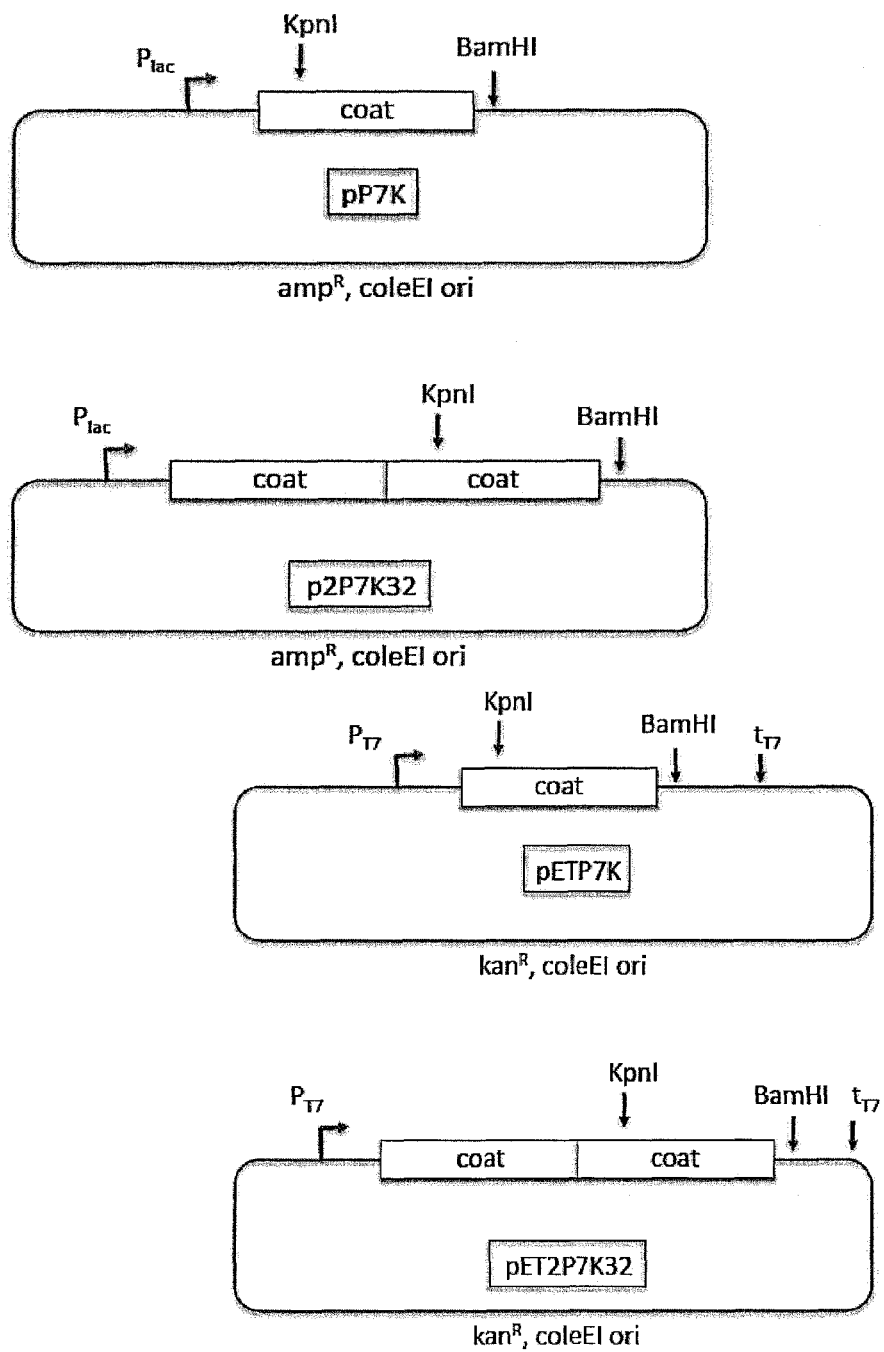
FIG. 1. Plasmids for expression of recombinant PP7 coat protein, including pP7K, p2P7K32, pETP7K, and pET2P7K32.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal and preferably a human, to whom treatment, including prophylactic treatment (prophylaxis), with the immunogenic compositions and/or vaccines according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe a number of VLP's or an amount of a VLP-containing composition which, in context, is used to produce or effect an intended result, whether that result relates to the prophylaxis and/or therapy of an HPV-induced or HPV-related disorder or disease state or as otherwise described herein. The term effective subsumes all other effective amount or effective concentration terms (including the term "therapeutically effective") which are otherwise described or used in the present application.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

The term "single-chain dimer" refers to a normally dimeric protein whose two subunits of coat polypeptide of a RNA bacteriophage have been genetically (chemically, through covalent bonds) fused into a single polypeptide chain. Specifically, in the present invention single-chain dimer versions of PP7 coat proteins were constructed. Each of these proteins is naturally a dimer of identical polypeptide chains. In the PP7 coat protein dimers the N-terminus of one subunit lies in close physical proximity to the C-terminus of the companion subunit. Single-chain coat protein dimers were produced using recombinant DNA methods by duplicating the DNA coding sequence of the coat proteins and then fusing them to one another in tail to head fashion. The result is a single polypeptide chain in which the coat protein amino acid appears twice, with the C-terminus of the upstream copy covalently fused to the N-terminus of the downstream copy. Normally (wild-type) the two subunits are associated only through noncovalent interactions between the two chains. In the single-chain dimer these noncovalent interactions are maintained, but the two subunits have additionally been covalently tethered to one another. This greatly stabilizes the folded structure of the protein and confers to it its high tolerance of peptide insertions as described above.

This application makes frequent reference to coat protein's "AB-loop". The RNA phage coat proteins possess a conserved tertiary structure. The PP7 coat proteins, for example, possess a structure wherein each of the polypeptide chains is folded into of a number of β-strands. The β-strands A and B form a hairpin with a three-amino acid loop connecting the two strands at the top of the hairpin, where it is exposed on the surface of the VLP. As evidenced in the present application, peptides inserted into the AB-loop are exposed on the surface of the VLP and are strongly immunogenic.

The amino acid residues described herein are preferred to be in the "L" isomeric form. However, residues in the "D" isomeric form can be substituted for any L-amino acid residue, as long as the desired functional is retained by the polypeptide. $NH_2$ refers to the free amino group present at the amino terminus of a polypeptide. COOH refers to the free carboxy group present at the carboxy terminus of a polypeptide.

The term "valency" is used to describe the density of L2 peptide display on VLPs according to the present invention. Valency in the present invention may range from low valency to high valency, about less than 1 to more than about 180, preferably about 90 to 180. Immunogenic compositions according to the present invention comprise VLPs which are preferably high valency and comprise VLPs which display at least 50-60 up to about 180 or more L2 peptides.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "origin of replication", used within context, normally refers to those DNA sequences that participate in DNA synthesis by specifying a DNA replication initiation region. In the presence of needed factors (DNA polymerases, and the like) an origin of replication causes or facilitates DNA associated with it to be replicated. By way of a non-limiting example, the ColE1 replication origin endows many commonly used plasmid cloning vectors with the capacity to replicate independently of the bacterial chromosome. Another example is the p15A replication origin. The presence on a plasmid of an additional origin of replication from phage M13 confers the additional ability to replicate using that origin when E. coli cells are infected with a so-called helper phage (e.g. M13CM1) which provides necessary protein factors. M13 replicates intracellularly as double-stranded circular DNA, but also produces a single-stranded circular form, which it packages within the phage particle. These particles provide a convenient source of single-stranded circular DNA for plasmids.

A "promoter sequence" is a DNA regulatory region capable of binding RNA polymerase in a cell and initiating transcription of a downstream (3' direction) coding sequence. For purposes of defining the present invention, the promoter sequence includes the minimum number of bases or elements necessary to initiate transcription at levels detectable above background. Within the promoter will be found DNA sequences responsible for the binding of RNA polymerase and any of the associated factors necessary for transcription initiation. In bacteria promoters normally consist of –35 and –10 consensus sequences and a more or less specific transcription initiation site. Eukaryotic promoters will often, but not always, contain "TATA" boxes and "CAT" boxes. Bacterial expression vectors (usually plasmids or phages) typically utilize promoters derived from natural sources, including those derived from the E. coli Lactose, Arabinose, Tryptophan, and ProB operons, as well as others from bacteriophage sources. Examples include promoters from bacteriophages lambda, T7, T3 and SP6.

In bacteria, transcription normally terminates at specific transcription termination sequences, which typically are categorized as rho-dependent and rho-independent (or intrinsic) terminators, depending on whether they require the action of the bacterial rho-factor for their activity. These terminators specify the sites at which RNA polymerase is caused to stop its transcription activity, and thus they largely define the 3'-ends of the RNAs, although sometimes subsequent action of ribonucleases further trims the RNA.

An "antibiotic resistance gene" refers to a gene that encodes a protein that renders a bacterium resistant to a given antibiotic. For example, the kanamycin resistance gene directs the synthesis of a phosphotransferase that modifies and inactivates the drug. The presence on plasmids of a kanamycin resistance gene provides a mechanism to select for the presence of the plasmid within transformed bacteria. Similarly, the chloramphenicol resistance gene allows bacteria to grow in the presence of the drug by producing an acetyltransferase enzyme that inactivates the antibiotic through acetylation.

The term "PCR" refers to the polymerase chain reaction, a technique used for the amplification of specific DNA sequences in vitro. The term "PCR primer" refers to DNA sequences (usually synthetic oligonucleotides) able to anneal to a target DNA, thus allowing a DNA polymerase (e.g. Taq DNA polymerase) to initiate DNA synthesis. Pairs of PCR primers are used in the polymerase chain reaction to initiate DNA synthesis on each of the two strands of a DNA and to thus amplify the DNA segment between two primers. Representative PCR primers which used in the present invention are those which are presented in FIG. 3 hereof. Additional PCR primers may be obtained for the various HPV L2 peptides which are presented herein.

Examples of primers used for PCR are given in FIG. 3 as described above and the following.

E3.2: 5' CGG GCT TTG TTA GCA GCC GG 3'—(SEQ ID No. 35) serves as the 3' (reverse)-primer in PCR reactions to amplify coat protein.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional control sequences are DNA regulatory sequences, such as promoters, enhancers, polyadenylation signals, terminators, and the like, that provide for the expression of a coding sequence in a host cell. Translational control sequences determine the efficiency of translation of a messenger RNA, usually by controlling the efficiency of ribosome binding and translation initiation. For example, as discussed elsewhere in this application, the coat proteins of the RNA phages are well-known translational repressors of the phage replicase. As coat protein accumulates to a sufficiently high concentration in the infected cell, it binds to an RNA hairpin that contains the translation initiation region (Shine-Dalgarno and initiator AUG) of the phage's replicase gene. This prevents ribosome binding and shuts off replicase synthesis at a time in the viral life cycle where the transition from replication to virus assembly occurs.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid, which normally replicate independently of the bacterial chromosome by virtue of the presence on the plasmid of a replication origin. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least about 8-10 up to about 20 or more such amino acids. Methods of determining the spatial conformation of amino acids are known in the art, and include, for example, x-ray crystallography and 2-dimensional nuclear magnetic resonance.

As used herein, a "mimotope" is a peptide that mimics an authentic antigenic epitope.

As used herein, the term "coat protein(s)" refers to the protein(s) of a bacteriophage or a RNA-phage capable of being incorporated within the capsid assembly of the bacteriophage or the RNA-phage.

As used herein, a "coat polypeptide" as defined herein is a polypeptide fragment of the coat protein that possesses coat protein function and additionally encompasses the full length coat protein as well or single-chain variants thereof.

As used herein, the term "immune response" refers to a humoral immune response and/or cellular immune response leading to the activation or proliferation of B- and/or T-lymphocytes and/or antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

As used herein, the term "vaccine" refers to a formulation which contains the composition of the present invention and which is in a form that is capable of being administered to an animal and provides a measure of protection (protective effect) against a disease state or condition for which the vaccine is administered. The term "prevention" or "prophylaxis" is used in context synonymously with the term "reducing the likelihood of" or "inhibiting" wherein the measure of prevention (of a disease state or condition) is one of degree of effect, given that a protective effect will usually be seen in most, but not all within a given population group. Vaccines according to the present invention may also instill immunity in a patient or subject against a disease state or condition and such immunity is consistent with the use of the term "prevention" or "prophylaxis" as used above.

As used herein, the term "virus-like particle of a bacteriophage" refers to a virus-like particle (VLP) resembling the structure of a bacteriophage, being non-replicative and noninfectious, and lacking at least the gene or genes encoding for the replication machinery of the bacteriophage, and typically also lacking the gene or genes encoding the protein or proteins responsible for viral attachment to or entry into the host. This definition should, however, also be seen to encompass virus-like particles of bacteriophages, in which the aforementioned gene or genes are still present but inactive, and, therefore, also leading to non-replicative and noninfectious virus-like particles of a bacteriophage.

VLP of RNA bacteriophage coat protein: The capsid structure formed from the self-assembly of one or more subunits of RNA bacteriophage coat protein and optionally containing host RNA is referred to as a "VLP of RNA bacteriophage coat protein". In a particular embodiment, the capsid structure is formed from the self assembly of 90-180 subunits.

A "hybrid VLP" refers to a VLP that displays two or more heterologous amino acid sequences on its surface, such as, for example, amino acids 17-31 from HPV16 and HPV18. Such a hybrid VLP could be formed by coexpression of two recombinant coat proteins in the same expression strain of bacteria. Alternatively, hybrid VLPs could be generated in vitro by disassembly of two separate recombinant VLPs into coat protein dimers. Following disassembly, the recombinant coat protein dimers may be mixed together and then reassembled. Methods for assembly and disassembly of PP7 VLPs are described by Caldeira and Peabody (6).

A nucleic acid molecule is "operatively linked" to, or "operably associated with", an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "unconstrained conformation" refers to the specific method of displaying a heterologous polypeptide on a VLP according to the present invention in which at least one end is free to move relative to the adjacent native RNA phage coat proteins (dimers) maintaining flexibility in the 3D structure of the resulting polypeptide construct. A peptide exhibiting an unconstrained conformation is a peptide (most often an immunogenic peptide as otherwise described herein) that lacks forced, specific constraints at both the N- and C-termini and exhibits substantial conformational flexibility in contrast to a constrained peptide. For example, an unconstrained peptide may be displayed at the N- or the C-terminus of a fusion protein or in the present invention at the N- or C-terminus (often, the N-terminus) of a dimer coat polypeptide (which forms a VLP). Quite unexpectedly, display of an immunogenic peptide at the N-terminus of the VLP (preferably, a VLP of a dimer MS2 coat polypeptide) elicited much more broadly reactive antibody responses than display of the same peptide in the AB-loop of a coat protein (PP7). This unexpected result (i.e. significantly enhanced immunogenicity) occurs by inserting an immunogenic peptide at the N-terminus or C-terminus (often, the N-terminus) in a number of VLPs from dimer coat polypeptide as otherwise described herein, It is likely that the insertion/display of the immunogenic peptide at the N-terminus or C-terminus of the VLP allows more conformational flexibility, perhaps, leading to a better exposure of conserved amino acids in this epitope thereby inducing a more broadly reactive antibody response against a conformational epitope. Correspondingly, mice immunized with 16L2 (17-31) Nterm MS2 VLPs were more broadly protected upon vaginal and intradermal challenge with a diverse panel of HPV PsVs and this result is believed to occur by displaying the 16L2 (17-31) peptide at the N-terminus of a number of VLPs which are described herein.

HPV-Induced Disorders, Immunogenicity, and Prophylactic Efficacy

"HPV-induced disorders" or "HPV-related disorders" include, but are not limited to, the disorders identified in this section. Immunogenicity and prophylactic efficacy (e.g. whether a composition is immunotherapeutic and prophylactic for HPV-induced disorders) may be evaluated either by the techniques and standards mentioned in this section, or through other methodologies that are well-known to those of ordinary skill in the art.

Over 100 different HPV types have been identified and are referred to by number. Types 16, 18, 31, 33, 35, 39, 45, 51, 52, 56, 58, and 59 are among the "high-risk" sexually transmitted HPVs and may lead to the development of cervical intraepithelial neoplasia (CIN), vulvar intraepithelial neoplasia (VIN), vaginal cancer, penile intraepithelial neoplasia (PIN), and/or anal intraepithelial neoplasia (AIN). Several types of HPV, particularly type 16, have been found to be associated with oropharyngeal squamous-cell carcinoma, a form of head and neck cancer. HPV (e.g., HPV6 and 11) cause genital warts, and HPV6 and 11 can cause recurrent respiratory papillomatosis. HPV may cause epidermodysplasia verruciformis in immunocompromised individuals. Other HPV types, such as HPV1, can causes cutaneous warts.

High-risk human HPV infection of the cervical epithelium is causally linked with the generation of cervical cancer. See, Durst, et al., PNAS, 80, 3812-1815, 1983; and Glassman, et al., J. Invest. Dermatol., 83, 265-285, 1984. HPV16 is associated with premalignant and malignant diseases of the genito-urinary tract, and in particular with carcinoma of the cervix. Papillomavirus prophylactic immunogenic compositions or vaccines target the systemic immune system for induction of neutralizing antibodies that protect the basal cells against infection. Because the carcinogenic HPVs are susceptible to neutralization by antibodies for 9-48 hours after reaching the basal cells, both low and high titered HPV type-specific antibodies induced by HPV L2-based vaccines should prove highly efficacious.

To assess immunogenicity (e.g. whether a composition has induced a high titer antibody responses against HPV L2, an anti-HPV16 L2 geometric mean titer (GMT) can be measured, e.g. after a few weeks of treatment (e.g. 3 or 4 weeks) and after administration of a few dosages (e.g. 3 or 4). The percentage of subjects who seroconverted for HPV16 after a few weeks of treatment (e.g. 3 or 4 weeks) and after administration of a few dosages (e.g. 3 or 4) and the magnitude of these responses can also be determined to assess immunogenicity.

To determine prophylactic efficacy, an immunogenicity analysis can be conducted on subjects who remain HPV16 seronegative and PCR-negative to HPV infection (swab and biopsy) at various endpoints after challenge.

HPV L2

"HPV L2" as used herein includes the L2 capsid proteins of all human papillomaviruses.

Production of Virus-Like Particles

The present invention is directed to virus-like phage particles as well as methods for producing these particles in vivo or in vitro. The methods typically include producing virus-like particles (VLPs) and recovering the VLPs. As used herein, producing VLPs "in vitro" refers to producing VLPs outside of a cell, for instance, in a cell-free system, while producing virions "in vivo" refers to producing VLPs inside a cell, for instance, an *Eschericia coli* or *Pseudomonas aeruginosa* cell.

Bacteriophages

The system envisioned here is based on the properties of single-strand RNA bacteriophages [RNA Bacteriophages, in The Bacteriophages. Calendar, RL, ed. Oxford University Press. 2005]. The known viruses of this group attack bacteria as diverse as *E. coli, Pseudomonas* and *Acinetobacter*. Each possesses a highly similar genome organization, replication strategy, and virion structure. In particular, the bacteriophages contain a single-stranded (+)-sense RNA genome, contain maturase, coat and replicase genes, and have small (<300 angstrom) icosahedral capsids. These preferably include but are not limited to PP7, MS2, Qβ, R17, SP, PP7, GA, M11, MX1, f4, Cb5, Cb12r, Cb23r, 7s and f2 RNA bacteriophages. PP7 bacteriophages are used in preferred aspects of the present invention.

The information required for assembly of the icosahedral capsid shell of this family of bacteriophage is contained entirely within coat protein itself. For example, purified coat protein can form capsids in vitro in a process stimulated by the presence of RNA [Beckett et al., 1988, J. Mol. Biol 204: 939-47]. Moreover, coat protein expressed in cells from a plasmid assembles into a virus-like particle in vivo [Peabody, D. S., 1990, J Biol Chem 265: 5684-5689].

PP7 is a single-strand RNA bacteriophage of *Pseudomonas aeroginosa* and a distant relative to coliphages like MS2 and Qβ, which also may be used in the present invention. PP7 coat protein is a specific RNA-binding protein, capable of repressing the translation of sequences fused to the translation initiation region of PP7 replicase. Its RNA binding activity is specific since it represses the translational operator of PP7, but does not repress the operators of the MS2 or Qβ phages. Conditions for the purification of coat protein and for the reconstitution of its RNA binding activity from disaggregated virus-like particles have been established. Its dissociation constant for PP7 operator RNA in vitro was determined to be about 1 nM. Using a genetic system in which coat protein represses translation of a replicase-β-galactosidase fusion protein, amino acid residues important for binding of PP7 RNA were identified (28).

The coat proteins of several single-strand RNA bacteriophages are known translational repressors. They shut off viral replicase synthesis by binding an RNA hairpin that contains the replicase ribosome binding site. X-ray structure determination of RNA phages shows that homologies evident from comparisons of coat protein amino acid sequences are reflected in their tertiary structures. The coat protein dimer, which is both the repressor and the basic building block of the virus particle, consists of two intertwined monomers that together form a large β-sheet surface upon which the RNA is bound. Each of the coat proteins uses a common structural framework to bind different RNAs, thereby presenting an opportunity to investigate the basis of specific RNA-protein recognition. We have described the RNA binding properties of the coat protein of PP7, an RNA bacteriophage of *Pseudomonas aeroginosa* whose coat protein shows only 13% amino acid sequence identity to that of MS2. We have also presented the following findings. 1) The coat protein of PP7 is a translational repressor. 2) An RNA hairpin containing the PP7 replicase translation initiation site is specifically bound by PP7 coat protein both in vivo and in vitro, indicating that this structure represents the translational operator. 3) The RNA binding site resides on the coat protein β-sheet.

By way of comparison, the genome of MS2 comprises a single strand of (+)-sense RNA 3569 nucleotides long, encoding only four proteins, two of which are structural components of the virion. The viral particle is comprised of an icosahedral capsid made of 180 copies of coat protein and one molecule of maturase protein together with one molecule of the RNA genome. Coat protein is also a specific RNA binding protein. Assembly may possibly be initiated when coat protein associates with its specific recognition target an RNA hairpin near the 5'-end of the replicase cistron. The virus particle is then liberated into the medium when the cell bursts under the influence of the viral lysis protein. The formation of an infectious virus requires at least three components, namely coat protein, maturase and viral genome RNA, but experiments show that the information required for assembly of the icosahedral capsid shell is contained entirely within coat protein itself. For example, purified coat protein can form capsids in vitro in a process stimulated by the presence of RNA [Beckett et al., 1988, J. Mol. Biol 204: 939-47]. Moreover, coat protein expressed in cells from a plasmid assembles into a virus-like particle in vivo (37).

Examples of PP7 coat polypeptides include but are not limited to the various chains of PP7 Coat Protein Dimer in Complex With RNA Hairpin (e.g. Genbank Accession Nos. 2QUXR; 2QUXO; 2QUX_L; 2QUX_I; 2QUX_F; and 2QUX_C). See also Example 1 herein and Example 1 herein and Peabody, et al., RNA recognition site of PP7 coat protein, Nucleic Acids Research, 2002, Vol. 30, No. 19 4138-4144.

RNA Bacteriophage Coat Polypeptide

The coat polypeptides useful in the present invention also include those having similarity with one or more of the coat polypeptide sequences disclosed above. The similarity is referred to as structural similarity. Structural similarity may be determined by aligning the residues of the two amino acid sequences (i.e., a candidate amino acid sequence and the amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence can be isolated from a single stranded RNA virus, or can be produced using recombinant techniques, or chemically or enzymatically synthesized. Preferably, two amino acid sequences are compared using the BESTFIT algorithm in the GCG package (version 10.2, Madison Wis.), or the Blastp program of the BLAST 2 search algorithm, as described by Tatusova, et al. (*FEMS Microbial Lett* 1999, 174:247-250), and available at on the world wide web at URL ncbi.nlm.nih.gov/blast/b12seq/b12.html. Preferably, the default values for all BLAST 2 search parameters are used, including matrix=BLOSUM62; open gap penalty=11, extension gap penalty=1, gap xdropoff=50, expect=10, wordsize=3, and optionally, filter on. In the comparison of two amino acid sequences using the BLAST search algorithm, structural similarity is referred to as "identities." Preferably, a coat polypeptide also includes polypeptides with an amino acid sequence having at least 80% amino acid identity, at least 85% amino acid identity, at least 90% amino acid identity, or at least 95% amino acid identity to one or more of the amino acid sequences disclosed above. Preferably, a coat polypeptide is active. Whether a coat polypeptide is active can be determined by evaluating the ability of the polypeptide to form a capsid and package a single stranded RNA molecule. Such an evaluation can be done using an in vivo or in vitro system, and such methods are known in the art and routine. Alternatively, a polypeptide may be considered to be structurally similar if it has similar three-dimensional structure as the recited coat polypeptide and/or functional activity.

The HPV L2 Peptide

The HPV L2 peptide sequence may be present at the amino-terminal end of a coat polypeptide, at the carboxy-terminal end of a coat polypeptide, or it may be present elsewhere within the coat polypeptide. Preferably, the HPV L2 peptide sequence is present at a location in the coat polypeptide such that the insert sequence is expressed on the outer surface of the capsid. In a particular embodiment, the HPV L2 peptide sequence may be inserted into the AB loop regions of the above-mentioned coat polypeptides, preferably in the downstream subunit of the single-chain dimer of the coat polypeptide. Examples of such locations include, for instance, insertion or replacement of the insert sequence into a coat polypeptide in accordance with the examples presented hereinafter. Insertion or replacement, preferably insertion, of the L2 peptide sequence into the AB loop region at amino acid units 8-11 of the AB loop, preferably in the downstream subunit of the single-chain dimer coat polypeptide, is preferred.

In another particular embodiment, the HPV L2 peptide sequence may be inserted at the N-terminus or C-terminus of the coat polypeptide, in an unconstrained conformation, preferably in the downstream subunit of the dimer coat polypeptide.

The HPV L2 peptide sequence preferably includes but is not limited to amino acid sequences of, at least, five, ten, fifteen, twenty amino, twenty five or thirty amino acids derived from the minor capsid protein L2 of human Papillomavirus types 1-100, preferably 16 (HPV16), 18, 31, 33, 35, 39, 45, 51, 52, 56, 58 or 59, preferably 16 (HPV16). A preferred peptide includes peptides 17-31 of HPV16.

In another particular embodiment, the L2 peptide sequence includes amino acid sequences with at least 75%, 80%, 85%, 90%, or 95% homology to L2 sequences derived from HPV strains representing the five clades of the virus (HPV1, HPV5, HPV6, HPV16, and HPV18).

In order to determine a corresponding position in a structurally similar coat polypeptide, the amino acid sequence of this structurally similar coat polypeptide is aligned with the sequence of the named coat polypeptide as specified above.

In a particular embodiment, the coat polypeptide is a single-chain dimer containing an upstream and downstream subunit. Each subunit contains a functional coat polypeptide sequence. The HPV L2 peptide sequence may be inserted in the upstream and/or downstream subunit at the sites mentioned hereinabove, e.g., AB loop region of downstream subunit, preferably at amino acid units 8-11 and as otherwise specified in the examples which are described hereinbelow. In a particular embodiment, the coat polypeptide is a single chain dimer of a PP7 coat polypeptide and the L2 peptide sequence is inserted in the AB loop region of the downstream subunit.

In a particular embodiment, the coat polypeptide is a single-chain dimer containing an upstream and downstream subunit. Each subunit contains a functional coat polypeptide sequence. The HPV L2 peptide sequence may be inserted in the upstream and/or downstream subunit at the sites mentioned hereinabove, e.g., inserted at the N-terminus (upstream subunit) or C-terminus (downstream subunit) of the coat polypeptide, in an unconstrained conformation. While any dimer coat polypeptide of a RNA bacteriophage is useful in the present invention, in a particular embodiment, the coat polypeptide is a single chain dimer of the MS2 or PP7 coat polypeptide and the L2 peptide sequence is inserted at the C-terminus for the coat polypeptide such that display of the L2 peptide is in an unconstrained conformation.

In a particular embodiment, the coat polypeptide is a single-chain dimer containing an upstream and downstream subunit. Each subunit contains a functional coat polypeptide sequence. The HPV L2 peptide sequence may be inserted in the upstream and/or downstream subunit at the sites mentioned hereinabove, e.g., inserted at the N-terminus or C-terminus of the coat polypeptide, in an unconstrained conformation. In a particular embodiment, the coat polypeptide is a single chain dimer of the MS2 or PP7 coat polypeptide (most often MS2) and the L2 peptide sequence is inserted at the N-terminus for the coat polypeptide such that display of the L2 peptide is in an unconstrained conformation.

In a particular embodiment, the coat polypeptide is a single-chain dimer containing an upstream and downstream subunit. Each subunit contains a functional coat polypeptide sequence. The HPV L2 peptide sequence may be inserted in the upstream and/or downstream subunit at the sites mentioned hereinabove, e.g., inserted at the N-terminus or C-terminus of the coat polypeptide, in an unconstrained conformation. In a particular embodiment, the coat polypeptide is a single chain dimer of the PP7 coat polypeptide and the L2 peptide sequence is inserted at any point in the sequence of the coat polypeptide which maintains flexibility in 3D structure.

Benefits of Expression in an Unconstrained Structure

Expression of an antigenic epitope in an unconstrained conformation elicits a more broadly protective antibody response than presentation in a constrained loop. This is evidenced by the data shown in FIG. 12.

Preparation of Transcription Unit

The transcription unit of the present invention comprises an expression regulatory region, (e.g., a promoter), a sequence encoding a single chain of a coat polypeptide which includes a HPV L2 peptide encoding sequence and a transcription terminator. The RNA polynucleotide may optionally include a coat recognition site (also referred to a "packaging signal", "translational operator sequence", "coat recognition site"). Alternatively, the transcription unit may be free of the translational operator sequence. The promoter, coding region, transcription terminator, and, when present, the coat recognition site, are generally operably linked. "Operably linked" or "operably associated with" refer to a juxtaposition wherein the components so described are in a relationship permitting them to function in their intended manner. A regulatory sequence is "operably linked" to, or "operably associated with", a coding region when it is joined in such a way that expression of the coding region is achieved under conditions compatible with the regulatory sequence. The coat recognition site, when present, may be at any location within the RNA polynucleotide provided it functions in the intended manner.

The invention is not limited by the use of any particular promoter, and a wide variety of promoters are known. The promoter used in the invention can be a constitutive or an inducible promoter. Preferred promoters are able to drive high levels of RNA encoded by me coding region encoding the coat polypeptide Examples of such promoters are known in the art and include, for instance, the lac promoter, T7, T3, and SP6 promoters.

The nucleotide sequences of the coding regions encoding coat polypeptides described herein are readily determined. These classes of nucleotide sequences are large but finite, and the nucleotide sequence of each member of the class can be readily determined by one skilled in the art by reference to the standard genetic code. Furthermore, the coding sequence of an RNA bacteriophage single chain dimer coat polypeptide comprises a site for insertion of HPV L2 peptide-encoding sequences. In a particular embodiment, the site for insertion of the HPV L2 peptide-encoding sequence is a restriction enzyme site.

In a particular embodiment, the coding region encodes a single-chain dimer of the coat polypeptide, preferably a PP7 coat polypeptide. In a most particular embodiment, the coding region encodes a modified single chain coat polypeptide dimer, where the modification comprises an insertion of a coding sequence at least four amino acids at the insertion site. The transcription unit may contain a bacterial promoter, such as a lac promoter or it may contain a bacteriophage promoter, such as a T7 promoter and optionally a T7 transcription terminator.

In addition to containing a promoter and a coding region encoding a fusion polypeptide, the RNA polynucleotide typically includes a transcription terminator, and optionally, a coat recognition site. A coat recognition site is a nucleotide sequence that forms a hairpin when present as RNA. This is also referred to in the art as a translational operator, a packaging signal, and an RNA binding site. Without intending to be limiting, this structure is believed to act as the binding site recognized by the translational repressor (e.g., the coat polypeptide), and initiate RNA packaging. The nucleotide sequences of coat recognition sites are known in the art. Other coat recognition sequences have been characterized in the single stranded RNA bacteriophages R17, GA, Qβ, SP, and PP7, and are readily available to the skilled person. Essentially any transcriptional terminator can be used in the RNA polynucleotide, provided it functions with the promoter. Transcriptional terminators are known to the skilled person, readily available, and routinely used.

Synthesis

The VLPs of the present invention may be produced in vivo by introducing transcription units into bacteria, especially if transcription units contain a bacterial promoter Alternatively VLPs synthesized in vitro in a coupled cell-free transcription/translation system.

Assembly of VLPs Encapsidating Heterologous Substances

As noted above, the VLPs of the present invention display a HPV L2 peptide-encoding sequence. These VLPs may be assembled by performing an in vitro VLP assembly reaction. Specifically, purified coat protein subunits are obtained from VLPs that have been disaggregated with a denaturant (usually acetic acid). The protein subunits are mixed with a heterologous substance. In a particular embodiment, the substance has some affinity for the interior of the VLP and is preferably negatively charged. This substance could include an adjuvant, including, but not limited to RNA, bacterial DNA (CpG oligonucleotides), cholera toxin subunit B, or *E. coli* lymphotoxin. In certain embodiments, the adjuvant is mixed with coat protein, which is then reassembled in its presence.

In another embodiment, the adjuvant is passively diffused into the VLP through pores that naturally exist in the VLP surface. In a particular embodiment, the substance is small enough to pass through these pores and has a high affinity for the interior of the VLP.

Synthesis

In a particular embodiment, the populations of the present invention may be synthesized in a coupled in vitro transcription/translation system using procedures known in the art (see, for example, U.S. Pat. No. 7,008,651, relevant portions of which are incorporated by reference herein). In a particular embodiment, bacteriophage T7 (or a related) RNA polymerase is used to direct the high-level transcription of genes cloned under control of a T7 promoter in systems optimized to efficiently translate the large amounts of RNA thus produced.

Uses of VLPs and VLP Populations

There are a number of possible uses for the VLPs and VLP populations of the present invention. As will be described in further detail below, the VLPs may be used as immunogenic compositions, particularly vaccines.

Immunogenic Compositions

As noted above, the VLPs of the present invention may be used to formulate immunogenic compositions, particularly vaccines. The vaccines should be in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition or disorder. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include complete and incomplete Freund's adjuvant, aluminum hydroxide, and modified muramyl dipeptide. Squalene has also been used as an adjuvant.

Optionally, the vaccine of the present invention additionally includes an adjuvant which can be present in either a minor or major proportion relative to the compound of the present invention.

EXAMPLES FIRST SET (Reference Set 1 Applies to these Examples)

The invention may be better understood by reference to the following non-limiting examples, which are provided as exemplary of the invention. The following examples are presented in order to more fully illustrate the preferred embodiments of the invention and should in no way be construed, however, as limiting the broad scope of the invention. References corresponding to numerical reference, citations are listed after the examples.

Materials and Methods

Bacteriophages PP7 and MS2.

MS2 and PP7 coat protein single-chain dimers are highly tolerant of peptide insertions and produce correctly assembled VLPs displaying the peptide insertion on the surface of VLP in a highly dense, repetitive array. These VLPs are highly immunogenic and confer this high immunogenicity to heterologous peptides displayed on their surfaces. Here we describe VLPs displaying a peptide antigens derived from the Human Papillomavirus (HPV) minor capsid protein, L2. Such recombinant VLPs serve as a prophylactic vaccine to prevent infection by diverse HPV strains.

The vaccines described below induced high titer antibody responses against L2 and protected against HPV challenge in a mouse model of infection. Similar techniques could also be used to construct MS2 VLPs that display L2 peptides.

The Plasmids pP7K and p2P7K32.

Overview of Plasmid Construction.

Two general kinds of plasmid were constructed for the synthesis of PP7 coat protein in *E coli* (see FIGS. 1 and 2). The first (pP7K and p2P7K32) expresses coat protein from the lac promoter and is used (in combination with pRZP7—see below) to assay for coat protein's tolerance of peptide insertions using translational repressor and VLP assembly assays. The second plasmid type (pETP7K and pET2P7K32) expresses the protein from the T7 promoter and transcription terminator. These plasmids produce large amounts of coat protein that assembles correctly into a VLP.

They also produce coat-specific mRNA with discrete 5'- and 3'-termini for encapsidation into VLPs.

Design of the peptide insertion site. The three-dimensional structure of the PP7 capsid shows that it is comprised of a coat protein whose tertiary structure closely mimics that of MS2, even though the amino acid sequences of the two proteins show only about 12% sequence identity (47). The PP7 protein possesses an AB-loop into which peptides may be inserted following a scheme similar to the one we described previously for MS2 (38). As in the MS2 case, mutation of the PP7 coat sequence to contain a site for the restriction endonuclease KpnI facilitates insertion of foreign sequences in the plasmids called pP7K and pETP7K (FIG. 1). This modification resulted in the amino acid substitution (E11T) shown in FIG. 3. This substitution was well tolerated, since the mutant coat protein represses translation and assembles correctly into a VLP. Again following the MS2 example, it was assumed that the folding of a single chain dimer version of PP7 coat protein would be more resistant to AB-loop insertions than the conventional dimer. Its construction was described previously (6). The single-chain dimer was modified to contain a KpnI site only in the downstream copy of the coding sequence, producing p2P7K32 and pET2P7K32 (FIG. 1). In this design, peptides can be inserted at amino acid 11, but it should be noted that other specific insertion sites are possible, including in the amino terminus, in the carboxy terminus or anywhere within the AB-loop of the coat polypeptide, preferably at amino acids 8-11 of the AB loop. Insertion or replacement of amino acids within the AB-loop (or the amino acid or carboxy terminus of the coat polypeptide, preferably within the downstream subunit of the coat polypeptide) may be used to accommodate the L2 peptide.

Example 1

Design of L2-Displaying PP7 VLPs

Figure 4:
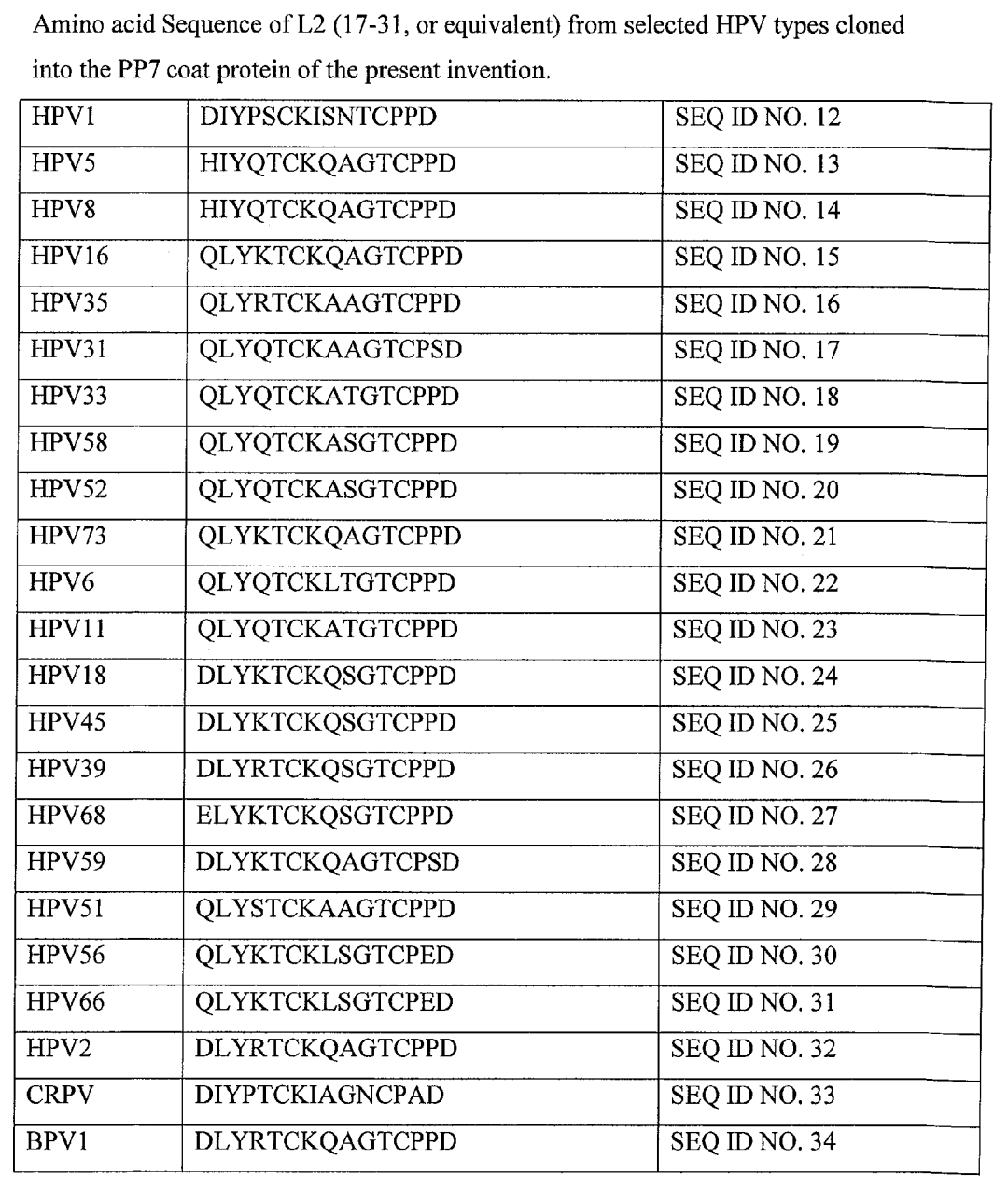

The construction of the expression plasmids p2P7K32 and pET2P7K32 have been described above. As explained, these plasmids code for the expression of a version of PP7 coat protein in which two copies of coat protein are genetically fused into a "single-chain" dimer. p2P7K32 and pET2P7K32 also contain a unique KpnI sites that allow for genetic insertion of sequences at amino acid 11 of the downstream copy of coat. To create the VLPs that display L2 peptides we designed PCR primers (shown in FIG. 2) that allowed us to clone L2-derived sequences into the AB-loop of PP7 coat. These sequences represented L2 amino acids 17-31 from different HPV isolates, including HPV16 (QLYKTCKQAGTCPPD) SEQ ID No. 15, HPV45 (DLYRTCKQSGTCPPD) SEQ ID No. 25, and HPV58 (QLYQTCKASGTCPPD) SEQ ID No. 19. This strategy was used to insert the corresponding L2 amino acids from other HPV types (shown in FIG. 2) into the PP7 single-chain dimer. The sequence of this region of L2 is relatively conserved across diverse HPV isolates (FIG. 4).

The functionality of coat protein encoded by the resulting plasmids (including, for example, p2P7-16L2 p2P7-45L2, and p2P7-58L2) was tested by two assays. First, we assessed the translational repression activity of recombinant PP7 coat proteins. PP7 coat normally functions as a translational repressor, shutting off synthesis of the viral replicase by binding to a specific RNA hairpin structure containing its ribosome-binding site (the translational operator). We described previously the construction of pRZP7, a plasmid that fuses the PP7 translational operator to the E. coli lacZ gene, thus placing β-galactosidase synthesis under control of coat protein's translational repressor activity (28). Because it confers resistance to a different antibiotic (chloramphenicol), and because it comes from a different incompatibility group (i.e. it uses the p15A replication origin), it can easily be maintained in the same E. coli strain as p2P7K32, which confers resistance to ampicillin and uses a colE1 origin. The expression of PP7 coat protein from p2P7K32 represses translation of β-galactosidase expressed from pRZP7. This makes it easy to determine whether a given peptide insertion has interfered with the ability of coat protein to correctly fold, since defective coat proteins give blue colonies on plates containing the β-galactosidase chromogenic substrate known as X-gal, whereas a properly functioning coat protein yields white colonies. All three recombinant coat proteins produced white colonies, indicating that the L2-recombinant coat proteins were functional.

Figure 5:
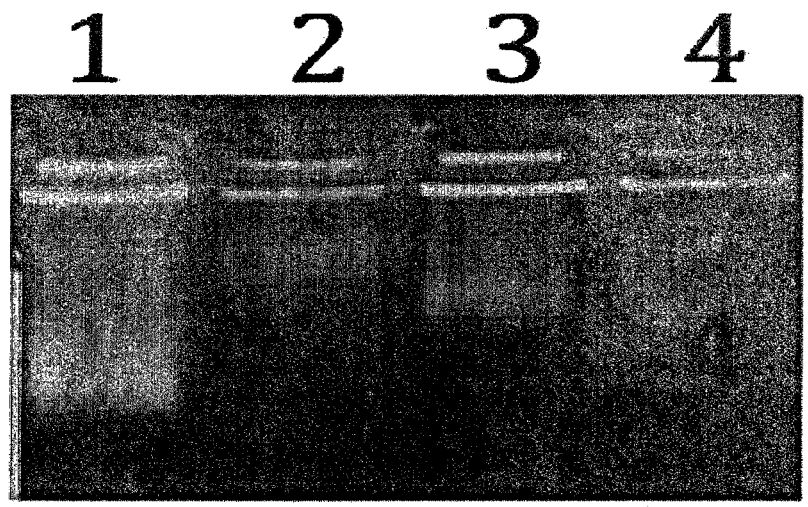
FIG. 5. Agarose gel electrophoresis of purified wild-type single-chain dimer (lane 1), 16L2 (lane 2), 45L2 (lane 3), and 58L2 (lane 4) VLPs. Variations in electrophoretic mobility reflect charge differences conferred by the inserted peptides.

Second, we assessed the presence of VLPs in lysates of cells expressing a peptide-coat protein recombinant by electrophoresis on agarose gel of cells lysed by sonication. Ethidium bromide staining detects the RNA-containing VLP, whose presence can be confirmed by western blot analysis using anti-PP7 serum. Electrophoresis of the VLPs in an agarose gel shows that each construct contains RNA (it stains with ethidium bromide) and exhibits an altered electrophoretic mobility due to charge differences conferred by the inserted peptides (FIG. 5). Thus, all three recombinant single-chain dimer coat proteins formed VLPs.

Example 2

L2 Peptides Displayed on PP7 VLPs are Displayed to the Immune System and are Immunogenic.

Overview.

In order to demonstrate that L2 peptides inserted into the PP7 AB-loop were indeed displayed on the surface of VLPs, we assessed the ability of a monoclonal antibody (mAb) RG-1; (20)) specific for the HPV16 L2 sequence to bind to recombinant 16L2-PP7 VLPs by ELISA. As shown in FIG. 6a, mAb RG-1 bound to 16L2-VLPs, but not to wild-type PP7 VLPs or PP7 VLPs that were modified to display the FLAG epitope (FLAG-VLPs). Moreover, as shown in FIG. 6b, mAb RG-1 bound to all eight of the L2-VLPs we produced, but not to wild-type PP7 VLPs.

Figure 7:
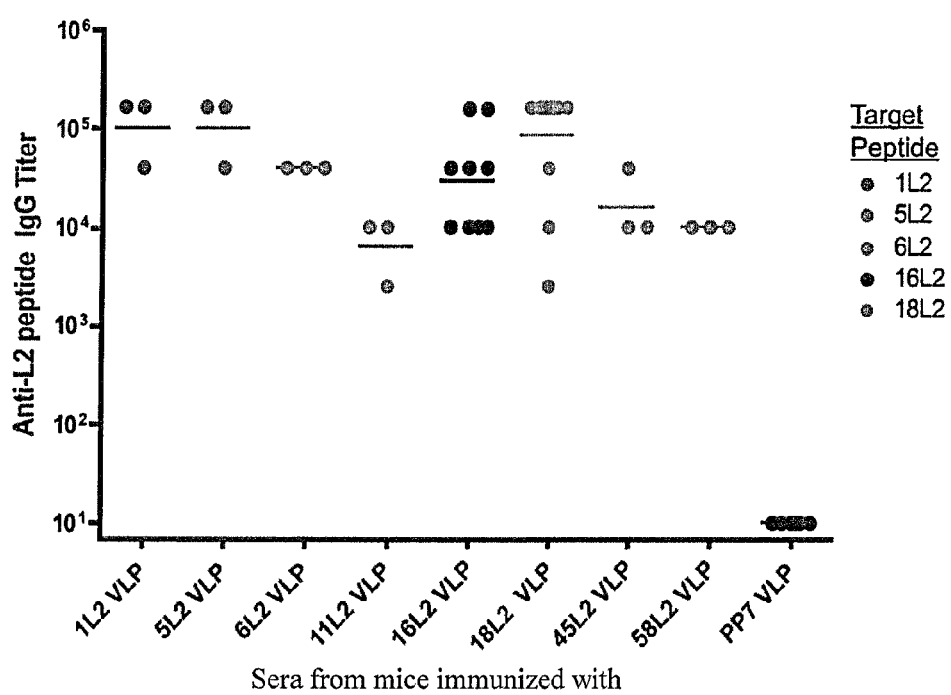
FIG. 7. IgG antibody responses in groups of mice immunized with wild-type PP7 VLPs, 1L2-VLPs, 5L2-VLPs, 6L2-VLPs, 11L2-VLPs, 16L2-VLPs, 18L2-VLPs, 45L2-VLPs, and 58L2VLPs. End-point dilution ELISA titers against a peptides representing amino acids 14-40 from the appropriate HPV L2 (shown in the key) conjugated to streptavidin. 10 µg of VLPs were administered intramuscularly in the presence of incomplete Freund's adjuvant. Results are from sera obtained three to four weeks after the second vaccination. Each datum point represents the antibody titer from an individual mouse. Lines represent the geometric mean titer for each group.

To test the immunogenicity of the VLPs, groups of three to nine mice were immunized with L2 displaying-VLPs or wild-type PP7 VLPs by intramuscular injection. Groups of three to nine mice were immunized intramuscularly with 10 μg of VLPs plus incomplete Freunds Adjuvant (IFA). All mice were boosted with the same amount of VLPs two weeks later. Sera were collected before each inoculation and weekly for three to four weeks after the boost. Sera from the mice were tested, by end-point dilution ELISA, for IgG antibodies specific for synthetic L2 peptides representing HPV1, 5, 6, 16, or 18 (FIG. 7). Mice immunized with 1L2-, 5L2-, 6L2-, 11L2-, 16L2-, 18L2-, 45L2-, and 58L2-VLPs generated high-titer (geometric mean titer typically >$10^4$) IgG responses against the corresponding peptide whereas no antibodies were detected in control mice. Thus, L2 peptides displayed on the surface of PP7 single-chain dimer VLPs display the high immunogenicity that is characteristic of other VLP-displayed antigens.

Example 3

PP7 VLPs Displaying a HPV16 L2 Peptide can Induce Neutralizing Antibodies that Protect Mice from Homologous and Heterologous Genital HPV Pseudovirus Challenge.

Overview.

The 16L2-VLP vaccine we designed contains amino acids 17-31 from HPV16 L2, a region shown to contain one or more highly cross-reactive neutralizing epitopes (1, 20), suggesting that the 16L2 VLPs could potentially protect against HPV challenge. We demonstrated that 16L2-VLPs could protect mice from HPV challenge using a HPV pseudovirus/mouse genital challenge model, first reported by Roberts and colleagues (40).

Additional Description.

The 16L2-VLP vaccine we designed contains amino acids 17-31 from HPV16 L2, a region shown to contain one or more highly cross-reactive neutralizing epitopes (1, 20), suggesting that the 16L2 VLPs could potentially protect against HPV challenge. We assessed whether 16L2-VLPs could protect mice from HPV challenge using a HPV pseudovirus/mouse genital challenge model, first reported by Roberts and colleagues (40). Groups of five Balb/c mice were given two intramuscular injections of HPV16 L1-VLPs, wild type PP7 VLPs, or 16L2-VLPs, or adjuvant (IFA) alone, and then, three weeks after the boost, challenged intravaginally with a high dose (~$10^8$ IU) of HPV pseudovirus carrying a luciferase reporter. As a negative control, mice were mock-challenged with PBS. Infection was detected as a bioluminescent signal two days after the administration of pseudovirions, immediately after intravaginal instillation of the challenged mice with the reporter substrate, luciferin.

Figure 8:
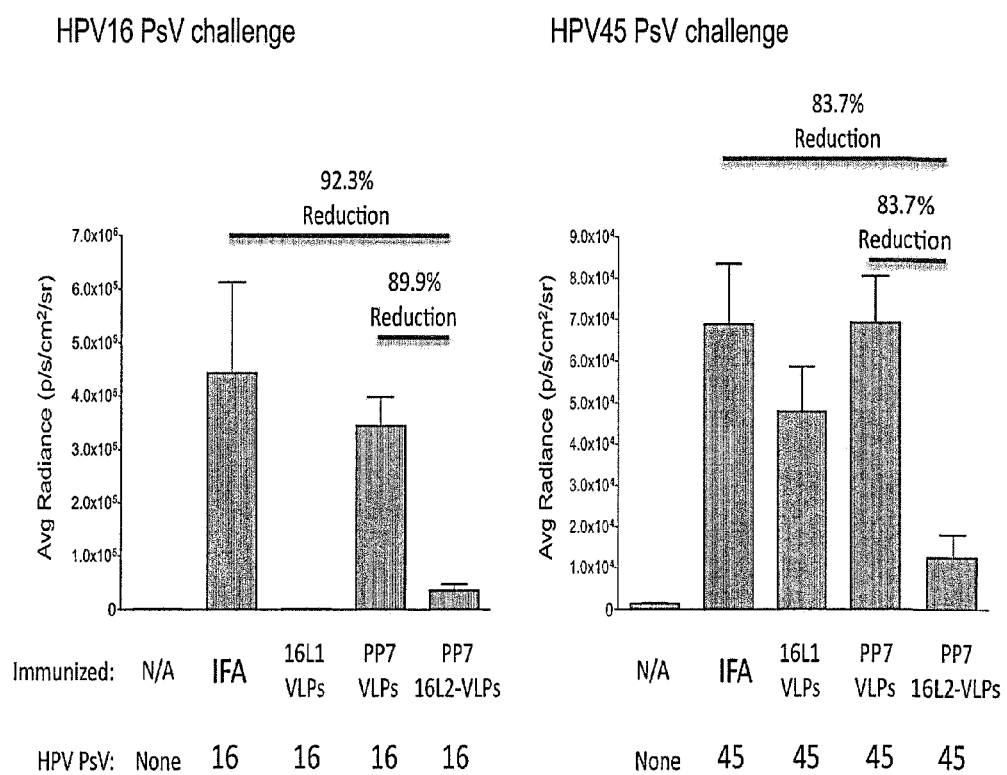
FIG. 8. Mice immunized with PP7 16L2-VLPs are protected from vaginal challenge with HPV16 or HPV45 pseudovirions. Groups of five mice were immunized two times with 10 µg 16L2-VLPs, wild-type PP7 VLPs, or HPV16 L1-VLPs formulated in incomplete Freund's adjuvant (IFA). As an additional control, mice were immunized with IFA alone. Three weeks after the second immunization mice were intravaginally challenged with $10^8$ IU of HPV16 pseudovirus (left panel) or HPV45 pseudovirus (right panel) containing a luciferase reporter. As a control, a group of five mice were not infected. Luciferase activity was quanititated 48 hours after infection by taking images 3 min post-installation of luciferin at medium binning with a 30-s exposure. Images were then analyzed by drawing an equally sized region of interest for each mouse and measuring average radiance (photons/second/cm$^2$/sr) within this region. Results shown are the mean average radiance for each group of five mice. Error bars represent the standard error of the mean. Lines above pairs of data indicate the percent reduction of signal in mice immunized with 16L2-VLPs relative to wild-type PP7 VLPs or the IFA control. All comparisons shown here are statistically significant ($p<0.01$) as calculated by T-test.

As shown in FIG. 8, mice immunized with 16L2-VLPs were strongly (~90%) protected from infection with the homologous pseudovirus, HPV16, whereas mice immunized with wild-type PP7 VLPs were not protected. We also tested whether vaccination with 16L2-VLPs could protect mice from genital infection with a heterologous HPV type. We chose HPV45 pseudovirus because it is not closely related to HPV16 and because its L2 (17-31) sequence varies from the HPV16 sequence at three of the fifteen amino acid positions. Immunization with HPV16 L1 VLPs did not protect mice from HPV45 challenge. However, 16L2-VLP-immunized mice were protected (~83%) from genital infection with HPV45 pseudovirus. Thus, 16L2-VLPs have potential as a pan-HPV vaccine.

Example 4

A Mixture of PP7 VLPs Displaying HPV L2 Peptides can Induce Antibodies that Protect Mice from Homologous and Heterologous Genital HPV Pseudovirus Challenge.

Figure 9:
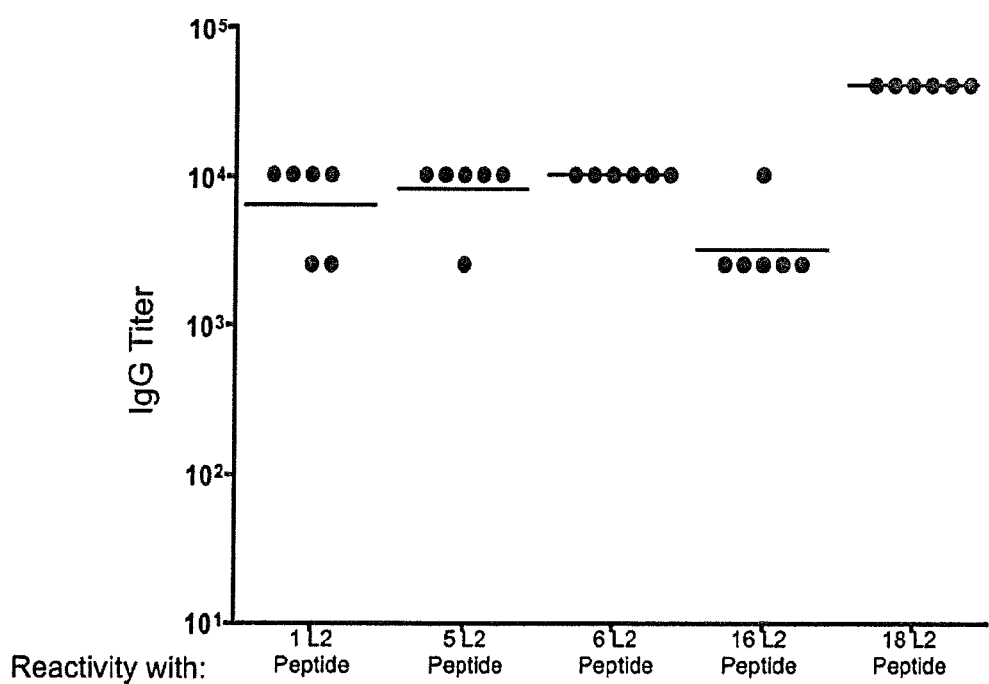
FIG. 9. Immunization with a mixture of L2-PP7 VLPs induces broad anti-L2 IgG responses. Mice were immunized three times without adjuvant with 10 µg (total) of a mixture of equal amounts of 1L2-VLPs, 5L2-VLPs, 6L2-VLPs, 11L2-VLPs, 16L2-VLPs, 18L2-VLPs, 45L2-VLPs, and 58L2VLPs. Two weeks after the final immunization, sera was taken as tested for reactivity to HPV L2 peptides representing L2 amino acids 14-40 from HPV1, HPV5, HPV6, HPV16, and HPV18 sequences.

We also tested the immunogenicity of a combination vaccine consisting of all eight L2-PP7 VLPs that were constructed. Groups of mice were immunized with a mixture of equal amounts of 1L2-VLPs, 5L2-VLPs, 6L2-VLPs, 11L2-VLPs, 16L2-VLPs, 18L2-VLPs, 45L2-VLPs, and 58L2VLPs. Mice were immunized three times at two-week intervals with a 10 μg dose and without exogenous adjuvant. Sera were collected before each inoculation and weekly for three to four weeks after the boost. Sera from the mice were tested, by end-point dilution ELISA, for IgG antibodies specific for synthetic L2 peptides representing HPV1, 5, 6, 16, or 18 (FIG. 9). Mice immunized with the mixture of L2-VLPs produced high-titer antibodies reactive with peptides representing 1L2, 5L2, 6L2, 11L2, 16L2, and 18L2. Thus, a mixture of L2-VLPs displayed on the surface of PP7 single-chain dimer VLPs is also highly immunogenic.

Figure 10:
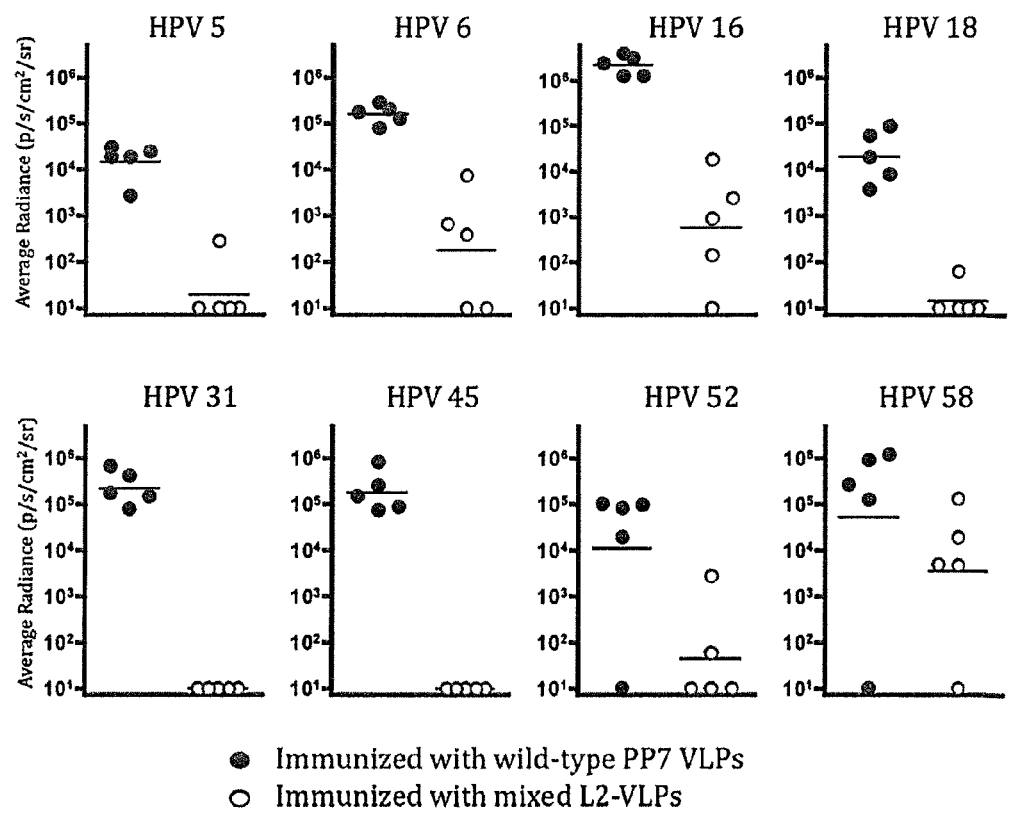
FIG. 10. Immunization with a mixture of L2-PP7 VLPs protects from genital infection with HPV5, HPV6, HPV16, HPV18, HPV31, HPV45, HPV52, and HPV58 pseudovirions. Groups of five mice were immunized three times with 10 µg (total) of a mixture of equal amounts of 1L2-VLPs, 5L2-VLPs, 6L2-VLPs, 11L2-VLPs, 16L2-VLPs, 18L2-VLPs, 45L2-VLPs, and 58L2VLPs. Two weeks after the final immunization, mice were challenged with $10^6$-$10^8$ IU of the indicated pseudovirus containing a luciferase reporter. As controls for each pseudovirus infection, groups of five mice were also immunized with wild-type PP7 VLPs. Luciferase activity was quanititated 48 hours after infection as described in FIG. 8. The extent of protection was determined by comparing the luciferase signal in the group immunized with control VLPs with the group immunized with mixed L2-VLPs.

We assessed whether the mixed L2-VLP vaccination could protect mice from HPV challenge using the HPV pseudovirus/mouse genital challenge model described above. Following immunization with the mixed L2-VLPs (as described above) or, as a negative control, wild-type PP7 VLPs, mice were challenged intravaginally with a high dose ($10^7$-$10^8$ IU) of HPV5, 6, 16, 18, 31, 45, 52, or 58 pseudovirus carrying a luciferase reporter. As shown in FIG. 10, immunization with mixed PP7 L2-VLPs protected mice from HPV5 pseudovirus infection (98.2% reduction in signal), HPV6 pseudovirus infection (98.6% reduction in signal), HPV16 pseudovirus infection (99.7% reduction in signal), HPV18 pseudovirus infection (99.1% reduction in signal), HPV31 pseudovirus infection (99.9% reduction), HPV45 pseudovirus infection (99.2% reduction), HPV52 pseudovirus infection (98.5% reduction in signal), and HPV58 pseudovirus infection (93.1% reduction in signal). Thus, mixed L2-VLPs also have potential as a pan-HPV vaccine.

Example 5

Other Regions of HPV L2 can be Displayed on the Surface of Bacteriophage VLPs and are Immunogenic.

Figure 11:
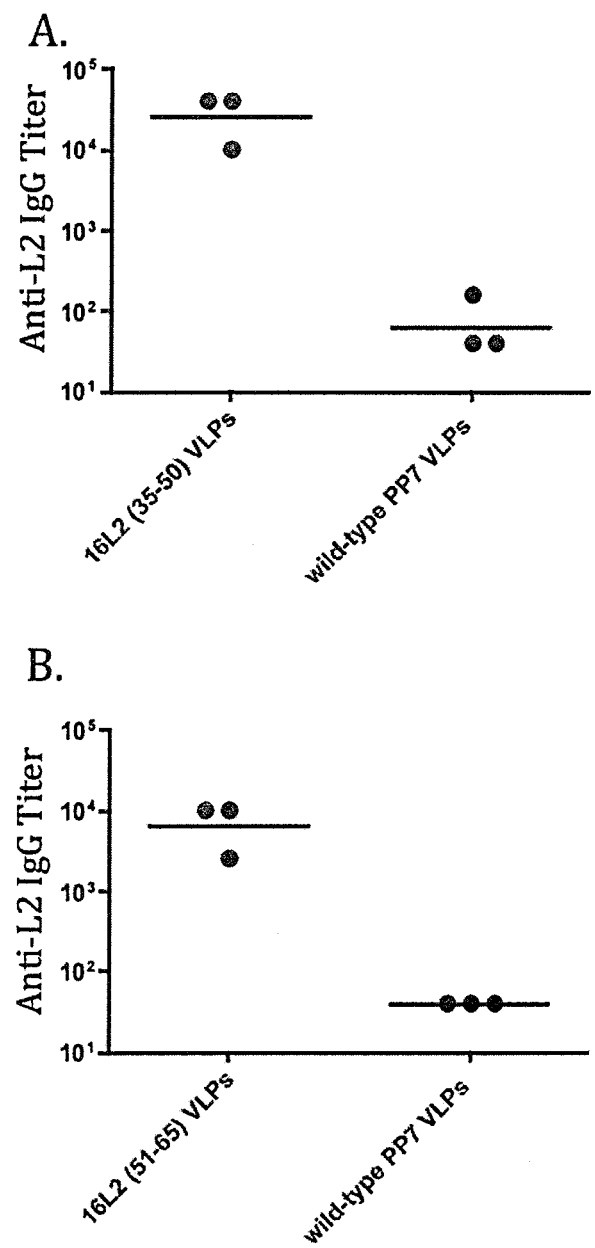
FIG. 11. Antibody responses in mice immunized with VLPs displaying HPV16 L2 amino acids 35-50 or 51-65. Mice were immunized three times and then sera was taken and tested for reactivity with synthetic peptides representing A) HPV16 L2 amino acids 34-52, and B) HPV16 L2 amino acids 49-71.

Using the methods described elsewhere in this application, we generated recombinant PP7 VLPs that display HPV16 L2 amino acids 35-50 (amino acid sequence: KVEGKTIADQILQYGS) SEQ ID No. 36 and amino acids 51-65 (sequence: MGVFFGGLGIGTGSG), SEQ ID No. 37. These VLPs were used to immunize mice, and, following two immunizations, antibodies against a synthetic peptides representing A) HPV16 L2 amino acids 34-52 or B) HPV16 L2 amino acids 49-71 were measured by end-point dilution ELISA. As shown in FIG. 11, both recombinant VLPs induced high-titer IgG antibodies that recognized the L2 peptides.

Example 6

Mice Immunized with 16L2 (17-31) Nterm MS2 VLPs Show Broader Protection from Infection with Diverse HPV PsV Types Compared to Those Immunized with 16L2 (17-31) AB-Loop PP7 VLPs.

Balb/c mice were immunized (intramuscularly) twice at two weeks intervals with 5 μg of 16L2 (17-31) Nterm MS2 VLPs or 16L2 (17-31) AB-loop PP7 VLPs or HPV16 L1L2 VLPs or a mixture of MS2/PP7 VLPs. Three to five weeks after the last immunization, mice were challenged with: A) PsV16 and B) PsV5, 6, 31, 33, 35, 39, 45, 51, 53, and PsV58. All challenges were done vaginally except PsV5, which was done intradermally. Forty-eight hours post-challenge, 0.4 mg of luciferin was administered via the same route used for PsV challenge and average radiance (p/s/cm$^2$/sr) values for each mouse was determined using Living Image 3.2 software. White-filled black circles (FIG. 12) represent mice immunized with MS2/PP7 VLPs, black-filled circles represent mice immunized with HPV16 L1L2 VLPs, blue-filled circles represent mice immunized with 16L2 (17-31) AB-loop PP7 VLPs, and red-filled circles represent mice immunized with 16L2 (17-31) Nterm MS2 VLPs. Black solid lines represent the geometric mean of average radiance. (52).

Additional Description.

Using the methods described elsewhere in this patent, L2 sequences were cloned specifically to be expressed in a constrained conformation within the AB loop and in an unconstrained conformation at the N-terminus of the coat protein. The differences are specifically related to the concept of constrained vs unconstrained conformation. In all cases, mice vaccinated with those VLPs that are comprised of the L2 sequence displayed in an unconstrained conformation are protected more broadly when challenged with diverse HPV PsV types.

EXAMPLES SECOND SET (Reference Set 2 Applies to these Examples)

Bacteriophages PP7 and MS2 and Related Plasmids.

Previously we described the use of virus-like particles of bacteriophage MS2 for peptide display. We established that MS2 coat protein single-chain dimers are highly tolerant of peptide insertions and that they produce correctly assembled VLPs that specifically encapsidate the mRNA encoding their synthesis (Peabody, D. S., Manifold-Wheeler, B., Medford, A., Jordan, S. K., do Carmo Caldeira, J., and Chackerian, B. (2008) *J Mol Biol* 380, 252-263). As explained above, MS2 is only one member of a large family of viruses whose individual members share similar molecular biology, e.g. PP7, a bacteriophage phage.

Experimental Overview.

As explained above, we have previously described the use of VLPs of two RNA bacteriophages, MS2 and PP7, for peptide display. MS2 and PP7 coat protein single-chain dimers are highly tolerant of peptide insertions and produce correctly assembled VLPs displaying the peptide insertion on the surface of VLP in a highly dense, repetitive array. These VLPs are highly immunogenic and confer this high immunogenicity to heterologous peptides displayed on their surfaces. Here we also describe VLPs displaying a peptide antigens derived from the Human Papillomavirus (HPV) minor capsid protein, L2. Such recombinant VLPs serve as a prophylactic vaccine to prevent infection by diverse HPV strains. The vaccines described below induced high titer antibody responses against L2 and protected mice against infection with diverse HPV pseudoviruses.

Example 1

As noted above, current HPV vaccines are based on VLPs comprised of the viral major capsid protein L1. Although L1-VLP vaccines are highly effective, they are type-specific, meaning that the current HPV vaccines only provide protection against a small subset of the more than 100 types of HPVs that infect humans, including the 15-18 HPV types that are carcinogenic. In contrast, the HPV minor capsid protein, L2, contains broadly cross-neutralizing epitopes. Antibodies that are specific for these highly conserved epitopes within L2 are able to neutralize infection by a broad range of HPV types (7). Therefore, a vaccine targeting L2 might provide more comprehensive protection against infection by multiple HPV types. Unlike L1, the L2 protein does not assemble into VLPs on its own, and is therefore not very immunogenic, meaning that it is difficult to induce high titer antibodies against it.

We constructed and established the utility of VLP-based vaccines targeting the HPV L2 protein. The data below describes the construction of recombinant MS2 VLPs that display L2 peptides. These vaccines induce high titer antibody responses against L2 and protect against HPV challenge in a mouse model of infection. Similar techniques could also be used to construct PP7 VLPs that display L2 peptides.

Figure 18:
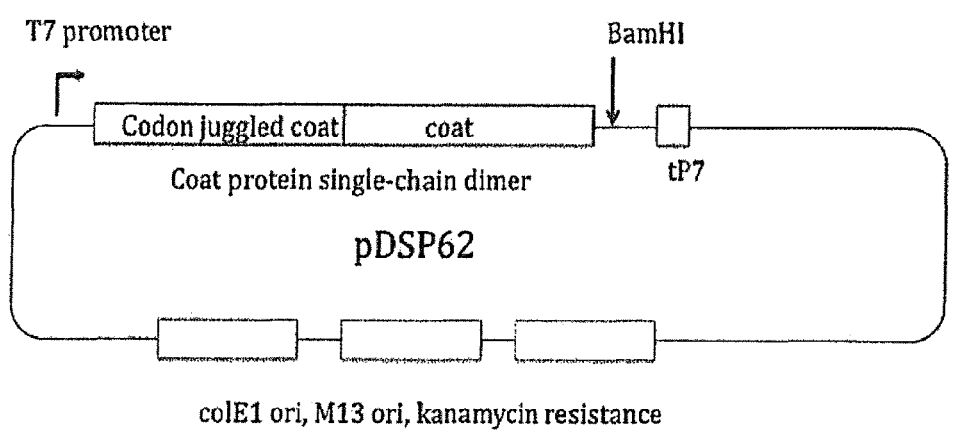
FIG. 18 depicts the pDSP62 plasmid.

Design of L2 Displaying VLPs:

As noted above, we described previously the construction of the expression plasmid pDSP62 and pDSP1 (3) (FIGS. 18 and 19). This plasmid codes for the expression of a version of MS2 coat protein in which two copies of coat protein are genetically fused into a "single-chain" dimer. These plasmids contain a unique NcoI restriction site that allows for genetic insertion of sequences at the N-terminus of the single-chain dimer. To create the VLPs that display L2 peptides we designed PCR primers that allowed us to clone three HPV16 L2-derived sequences onto the N-terminus of coat protein. These sequences represented L2 amino acids 20-29, 17-31, and 14-40 from HPV16. The primers used to create these constructs and the amino acid sequences of these insertions are shown in FIG. 13.

Figure 14:
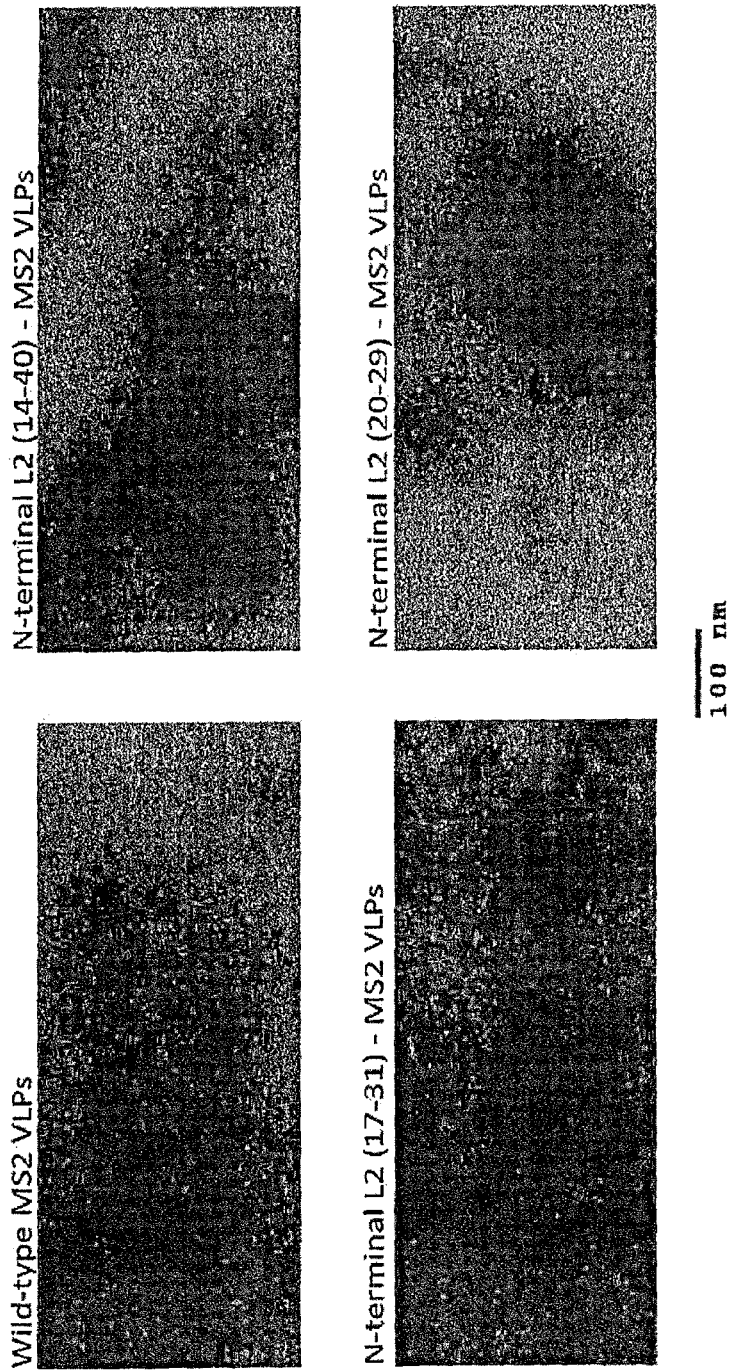
FIG. 14 depicts transmission electron micrographs of wild-type and recombinant MS2 VLPs

Modified pDSP62 containing the recombinant sequences was used to express recombinant VLPs in *E. coli*. Following our standard procedures for expression and purification, recombinant VLPs were visualized by transmission electron microscopy. As shown in FIG. 14, all three recombinant coat proteins formed VLPs.

L2 Peptides Displayed on MS2 VLPs are Immunogenic.

Figure 15:
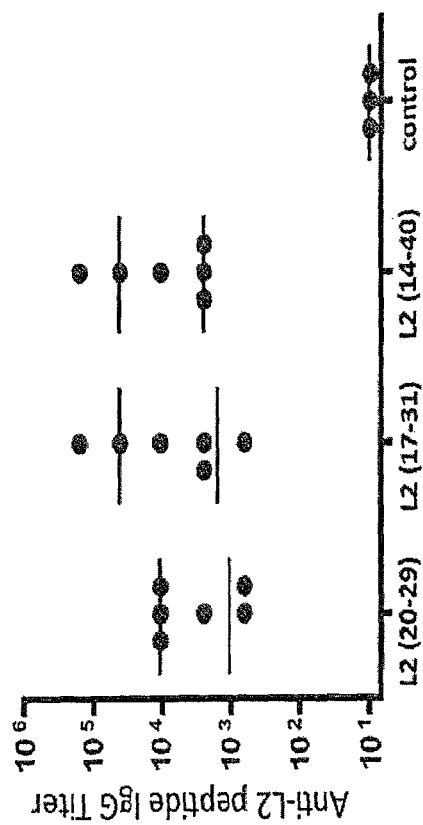
FIG. 15 shows the IgG antibody responses in groups of mice immunized with wild-type MS2 VLPs (controls) or MS2 VLPs displaying L2 peptides (20-29), (17-31), or (14-40). Titers were calculated against a peptide representing amino acids 14-40 from HPV16 L2 conjugated to streptavidin. Results are from sera obtained one week after the initial vaccination (red) or one week after the boost (black). Each datum point represents the antibody titer from an individual mouse. Lines represent the geometric mean titer for each group. As indicated, mice were immunized i.m. with 5 µg of VLPs without exogenous adjuvant. Shown are end-point dilution ELISA titers against an HPV16 L2 (14-40) peptide after one or two immunizations.
Figure 16:
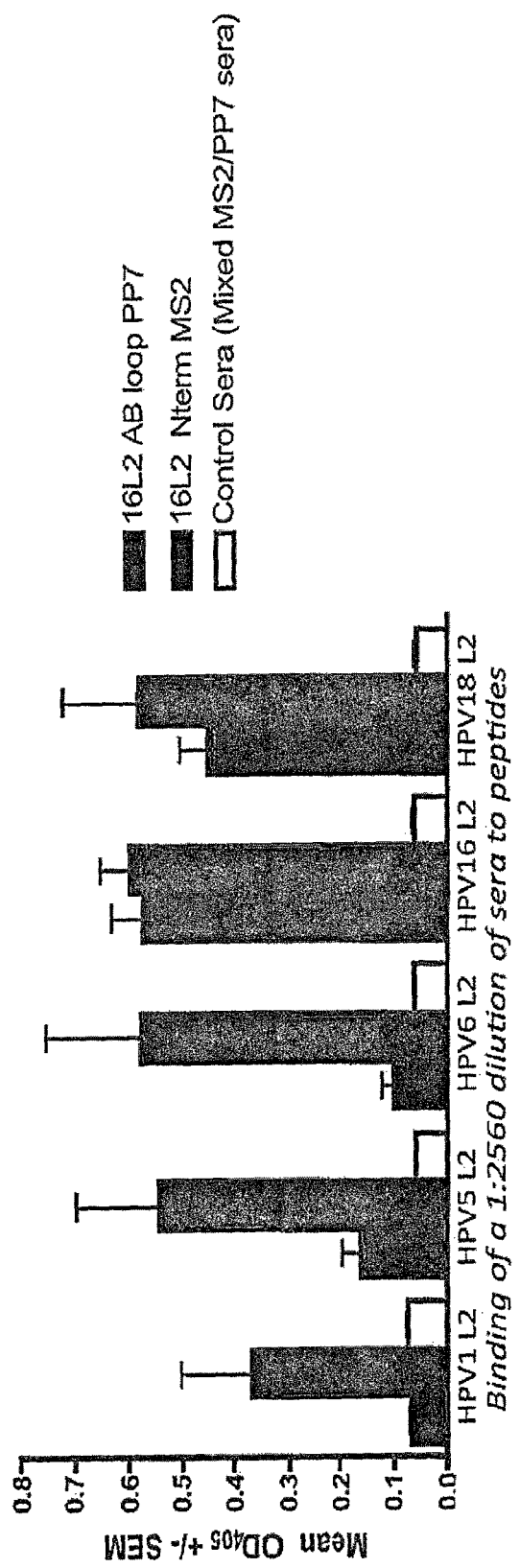
FIG. 16 shows the cross-reactivity of sera elicited upon immunization with 16L2(17-31) displayed either at the N-terminus of MS2 coat protein or in the AB-loop of PP7. ELISA plates were coated with the streptavidin-conjugated L2 peptides representing HPV1, 5, 6, 16, & 18 and reacted with a 1:2560 dilution of serum from mice. Shown are the averages of the optical density ($OD_{405}$) values of sera from three individual mice in each group. Error bars represent SEM. As show, VLps displaying the HPV16 L2 sequence at the N-terminus induce more broadly cross-reactive antibody responses.

To test the immunogenicity of the VLPs, mice were immunized with 16L2-VLPs or wild-type MS2 VLPs by intramuscular injection. Groups of three mice were immunized intramuscularly with 10 μg of VLPs without any exogenous adjuvant. All mice were boosted with the same amount of VLPs two weeks later. Sera were collected one week after each inoculation. Sera from the mice were tested, by end-point dilution ELISA, for IgG antibodies specific for the 16L2 peptide (FIG. 15). As shown, mice immunized with all three 16L2-VLPs generated high-titer (geometric mean titer>$10^4$) IgG responses against the corresponding peptide whereas no antibodies were detected in control mice. Thus, L2 peptides displayed on the surface of MS2 single-chain dimer VLPs display the high immunogenicity that is characteristic of other VLP-displayed antigens.

PP7 VLPs Displaying a HPV16 L2 Peptide can Induce Neutralizing Antibodies that Protect Mice from Homologous and Heterologous Genital HPV Pseudovirus Challenge.

The 16L2-VLP vaccine we designed contains amino acids 17-31 from HPV16 L2, a region shown to contain one or more highly cross-reactive neutralizing epitopes (1, 5), suggesting that the 16L2 VLPs could elicit antibodies that broadly cross-react with L2 sequences from other HPV strain and could potentially protect against HPV challenge. First, we assessed whether the sera from mice immunized with recombinant MS2 VLPs displaying HPV16 L2 (17-31) at the N-terminus could cross-react with peptide representing L2 amino acids 14-40 from five HPV strains (HPV1, 5, 6, 16, & 18). As shown in FIG. 4, this sera was broadly cross-reactive, reacting with all five peptides. Unexpectedly, sera from mice immunized with PP7 VLPs displaying the same HPV16 L2 peptide in the AB-loop was much less broadly cross-reactive.

Figure 17:
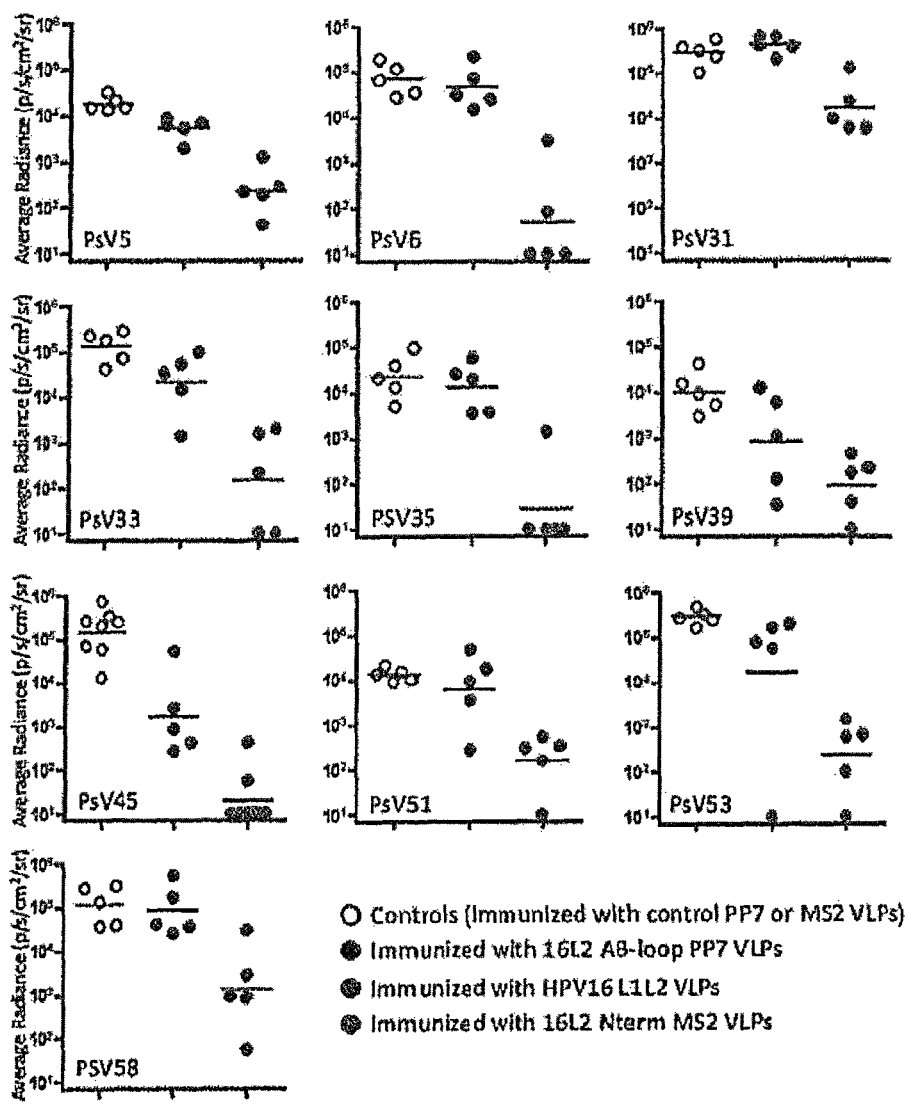
FIG. 17 shows that mice immunized with 16L2 (17-31) displayed either the N-terminus of MS2 coat protein show broader protection from infection with diverse HPV PsV types compared to those immunized with 16L2 (17-31) AB-loop PP7 VLPs. Balb/c mice were immunized (intramuscularly) twice at two weeks intervals with 5 µg of 16L2 (17-31) Nterm MS2 VLPs or 16L2 (17-31) AB-loop PP7 VLPs or HPV16 L1L2 VLPs or a mixture of MS2/PP7 VLPs. Three to five weeks after the last immunization, mice were challenged with: A) PsV16 and B) PsV5, 6, 31, 33, 35, 39, 45, 51, 53, and PsV58. All challenges were done vaginally except PsV5, which was done intradermally. Forty-eight hours post-challenge, 0.4 mg of luciferin was administered via the same route used for PsV challenge and average radiance (p/s/cm$^2$/sr) values for each mouse was determined using Living Image 3.2 software. White-filled black circles represent mice immunized with MS2/PP7 VLPs, black-filled circles represent mice immunized with HPV16 L1L2 VLPs, blue-filled circles represent mice immunized with 16L2 (17-31) AB-loop PP7 VLPs, and red-filled circles represent mice immunized with 16L2 (17-31) Nterm MS2 VLPs. Black solid lines represent the geometric mean of average radiance.

To determine whether the broader cross-reactivity observed with the insertion of epitope 17-31 at the N-terminus of MS2 coat protein correlated with protection, mice were immunized with VLPs displaying the HPV16 L2 epitope at either the N-terminus of MS2 coat protein [16L2 (17-31) Nterm MS2 VLPs] or at the AB-loop of PP7 coat protein [16L2 (17-31) AB-loop PP7 VLPs] or control VLPs, and were then challenged with a panel of HPV pseudoviruses (PsVs) (PsV5, 6, 16, 31, 33, 35, 39, 45, 51, 53, and 58) three to five weeks after the $2^{nd}$ immunization. As expected, mice immunized with either 16L2 (17-31) Nterm MS2 VLPs or 16L2 (17-31) AB-loop PP7 VLPs showed almost complete protection from high-dose vaginal challenge with homologous HPV16 PsV (FIG. 17A). Protection was similar to mice immunized with HPV16 L1L2 VLPs. However, there were dramatic differences in protection from heterologous HPV PsV challenge (FIG. 17B) Immunization with L2-PP7 VLPs resulted in modest or no protection against heterologous PsV. In contrast, immunization with L2-MS2 VLPs resulted in significant protection from vaginal challenge with nine heterologous types and one intradermal challenge with HPV5 PsV. We observed very strong (80- to 7,190-fold reduction in signal) protection from infection with 9 out of the heterologous PsV types tested. Protection from HPV31 PsV was somewhat weaker (17-fold), but still statistically significant ($p<0.01$, one-tailed t-test). Thus, immunization with MS2 VLPs displaying a single HPV16 L2 peptide provided protection against diverse HPV pseudovirus types.

Our experiments showed that there were dramatic differences in protection from heterologous HPV PsV challenge. See FIG. 20. Immunization with L2-PP7 VLPs resulted in modest or no protection against heterologous PsV. In contrast, immunization with N-terminal displayed L2-MS2 VLPs according to the present invention resulted in significant protection from vaginal challenge with nine heterologous types and one intradermal challenge with HPV5 PsV. We observed very strong (about 80- to 7,190-fold reduction in signal) protection from infection with 9 out of the 10 heterologous PsV types tested, an unexpected result. This protection was surprisingly substantially stronger than what was observed in mice immunized with AB-loop displayed L2. Consequently our experimental results evidenced that protection against homologous challenge using VLPs according to the present invention is generally at least about 5-10-fold greater than VLPs where an antigenic L2 peptide is inserted into the AB-loop. In particular, protection against heterologous challenge was shown to be 10-25-fold (HPV5, 31 & 39), 40-100-fold (HPV45, 51, 53, & 58), or 140-1000-fold (HPV6, 33, & 35) better using the N-terminal VLP construct.

Summary.

Genetic display of peptides on PP7 VLPs is well suited for the precise targeting of specific B-cell epitopes known to be the target of neutralizing antibodies. For many pathogens, including influenza (4, 12), Hepatitis C Virus (8), and HIV (2), the target epitopes of broadly neutralizing antibodies are poorly immunogenic, meaning that full-length proteins are inadequate for the induction of antibody responses by vaccination. On the other hand, the use of peptide epitopes as vaccines is limited because of their poor immunogenicity unless coupled to carrier proteins. The PP7 and MS2 VLP platforms that we have described allow for targeted introduction of specific peptide epitopes in a highly immunogenic context. In this example, we targeted a broadly neutralizing epitope near the N-terminus of the HPV16 L2 protein. This epitope is the target of an HPV neutralizing monoclonal antibody (5), and it was already shown that the corresponding synthetic peptide, when linked to a carrier protein, can elicit cross-neutralizing antibodies against HPV (1). We show that MS2 VLPs displaying the L2 epitope at the N-terminus of the bacteriophage coat protein induce high-titer peptide-specific antibodies, and the antibodies were of high enough titer to provide almost complete protection of mice from genital challenge with homologous (HPV16) as well as heterologous (HPV5, 6, 31, 33, 35, 39, 45, 51, 53, and 58) pseudovirus. Thus, MS2 VLPs show utility for the targeted induction of antibodies against specific epitopes.

REFERENCES

Reference Set 1 (For Examples First Set)
1. Alphs, H. H., R. Gambhira, B. Karanam, J. N. Roberts, S. Jagu, J. T. Schiller, W. Zeng, D. C. Jackson, and R. B. Roden. 2008. Protection against heterologous human papillomavirus challenge by a synthetic lipopeptide vaccine containing a broadly cross-neutralizing epitope of L2. Proc Natl Acad Sci USA 105:5850-5.
2. Bachmann, M. F., U. H. Rohrer, T. M. Kundig, K. Burki, H. Hengartner, and R. M. Zinkernagel. 1993. The influence of antigen organization on B cell responsiveness. Science 262:1448-1451.
3. Bachmann, M. F., and R. M. Zinkernagel. 1997. Neutralizing antiviral B cell responses. Annu Rev Immunol 15:235-70.
4. Brunswick, M., F. D. Finkelman, P. F. Highet, J. K. Inman, H. M. Dintzis, and J. J. Mond. 1988. Picogram quantities of anti-Ig antibodies coupled to dextran induce B cell proliferation. J Immunol 140:3364-72.
5. Buck, C. B., N. Cheng, C. D. Thompson, D. R. Lowy, A. C. Steven, J. T. Schiller, and B. L. Trus. 2008. Arrangement of L2 within the papillomavirus capsid. J Virol 82:5190-7.
6. Caldeira, J. C., and D. S. Peabody. 2007. Stability and assembly in vitro of bacteriophage PP7 virus-like particles. J Nanobiotechnology 5:10.
7. Campo, M. S., G. J. Grindlay, B. W. O'Neil, L. M. Chandrachud, G. M. McGarvie, and W. F. Jarrett. 1993. Prophylactic and therapeutic vaccination against a mucosal papillomavirus. J Gen Virol.
8. Chackerian, B., L. Briglio, P. S. Albert, D. R. Lowy, and J. T. Schiller. 2004. Induction of autoantibodies to CCR5 in macaques and subsequent effects upon challenge with an R5-tropic simian/human immunodeficiency virus. J Virol 78:4037-47.
9. Chackerian, B., M. R. Durfee, and J. T. Schiller. 2008. Virus-like display of a neo-self antigen reverses B cell anergy in a B cell receptor transgenic mouse model. J Immunol 180:5816-25.
10. Chackerian, B., D. R. Lowy, and J. T. Schiller. 2001. Conjugation of a self-antigen to papillomavirus-like particles allows for efficient induction of protective autoantibodies. J Clin Invest 108:415-23.
11. Chackerian, B., D. R. Lowy, and J. T. Schiller. 1999. Induction of autoantibodies to mouse CCR5 with recombinant papillomavirus particles. Proc. Natl. Acad. Sci. USA 96:2373-2378.
12. Chackerian, B., M. Rangel, Z. Hunter, and D. S. Peabody. 2006. Virus and virus-like particle-based immunogens for Alzheimer's disease induce antibody responses against amyloid-beta without concomitant T cell responses. Vaccine 24:6321-31.
13. Christensen, N. D., J. W. Kreider, N. C. Kan, and S. L. DiAngelo. 1991. The open reading frame L2 of cottontail rabbit papillomavirus contains antibody-inducing neutralizing epitopes. Virology 181:572-9.
14. Cornuz, J., S. Zwahlen, W. F. Jungi, J. Osterwalder, K. Klingler, G. van Melle, Y. Bangala, I. Guessous, P. Muller, J. Willers, P. Maurer, M. F. Bachmann, and T. Cerny. 2008. A vaccine against nicotine for smoking cessation: a randomized controlled trial. PLoS ONE 3:e2547.
15. Day, P. M., R. Gambhira, R. B. Roden, D. R. Lowy, and J. T. Schiller. 2008. Mechanisms of human papillomavirus type 16 neutralization by 12 cross-neutralizing and 11 type-specific antibodies. J Virol 82:4638-46.

16. Dintzis, H. M., R. Z. Dintzis, and B. Vogelstein. 1976. Molecular determinants of immunogenicity: the immunon model of immune response. Proc Natl Acad Sci USA 73:3671-5.
17. Dintzis, R. Z., M. H. Middleton, and H. M. Dintzis. 1985. Inhibition of anti-DNP antibody formation by high doses of DNP-polyacrylamide molecules; effects of hapten density and hapten valence. J Immunol 135:423-7.
18. Fehr, T., D. Skrastina, P. Pumpens, and R. M. Zinkernagel. 1998. T cell-independent type I antibody response against B cell epitopes expressed repetitively on recombinant virus particles. Proc Natl Acad Sci USA 95:9477-81.
19. Gambhira, R., S. Jagu, B. Karanam, P. E. Gravitt, T. D. Culp, N. D. Christensen, and R. B. Roden. 2007. Protection of rabbits against challenge with rabbit papillomaviruses by immunization with the N terminus of human papillomavirus type 16 minor capsid antigen L2. J Virol 81:11585-92.
20. Gambhira, R., B. Karanam, S. Jagu, J. N. Roberts, C. B. Buck, I. Bossis, H. Alphs, T. Culp, N. D. Christensen, and R. B. Roden. 2007. A protective and broadly cross-neutralizing epitope of human papillomavirus L2. J Virol 81:13927-31.
21. Ghim, S. J., A. B. Jenson, and R. Schlegel. 1992. HPV-1 L1 protein expressed in cos cells displays conformational epitopes found on intact virions. Virology 190:548-52.
22. Harro, C. D., Y. Y. Pang, R. B. Roden, A. Hildesheim, Z. Wang, M. J. Reynolds, T. C. Mast, R. Robinson, B. R. Murphy, R. A. Karron, J. Dillner, J. T. Schiller, and D. R. Lowy. 2001. Safety and immunogenicity trial in adult volunteers of a human papillomavirus 16 L1 virus-like particle vaccine. J Natl Cancer Inst 93:284-92.
23. Kawana, K., Y. Kawana, H. Yoshikawa, Y. Taketani, K. Yoshiike, and T. Kanda. 2001. Nasal immunization of mice with peptide having a cross-neutralization epitope on minor capsid protein L2 of human papillomavirus type 16 elicit systemic and mucosal antibodies. Vaccine 19:1496-502.
24. Kirnbauer, R., F. Booy, N. Cheng, D. R. Lowy, and J. T. Schiller. 1992. Papillomavirus L1 major capsid protein self-assembles into virus-like particles that are highly immunogenic. Proc Natl Acad Sci USA 89:12180-12184.
25. Kirnbauer, R., J. Taub, H. Greenstone, R. B. S. Roden, M. Durst, L. Gissmann, D. R. Lowy, and J. T. Schiller. 1993. Efficient self-assembly of human papillomavirus type 16 L1 and L1-L2 into virus-like particles. J Virol 67:6929-6936.
26. Koutsky, L. A., K. A. Ault, C. M. Wheeler, D. R. Brown, E. Barr, F. B. Alvarez, L. M. Chiacchierini, and K. U. Jansen. 2002. A controlled trial of a human papillomavirus type 16 vaccine. N Engl J Med 347:1645-51.
27. Li, Q., C. Cao, B. Chackerian, J. Schiller, M. Gordon, K. E. Ugen, and D. Morgan. 2004. Overcoming antigen masking of anti-amyloidbeta antibodies reveals breaking of B cell tolerance by virus-like particles in amyloidbeta immunized amyloid precursor protein transgenic mice. BMC Neurosci 5:21.
28. Lim, F., T. P. Downey, and D. S. Peabody. 2001. Translational repression and specific RNA binding by the coat protein of the *Pseudomonas* phage PP7. J Biol Chem 276:22507-13.
29. Lim, F., and D. S. Peabody. 2002. RNA recognition site of PP7 coat protein. Nucleic Acids Res 30:4138-44.
30. Lin, Y.-L., L. A. Borenstein, R. Selvakumar, R. Ahmed, and F. O. Wettstein. 1992. Effective vaccination against papilloma development by immunization with L1 or L2 structural protein of cottontail rabbit papillomavirus. Virology 187:612-619.
31. Mao, C., L. A. Koutsky, K. A. Ault, C. M. Wheeler, D. R. Brown, D. J. Wiley, F. B. Alvarez, O. M. Bautista, K. U. Jansen, and E. Barr. 2006. Efficacy of human papillomavirus-16 vaccine to prevent cervical intraepithelial neoplasia: a randomized controlled trial. Obstet Gynecol 107:18-27.
32. Milich, D. R., M. Chen, F. Schodel, D. L. Peterson, J. E. Jones, and J. L. Hughes. 1997. Role of B cells in antigen presentation of the hepatitis B core. Proc Natl Acad Sci USA 94:14648-53.
33. Munoz, N., F. X. Bosch, S. de Sanjose, R. Herrero, X. Castellsague, K. V. Shah, P. J. Snijders, and C. J. Meijer. 2003. Epidemiologic classification of human papillomavirus types associated with cervical cancer. N Engl J Med 348:518-27.
34. Parkin, D. M., and F. Bray. 2006. Chapter 2: The burden of HPV-related cancers. Vaccine 24 Suppl 3:S3/11-25.
35. Pastrana, D. V., C. B. Buck, Y. Y. Pang, C. D. Thompson, P. E. Castle, P. C. FitzGerald, S. Kruger Kjaer, D. R. Lowy, and J. T. Schiller. 2004. Reactivity of human sera in a sensitive, high-throughput pseudovirus-based papillomavirus neutralization assay for HPV16 and HPV18. Virology 321:205-16.
36. Pastrana, D. V., R. Gambhira, C. B. Buck, Y. Y. Pang, C. D. Thompson, T. D. Culp, N. D. Christensen, D. R. Lowy, J. T. Schiller, and R. B. Roden. 2005. Cross-neutralization of cutaneous and mucosal Papillomavirus types with anti-sera to the amino terminus of L2. Virology 337:365-72.
37. Peabody, D. S. 1990. Translational repression by bacteriophage MS2 coat protein expressed from a plasmid. A system for genetic analysis of a protein-RNA interaction. Biol Chem 265:5684-9.
38. Peabody, D. S., B. Manifold-Wheeler, A. Medford, S. K. Jordan, J. do Carmo Caldeira, and B. Chackerian. 2008. Immunogenic display of diverse peptides on virus-like particles of RNA phage MS2. J Mol Biol 380:252-63.
39. Richards, R. M., D. R. Lowy, J. T. Schiller, and P. M. Day. 2006. Cleavage of the papillomavirus minor capsid protein, L2, at a furin consensus site is necessary for infection. Proc Natl Acad Sci USA 103:1522-7.
40. Roberts, J. N., C. B. Buck, C. D. Thompson, R. Kines, M. Bernardo, P. L. Choyke, D. R. Lowy, and J. T. Schiller. 2007. Genital transmission of HPV in a mouse model is potentiated by nonoxynol-9 and inhibited by carrageenan. Nat Med 13:857-61.
41. Roden, R. B., W. I. Yutzy, R. Fallon, S. Inglis, D. R. Lowy, and J. T. Schiller. 2000. Minor capsid protein of human genital papillomaviruses contains subdominant, cross-neutralizing epitopes. Virology 270:254-7.
42. Roden, R. B. S., N. L. Hubbert, R. Kirnbauer, N. D. Christensen, D. R. Lowy, and J. T. Schiller. 1996. Assessment of the serological relatedness of genital human papillomaviruses by hemagglutination inhibition. J Virol 70:3298-3301.
43. Rose, R. C., W. Bonnez, R. C. Reichman, and R. L. Garcea. 1993. Expression of human papillomavirus type 11 L1 protein in insect cells: in vivo and in vitro assembly of viruslike particles. J Virol 67:1936-44.
44. Schiller, J. T., and D. R. Lowy. 2001. Papillomavirus-like particle based vaccines: cervical cancer and beyond. Expert Opin Biol Ther 1:571-81.

45. Selinka, H. C., T. Giroglou, T. Nowak, N. D. Christensen, and M. Sapp. 2003. Further evidence that papillomavirus capsids exist in two distinct conformations. J Virol 77:12961-7.
46. Stanley, M., D. R. Lowy, and I. Frazer. 2006. Chapter 12: Prophylactic HPV vaccines: underlying mechanisms. Vaccine 24 Suppl 3:S3/106-13.
47. Tars, K., K. Fridborg, M. Bundule, and L. Liljas. 2000. The three-dimensional structure of bacteriophage PP7 from *Pseudomonas aeruginosa* at 3.7-A resolution. Virology 272:331-7.
48. Thyagarajan, R., N. Arunkumar, and W. Song. 2003. Polyvalent antigens stabilize B cell antigen receptor surface signaling microdomains. J Immunol 170:6099-106.
49. Tissot, A. C., P. Maurer, J. Nussberger, R. Sabat, T. Pfister, S. Ignatenko, H. D. Volk, H. Stocker, P. Muller, G. T. Jennings, F. Wagner, and M. F. Bachmann. 2008. Effect of immunisation against angiotensin II with CYT006-AngQb on ambulatory blood pressure: a double-blind, randomised, placebo-controlled phase IIa study. Lancet 371:821-7.
50. Zhang, L. F., J. Zhou, S. Chen, L. L. Cai, Q. Y. Bao, F. Y. Zheng, J. Q. Lu, J. Padmanabha, K. Hengst, K. Malcolm, and I. H. Frazer. 2000. HPV6b virus like particles are potent immunogens without adjuvant in man. Vaccine 18:1051-8.
51. Zhou, J., X. Y. Sun, D. J. Stenzel, and I. H. Frazer. 1991. Expression of vaccinia recombinant HPV16 L1 and L2 ORF proteins in epithelial cells is sufficient for assembly of HPV virion-like particles. Virology 185:251-257.
52. Tumban E, Peabody J, Tyler M, Peabody D S, Chackerian B (2012) VLPs Displaying a Single L2 Epitope Induce Broadly Cross-Neutralizing Antibodies against Human Papillomavirus. PLOS ONE 7 (11): e49751. doi: 10.1371/journal.pone.0049751

Reference Set 2 (For Examples Second Set)
1. Alphs, H. H., R. Gambhira, B. Karanam, J. N. Roberts, S. Jagu, J. T. Schiller, W. Zeng, D. C. Jackson, and R. B. Roden. 2008. Protection against heterologous human papillomavirus challenge by a synthetic lipopeptide vaccine containing a broadly cross-neutralizing epitope of L2. Proc Natl Acad Sci USA 105:5850-5.
2. Burton, D. R., R. L. Stanfield, and I. A. Wilson. 2005. Antibody vs. HIV in a clash of evolutionary titans. Proc Natl Acad Sci USA 102:14943-8.
3. Chackerian, B., C. Caldeira Jdo, J. Peabody, and D. S. Peabody. 2011. Peptide Epitope Identification by Affinity Selection on Bacteriophage MS2 Virus-Like Particles. J Mol Biol 409:225-37.
4. Ekiert, D. C., G. Bhabha, M. A. Elsliger, R. H. Friesen, M. Jongeneelen, M. Throsby, J. Goudsmit, and I. A. Wilson. 2009. Antibody recognition of a highly conserved influenza virus epitope. Science 324:246-51.
5. Gambhira, R., B. Karanam, S. Jagu, J. N. Roberts, C. B. Buck, I. Bossis, H. Alphs, T. Culp, N. D. Christensen, and R. B. Roden. 2007. A protective and broadly cross-neutralizing epitope of human papillomavirus L2. J Virol 81:13927-31.
6. Johnson, K. M., R. C. Kines, J. N. Roberts, D. R. Lowy, J. T. Schiller, and P. M. Day. 2009. Role of heparan sulfate in attachment to and infection of the murine female genital tract by human papillomavirus. J Virol 83:2067-74.
7. Karanam, B., S. Jagu, W. K. Huh, and R. B. Roden. 2009. Developing vaccines against minor capsid antigen L2 to prevent papillomavirus infection. Immunol Cell Biol 87:287-99.
8. Law, M., T. Maruyama, J. Lewis, E. Giang, A. W. Tarr, Z. Stamataki, P. Gastaminza, F. V. Chisari, I. M. Jones, R. I. Fox, J. K. Ball, J. A. McKeating, N. M. Kneteman, and D. R. Burton. 2008. Broadly neutralizing antibodies protect against hepatitis C virus quasispecies challenge. Nat Med 14:25-7.
9. Lim, F., T. P. Downey, and D. S. Peabody. 2001. Translational repression and specific RNA binding by the coat protein of the *Pseudomonas phage* PP7. J Biol Chem 276:22507-13.
10. Peabody, D. S., B. Manifold-Wheeler, A. Medford, S. K. Jordan, J. do Carmo Caldeira, and B. Chackerian. 2008. Immunogenic display of diverse peptides on Virus-like Particles of RNA phage MS2. Journal of Molecular Biology doi:10.1016/j.jmb/2008.04.049.
11. Roberts, J. N., C. B. Buck, C. D. Thompson, R. Kines, M. Bernardo, P. L. Choyke, D. R. Lowy, and J. T. Schiller. 2007. Genital transmission of HPV in a mouse model is potentiated by nonoxynol-9 and inhibited by carrageenan. Nat Med 13:857-61.
12. Sui, J., W. C. Hwang, S. Perez, G. Wei, D. Aird, L. M. Chen, E. Santelli, B. Stec, G. Cadwell, M. Ali, H. Wan, A. Murakami, A. Yammanuru, T. Han, N. J. Cox, L. A. Bankston, R. O. Donis, R. C. Liddington, and W. A. Marasco. 2009. Structural and functional bases for broad-spectrum neutralization of avian and human influenza A viruses. Nat Struct Mol Biol 16:265-73.

What is claimed is:

1. An MS2 RNA bacteriophage virus-like particle comprising a MS2 bacteriophage single chain coat polypeptide dimer having at least one human papillomavirus (HPV) L2 protein antigen corresponding to amino acids 17-31 of HPV type 16 L2 protein displayed on the N-terminus of the bacteriophage single chain coat polypeptide dimer.

2. The virus-like particle of claim 1, wherein the HPV L2 protein antigen is a HPV type 16 L2 protein antigen.

3. The virus-like particle of claim 1, wherein the HPV L2 protein antigen is an HPV type 1, 5, 6, 11, 16, 18, 31, 33, 35, 39, 45, 51, 52, 53, 56, 58, or 59 L2 protein antigen.

4. The virus-like particle of claim 1, wherein the RNA bacteriophage virus-like particle displays more than one HPV L2 protein antigen.

5. A composition comprising a population of virus-like particles of claim 1.

6. A method for enhancing an immune response against an antigen in an animal comprising introducing the composition of claim 5 into said animal, wherein an enhanced immune response against said antigen is produced in said animal.

7. The method of claim 6, wherein the composition is prophylactic for HPV-induced disorders.

8. The method of claim 6, wherein said immune response is an enhanced B cell response and/or an enhanced T cell response.

9. The method of claim 6, wherein said animal is a mammal.

10. The method of claim 6, wherein said composition is introduced into said animal subcutaneously, intramuscularly, intravenously, intranasally, intravaginally or directly into the lymph node.

11. A vaccine comprising an immunologically effective amount of the composition of claim 5 together with a pharmaceutically acceptable diluent, carrier or excipient.

12. A method of immunizing or treating an animal comprising administering to said animal an immunologically effective amount of the vaccine of claim 11.

13. The method of claim 12, wherein said animal is a mammal.

14. The vaccine of claim 11, wherein said vaccine further comprises an adjuvant.

* * * * *